US012714747B2

(12) United States Patent
Lesniak et al.

(10) Patent No.: US 12,714,747 B2
(45) Date of Patent: Aug. 25, 2026

(54) CYTOTOXIC LIPID PARTICLES TARGETED TO TUMOR-ASSOCIATED MYELOID CELLS (TAMCS) AND SYNERGIZED WITH RADIATION THERAPY FOR TREATING GLIOBLASTOMA

(71) Applicant: Northwestern University, Evanston, IL (US)

(72) Inventors: Maciej S. Lesniak, Evanston, IL (US); Peng Zhang, Chicago, IL (US)

(73) Assignee: Northwestern University, Evanston, IL (US)

( * ) Notice: Subject to any disclaimer, the term of this patent is extended or adjusted under 35 U.S.C. 154(b) by 21 days.

(21) Appl. No.: 17/089,563

(22) Filed: Nov. 4, 2020

(65) Prior Publication Data

US 2021/0128725 A1 May 6, 2021

Related U.S. Application Data

(60) Provisional application No. 62/930,555, filed on Nov. 4, 2019.

(51) Int. Cl.
*A61K 39/395* (2006.01)
*A61K 9/00* (2006.01)
(Continued)

(52) U.S. Cl.
CPC ........ *A61K 39/3955* (2013.01); *A61K 9/0019* (2013.01); *A61K 9/0043* (2013.01); *A61K 9/107* (2013.01); *A61K 9/1617* (2013.01); *A61K 9/1641* (2013.01); *A61K 31/519* (2013.01); *A61P 35/00* (2018.01)

(58) Field of Classification Search
CPC .............. A61K 39/3955; A61K 9/0019; A61K 9/0043; A61K 9/107; A61K 9/1617; A61K 9/1641; A61K 31/519; A61K 47/6849; A61K 47/6913; A61K 2039/505; A61P 35/00; C07K 16/2827
See application file for complete search history.

(56) References Cited

U.S. PATENT DOCUMENTS

2019/0330351 A1 10/2019 Campbell

FOREIGN PATENT DOCUMENTS

CN 108721643 A 11/2018
WO 2015026634 A1 2/2015
(Continued)

OTHER PUBLICATIONS

Cullis, P.R., et al (1989) Generating and loading of liposomal systems for drug-delivery applications Advanced Drug Delivery Reviews 3; 267-282 (Year: 1989).*
(Continued)

*Primary Examiner* — Scarlett Y Goon
*Assistant Examiner* — Audrey L Buttice
(74) *Attorney, Agent, or Firm* — Quarles & Brady LLP

(57) ABSTRACT

Disclosed are methods and compositions for treating cell proliferative diseases and disorders including cancers comprising tumor-associated myeloid cells (TAMCs) such as glioblastoma. The disclosed methods and composition may utilize or comprise cytotoxic lipid particles that comprise a surface-associated antibody or antigen-binding fragment thereof against PD-L1.

20 Claims, 67 Drawing Sheets
(67 of 67 Drawing Sheet(s) Filed in Color)

(51) Int. Cl.

| | |
|---|---|
| ***A61K 9/107*** | (2006.01) |
| ***A61K 9/16*** | (2006.01) |
| ***A61K 31/519*** | (2006.01) |
| ***A61P 35/00*** | (2006.01) |

(56) References Cited

FOREIGN PATENT DOCUMENTS

WO 2016172494 A2 10/2016
WO 2019177669 A1 9/2019

OTHER PUBLICATIONS

Torchilin, V.P. (2007) Micellar Nanocarriers: Pharmaceutical Perspectives Pharmaceutical Research 24(1); 1-16 (Year: 2007).*
Ahmed, A.E.E. (2018) Ultrasound triggered release of Trastuzumab-conjugated immunoliposomes targeting breast cancer Master of Science Thesis; American University of Sharjah; 1-125 (Year: 2018).*
Chen, R.Q., et al (2019) The Prognostic and Therapeutic Value of PD-L1 in Glioma Frontiers in Pharmacology 9(1503); 1-13 (Year: 2019).*
Vieira, D. and L.F. Gamarra (2016) Getting into the brain: liposome-based strategies for effective drug delivery across the blood-brain barrier International Journal of Nanomedicine 11; 5381-5414 (Year: 2016).*
Garcia-Pinel, B., et al (2019) Lipid-based nanoparticles: Applications and recent advances in cancer treatment Nanomaterials 9(638); 1-23 (Year: 2019).*
Wang, Y., et al (2018) Regulation of PD-L1: Emerging routes for targeting tumor immune evasion Frontiers in Pharmacology 9(536); 1-13 (Year: 2018).*
Ostrand-Rosenberg, S., et al (2019) Radiotherapy both promotes and inhibits myeloid-derived suppressor cell function: Novel strategies for preventing the tumor-protective effects of radiotherapy Frontiers in Oncology 9(215); 1-9 (Year: 2019).*
Zou W.P., Immunosuppressive networks in the tumour environment and their therapeutic relevance. Nat Rev Cancer 5, 263-274 (2005).
Alban T.J. et al., Global immune fingerprinting in glioblastoma patient peripheral blood reveals immune-suppression signatures associated with prognosis. JCI Insight 3 (2018).
Allen, T.M et al, Liposomal drug delivery systems: from concept to clinical applications. Adv Drug Deliv Rev 65, 36-48 (2013).
Antonios J.P. et al., Immunosuppressive tumor-infiltrating myeloid cells mediate adaptive immune resistance via a PD-1/PD-L1 mechanism in glioblastoma. Neuro Oncol 19, 796-807 (2017).
Avanti Polar Lipids, Inc., Catalog, "Functionalized Lipids,". Version dated Sep. 23, 2020. Available online at https://web.archive.org/web/20200923190546/https://avantilipids.com/product-category/headgroup-modified-lipids/functionalized-lipids.
Baghdadi M. et al., Chemotherapy-Induced IL34 Enhances Immunosuppression by Tumor-Associated Macrophages and Mediates Survival of Chemoresistant Lung Cancer Cells. Cancer Res 76, 6030-6042 (2016).
Benci J.L. et al., Tumor Interferon Signaling Regulates a Multigenic Resistance Program to Immune Checkpoint Blockade. Cell 167, 1540-1554 e1512 (2016).
Bloch O. et al., Gliomas Promote Immunosuppression through Induction of B7—H1 Expression in Tumor-Associated Macrophages. Clin Cancer Res 19, 3165-3175 (2013).
Brat D.J. et al., Comprehensive, Integrative Genomic Analysis of Diffuse Lower-Grade Gliomas. New Engl J Med 372, 2481-2498 (2015).
Bulbake, U. et al, Liposomal Formulations in Clinical Use: An Updated Review. Pharmaceutics 9 (2017).
Burr M.L. et al., CMTM6 maintains the expression of PD-L1 and regulates anti-tumour immunity. Nature 549, 101-105 (2017).
Chang A.L. et al., CCL2 Produced by the Glioma Microenvironment Is Essential for the Recruitment of Regulatory T Cells and Myeloid-Derived Suppressor Cells. Cancer Res 76, 5671-5682 (2016).
Cho, K.J. et al, Therapeutic nanoparticles for drug delivery in cancer. Clin Cancer Res 14, 1310-1316 (2008).
Davila M.L. et al., Efficacy and Toxicity Management of 19-28z CAR T Cell Therapy in B Cell Acute Lymphoblastic Leukemia. Sci Transl Med 6 (2014).
Deangelis L.M., Brain tumors. N Engl J Med 344, 114-123 (2001).
Deng L. et al., STING-Dependent Cytosolic DNA Sensing Promotes Radiation-Induced Type I Interferon-Dependent Antitumor Immunity in Immunogenic Tumors. Immunity 41, 843-852 (2014).
Dorand R.D. et al., Cdk5 disruption attenuates tumor PD-L1 expression and promotes antitumor immunity. Science 353, 399-403 (2016).
Engblom, C. et al, The role of myeloid cells in cancer therapies. Nat Rev Cancer 16, 447-462 (2016).
Fleming V. et al., Targeting Myeloid-Derived Suppressor Cells to Bypass Tumor-Induced Immunosuppression. Front Immunol 9, 398 (2018).
Gabrilovich, D.I. et al, Coordinated regulation of myeloid cells by tumours. Nature Reviews Immunology 12, 253-268 (2012).
Gabrilovich, D.I., Myeloid-derived suppressor cells as regulators of the immune system. Nat Rev Immunol 9, 162-174 (2009).
Hutter G. et al., Microglia are effector cells of CD47-SIRPalpha antiphagocytic axis disruption against glioblastoma. Proc Natl Acad Sci U S A 116, 997-1006 (2019).
International Searching Authority. International Search Report and Written Opinion for application PCT/US2020/058942. Mailed on Jan. 28, 2021. 10 pages.
Jackson, H.J. et al, Driving CAR T-cells forward. Nat Rev Clin Oncol 13, 370-383 (2016).
June, C.H. et al, CAR T cell immunotherapy for human cancer. Science 359, 1361-1365 (2018).
Kalbasi, A. et al, Radiation and immunotherapy: a synergistic combination. J Clin Invest 123, 2756-2763 (2013).
Kim, Y.J. et al, Phagocytosis, a potential mechanism for myeloid-derived suppressor cell regulation of CD8+ T cell function mediated through programmed cell death-1 and programmed cell death-1 ligand interaction. J Immunol 187, 2291-2301 (2011).
Wim, L. et al., Myeloid-derived suppressor cells reveal radioprotective properties through arginase-induced I-arginine depletion. Radiother Oncol 119, 291-299 (2016).
Liang H. et al., Host STING-dependent MDSC mobilization drives extrinsic radiation resistance. Nat Commun 8, 1736 (2017).
Lim, M. et al, Current state of immunotherapy for glioblastoma. Nature Reviews Clinical Oncology 15, 422-442 (2018).
Lugade A.A. et al., Local radiation therapy of B16 melanoma tumors increases the generation of tumor antigen-specific effector cells that traffic to the tumor. J Immunol 174, 7516-7523 (2005).
Mann, J. et al, Advances in Radiotherapy for Glioblastoma. Front Neurol 8 (2018).
Melero I. et al., Evolving synergistic combinations of targeted immunotherapies to combat cancer. Nat Rev Cancer 15, 457-472 (2015).
Mellman, I. et al, Cancer immunotherapy comes of age. Nature 480, 480-489 (2011).
Nakase I. et al., Receptor clustering and activation by multivalent interaction through recognition peptides presented on exosomes. Chem Commun (Camb) 53, 317-320 (2016).
Noman M.Z. et al., PD-L1 is a novel direct target of HIF-1alpha, and its blockade under hypoxia enhanced MDSC-mediated T cell activation. J Exp Med 211, 781-790 (2014).
Oh T. et al., Immunocompetent murine models for the study of glioblastoma immunotherapy. J Transl Med 12, 107 (2014).
Pardoll D.M., The blockade of immune checkpoints in cancer immunotherapy. Nat Rev Cancer 12, 252-264 (2012).
Preusser, M. et al, Prospects of immune checkpoint modulators in the treatment of glioblastoma. Nat Rev Neurol 11, 504-514 (2015).
Qin H. et al., Targeting tumor-associated myeloid cells for cancer immunotherapy. Oncoimmunology 4, e983961 (2015).

(56) References Cited

OTHER PUBLICATIONS

Quail, D.F. et al, The Microenvironmental Landscape of Brain Tumors. Cancer Cell 31, 326-341 (2017).
Raychaudhuri B. et al., Myeloid-derived suppressor cell accumulation and function in patients with newly diagnosed glioblastoma. Neuro-Oncology 13, 591-599 (2011).
Sharma, P. et al. Primary, Adaptive, and Acquired Resistance to Cancer Immunotherapy. Cell 168, 707-723 (2017).
Sica A. et al., Origin and Functions of Tumor-Associated Myeloid Cells (TAMCs). Cancer Microenviron 5, 133-149 (2012).
Stupp R. et al., Radiotherapy plus concomitant and adjuvant temozolomide for glioblastoma. N Engl J Med 352, 987-996 (2005).
Tandrup Schmidt, S., et al. "Liposome-based adjuvants for subunit vaccines: formulation strategies for subunit antigens and immunostimulators." Pharmaceutics 8.1 (2016): 7.
Tietjen, G.T. et al, Focus on Fundamentals: Achieving Effective Nanoparticle Targeting. Trends Mol Med 24, 598-606 (2018).
Van Weert, A.W. et al, Primaquine interferes with membrane recycling from endosomes to the plasma membrane through a direct interaction with endosomes which does not involve neutralisation of endosomal pH nor osmotic swelling of endosomes. Eur J Cell Biol 79, 394-399 (2000).
Wang, F. et al "Programmed death-ligand 1 monoclonal antibody-linked immunoliposomes for synergistic efficacy of miR-130a and oxaliplatin in gastric cancers." Nanomedicine 14.13 (2019): 1729-1744.
Weber R. et al., Myeloid-Derived Suppressor Cells Hinder the Anti-Cancer Activity of Immune Checkpoint Inhibitors. Front Immunol 9, 1310 (2018).
Zhang et al., "Therapeutic targeting of tumor-associated myeloid cells synergizes with radiation therapy for glioblastoma," PNAS Nov. 19, 2019, vol. 116, No. 47, pp. 23714-23723. (First published Nov. 11, 2019).

* cited by examiner

A

D

| | LNP | αPD-L1-LNP |
|---|---|---|
| Particle size (d, nm) | 81.4±0.8 | 91.6±1.2 |
| Polydispersity index | 0.181 | 0.206 |
| Zeta-potential (mV) | -0.35±0.16 | -2.93±0.88 |

F

E

F

H

A

A

C

CYTOTOXIC LIPID PARTICLES TARGETED TO TUMOR-ASSOCIATED MYELOID CELLS (TAMCS) AND SYNERGIZED WITH RADIATION THERAPY FOR TREATING GLIOBLASTOMA

CROSS-REFERENCE TO RELATED PATENT APPLICATIONS

This application claims the benefit of priority under 35 U.S.C. § 119(e) to U.S. Provisional Application No. 62/930,555, filed on Nov. 4, 2019, the content of which is incorporated by reference in its entirety.

STATEMENT REGARDING FEDERALLY SPONSORED RESEARCH OR DEVELOPMENT

This invention was made with government support under CA197725 awarded by the National Institutes of Health. The government has certain rights in the invention.

BACKGROUND

The field of the invention relates to methods and compositions for treating cell proliferative diseases and disorders such as cancer. In particular, the field of the invention relates to methods and compositions for treating brain cancers such as glioblastoma in a subject in need thereof via administering nanoparticles to the subject that are targeted to tumor-associated myeloid cells and optionally administering radiation therapy in conjunction with the administered nanoparticles.

Other researchers have tried to use therapeutic antibodies as immune checkpoint blockade inhibitors, or to use different targeting ligands, e.g. mannose, to target the delivery of therapeutics to myeloid cells. However, the present inventors here disclose a strategy that effectively and innovatively combines targeted delivery with checkpoint blockade therapy and radiation therapy, which allows for a significantly enhanced therapeutic outcome.

Immune checkpoint blockade therapy has been regarded as a promising strategy in the treatment of various types of tumors. However, to date, limited success has been achieved in anti-glioma therapy. Here, the inventors propose a new strategy as a dual-action system allowing a specific delivery of a therapeutic antibody and drug payloads to PD-L1 expressing immunosuppressive cells. The inventors' system enables a synergistic inhibition of PD-L1 through neutralization of expressed PD-L1 on cell plasma as well as inhibition of de-novo synthesis of PD-L1 inside cells. The inventors' strategy holds a great potential to improve the current immunotherapy for brain tumors and can be combined with conventional therapies, e.g. radiotherapy, chemotherapy, to maximize the clinical outcome.

The inventors' new nano-immunotherapy platform provides new strategies and mechanisms to improve current immunotherapy in the treatment of brain tumors and greatly enhances the efficacy of radiotherapy, a standard of care for brain tumor patients. The high efficiency of the inventors' system as shown in both murine and human glioma models warrants a rapid translation into clinical practice.

SUMMARY

Disclosed are methods and compositions for treating cell proliferative diseases and disorders including cancers comprising tumor-associated myeloid cells (TAMCs) such as glioblastoma. The disclosed methods and composition may utilize or comprise cytotoxic lipid particles that comprise a surface-associated antibody or antigen-binding fragment thereof against PD-L1.

The patent or application file contains at least one drawing executed in color. Copies of this patent or patent application publication with color drawing(s) will be provided by the Office upon request and payment of the necessary fee.

DETAILED DESCRIPTION

Figure 1:
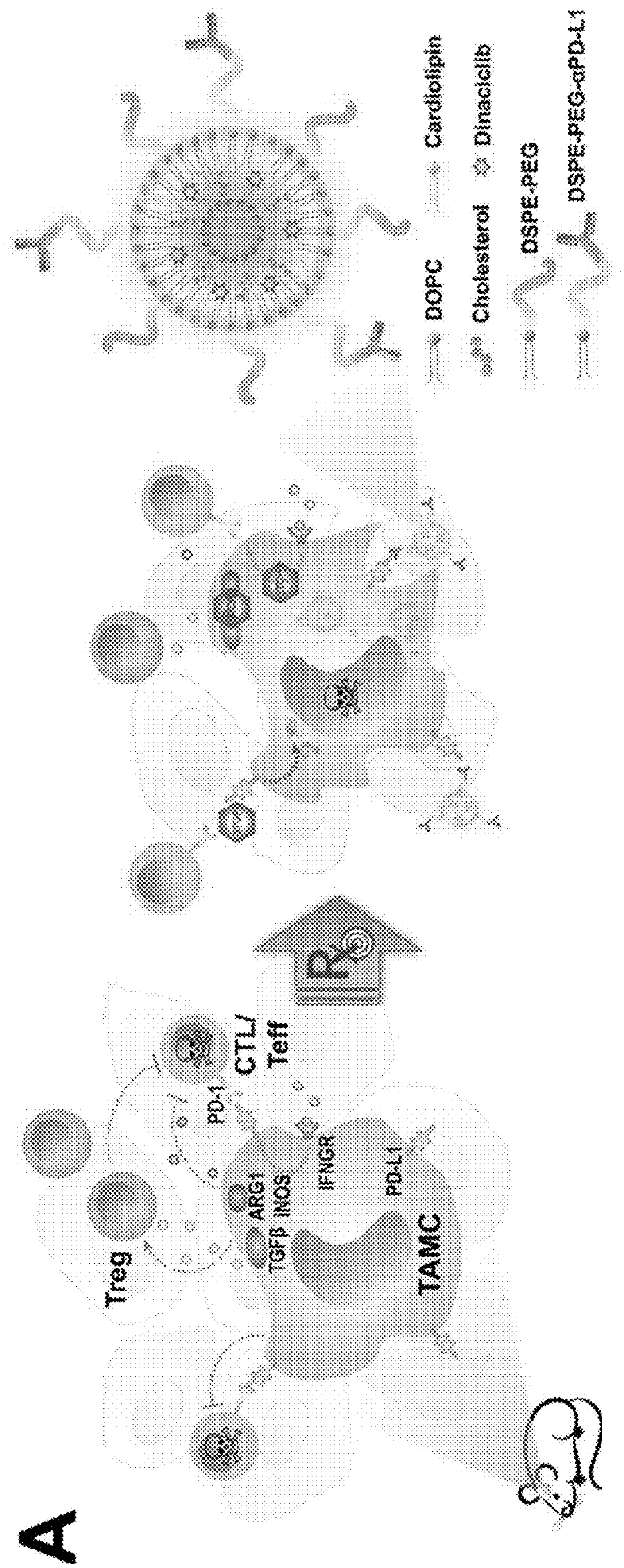
FIG. 1. Engineering of therapeutic LNPs targeting of glioma-associated TAMCs. (A) Schematic representation of nano-targeting of glioma-associated TAMCs. (CTL, cytotoxic T lymphocyte; Teff, effector T cell; PD-1, programmed cell death protein 1; IFNGR, interferon gamma receptor). (B-C) Flow cytometric quantification of PD-L1 expression among glioma-infiltrating immune cells in GL261 glioma model, as determined by percentage of PD-L1$^+$ cells (B) (blue, control; red, PE anti-mouse PD-L1), and MFI (C). Data are represented as mean±SEM; n=3; ***, $p<0.001$; determined by one-way ANOVA with Tukey's multiple comparisons test. (D) αPD-L1-functionalized lipid nanoparticle (αPD-L1-LNP) and naked lipid nanoparticle (LNP) were characterized by cryo-EM, DLS, and zeta-potential. Scale bar, 50 nm.
Figure 1:
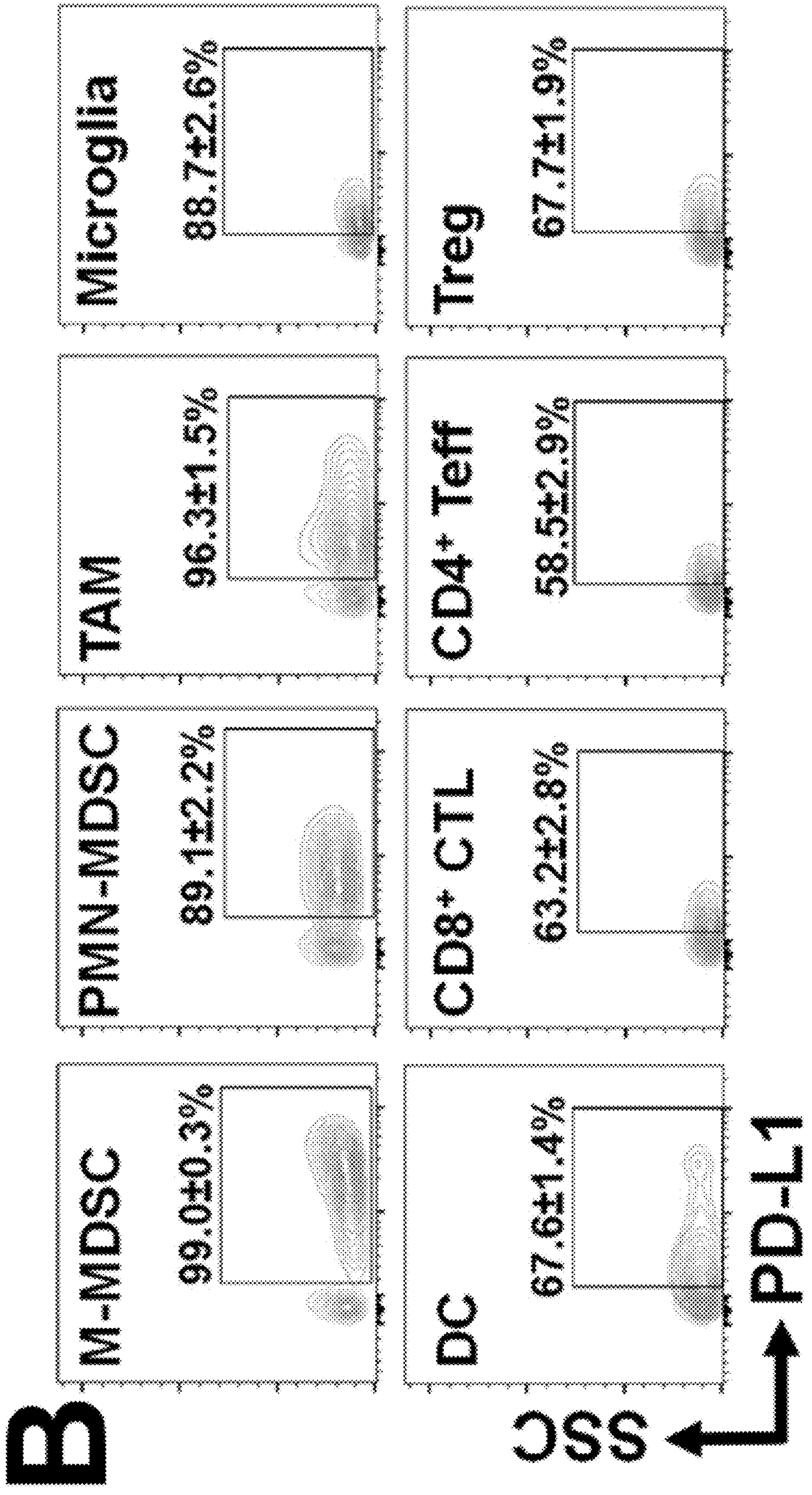
Figure 1:
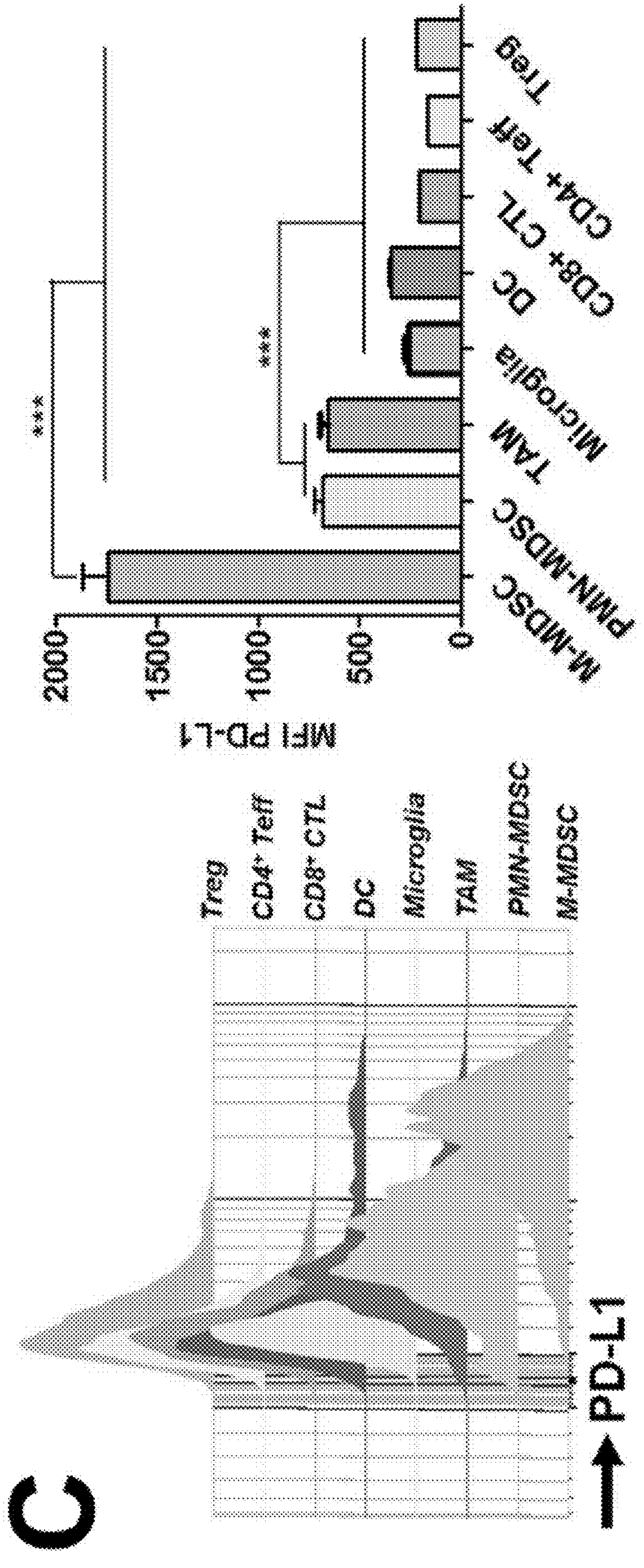
Figure 1:
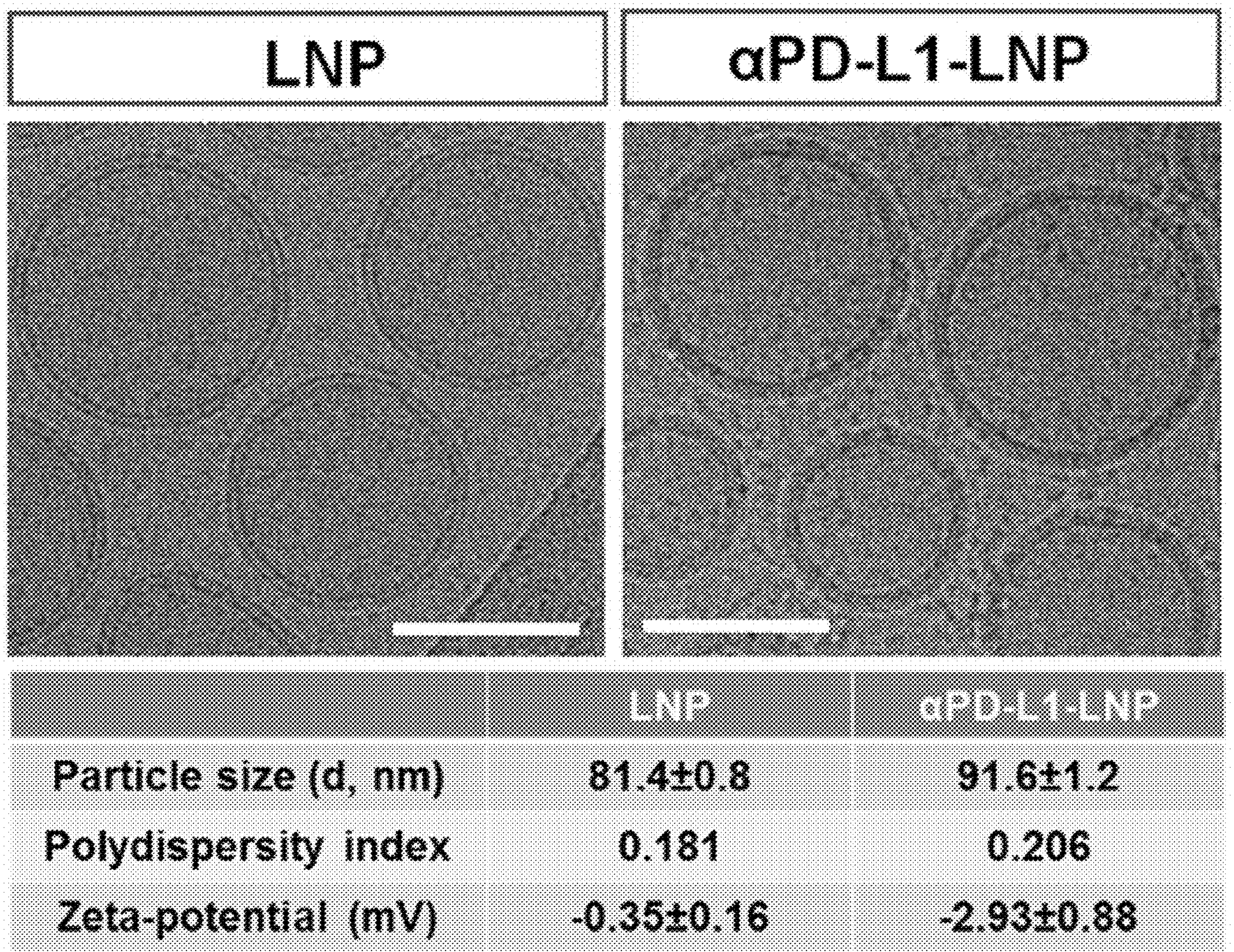

The disclosed subject matter further may be described utilizing terms as defined below.

Unless otherwise specified or indicated by context, the terms "a", "an", and "the" mean "one or more." For example, "a therapeutic agent" should be interpreted to mean "one or more therapeutic agents."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

The terms "subject," "patient," and "individual" may be used interchangeably herein. A subject may be a human subject. A subject may refer to a human subject having or at risk for acquiring a cell proliferative disease or disorder such as cancer, and in particular, brain cancers such as glioblastoma.

The methods and composition disclosed herein may comprise or utilize cytotoxic lipid particles. The cytotoxic particles typically are relatively small and may have an effective average diameter of less than about 10000, 5000, 4000, 3000, 2000, 1000, 900, 800, 700, 600, 500, 400, 300, 200, 100, 90, 80, 70, 60, or 50 nm, or an effective average diameter within a range bound by any of these values (e.g., 800-100 nm). In some embodiments, the cytotoxic lipid particles disclosed herein may be referred to herein as "nanoparticles."

Cytotoxic Lipid Particles Targeted to Tumor-Associated Myeloid Cells (TAMCs) and Optionally Synergized with Radiation Therapy for Treating Cell Proliferative Diseases and Disorders The subject matter of the application relates to methods and compositions for treating cell proliferative diseases and disorders including cancer. The methods and compositions particularly relate to methods for treating brain cancers such as glioblastomas. The methods and compositions may be utilized to target tumor-associated myeloid cells (TAMCs) present within a glioblastoma.

The disclosed methods and compositions may utilize or comprise cytotoxic lipid particles, for example, which are formulated as a pharmaceutical formulation for treating a cell proliferative disease or disorder. The disclosed cytotoxic lipid particles typically include a surface-associated antibody or antigen-binding fragment thereof against PD-L1.

In particular, the disclosed cytotoxic may include a cytotoxic agent used in chemotherapy for treating cancer. Suitable cytotoxic agents may include, but are not limited to Abiraterone Acetate, Abitrexate (Methotrexate), Adriamycin (Doxorubicin Hydrochloride), Adrucil (Fluorouracil), Afatinib Dimaleate, Afinitor (Everolimus), Aldesleukin, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Asparaginase *Erwinia chrysanthemi*, Axitinib, Azacitidine, Becenum (Carmustine), Beleodaq (Belinostat), Belinostat, Bendamustine Hydrochloride, Bexarotene, Bicalutamide, BiCNU (Carmustine), Bleomycin, Bortezomib, Bosulif (Bosutinib), Bosutinib, Busulfan, Busulfex (Busulfan), Cabazitaxel, Cabozantinib-S-Malate, Camptosar (Irinotecan Hydrochloride), Capecitabine, Carboplatin, CARBOPLATIN-TAXOL, Carfilzomib, Carmubris (Carmustine), Carmustine, Casodex (Bicalutamide), CeeNU (Lomustine), Ceritinib, Cerubidine (Daunorubicin Hydrochloride), Chlorambucil, CHLORAMBUCL-PREDNISONE, Cisplatin, Clafen (Cyclophosphamide), Clofarabine, Clofarex (Clofarabine), Clolar (Clofarabine), Cometriq (Cabozantinib-S-Malate), Cosmegen (Dactinomycin), Crizotinib, Cyclophosphamide, Cyfos (Ifosfamide), Cytarabine, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Dexrazoxane Hydrochloride, Dinaciclib (Dina), Docetaxel, Doxorubicin Hydrochloride, DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, Eribulin Mesylate, Erivedge (Vismodegib), Erlotinib Hydrochloride, Erwinaze (Asparaginase *Erwinia chrysanthemi*), Etopophos (Etoposide Phosphate), Etoposide, Etoposide Phosphate, Everolimus, Evista (Raloxifene Hydrochloride), Exemestane, Fareston (Toremifene), Farydak (Panobinostat), Faslodex (Fulvestrant), Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRINOX, FOLFOX, Folotyn (Pralatrexate), Fulvestrant, Gefitinib, Gemcitabine Hydrochloride, GEMCITABINE-CISPLATIN, GEMCITABINE-OXALIPLATIN, Gemzar (Gemcitabine Hydrochloride), Gilotrif (Afatinib Dimaleate), Gleevec (Imatinib Mesylate), Gliadel (Carmustine Implant), Glucarpidase, Goserelin Acetate, Halaven (Eribulin Mesylate), Hycamtin (Topotecan Hydrochloride), Ibrance (Palbociclib), Ibrutinib, Iclusig (Ponatinib Hydrochloride), Idamycin (Idarubicin Hydrochloride), Idarubicin Hydrochloride, Idelalisib, Ifex (Ifosfamide), Ifosfamide, Ifosfamidum (Ifosfamide), Imatinib Mesylate, Imbruvica (Ibrutinib), Inlyta (Axitinib), Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Keoxifene (Raloxifene Hydrochloride), Kyprolis (Carfilzomib), Lanreotide Acetate, Lapatinib Ditosylate, Lenalidomide, Lenvatinib Mesylate, Lenvima (Lenvatinib Mesylate), Letrozole, Leucovorin Calcium, Leukeran (Chlorambucil), Leuprolide Acetate, Levulan (Aminolevulinic Acid), Linfolizin (Chlorambucil), Lomustine, Lupron (Leuprolide Acetate), Lynparza (Olaparib), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitoxantrone Hydrochloride, Mitozytrex (Mitomycin C), Mozobil (Plerixafor), Mustargen (Mechlorethamine Hydrochloride), Mutamycin (Mitomycin C), Myleran (Busulfan), Mylosar (Azacitidine), Navelbine (Vinorelbine Tartrate), Nelarabine, Neosar (Cyclophosphamide), Nexavar (Sorafenib Tosylate), Nilotinib, Nolvadex (Tamoxifen Citrate), Nplate (Romiplostim), Olaparib, Omacetaxine Mepesuccinate, Ontak (Denileukin Diftitox), Oxaliplatin, Paclitaxel, Palbociclib, Palonosetron Hydrochloride, Pamidronate Disodium, Panobinostat, Paraplat (Carboplatin), Paraplatin (Carboplatin), Pazopanib Hydrochloride, Pemetrexed Disodium, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Promacta (Eltrombopag Olamine), Purinethol (Mercaptopurine), Purixan (Mercaptopurine), Radium 223 Dichloride, Raloxifene Hydrochloride, Regorafenib, Revlimid (Lenalidomide), Rheumatrex (Methotrexate), Romidepsin, Romiplostim, Rubidomycin (Daunorubicin Hydrochloride), Ruxolitinib Phosphate, Sorafenib Tosylate, Sprycel (Dasatinib), Stivarga (Regorafenib), Sunitinib Malate, Sutent (Sunitinib Malate), Synovir (Thalidomide), Synribo (Omacetaxine Mepesuccinate), Tafinlar (Dabrafenib), Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Thiotepa, Toposar (Etoposide), Topotecan Hydrochloride, Toremifene, Torisel (Temsirolimus), Totect (Dexrazoxane Hydrochloride), Trametinib, Treanda (Bendamustine Hydrochloride), Trisenox (Arsenic Trioxide), Tykerb (Lapatinib Ditosylate), Vandetanib, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vinorelbine Tartrate, Vismodegib, Vorinostat, Votrient (Pazopanib Hydrochloride), Wellcovorin (Leucovorin Calcium), Xalkori (Crizotinib), Xeloda (Capecitabine), Xofigo (Radium 223 Dichloride), Xtandi (Enzalutamide), Zaltrap (Ziv-Aflibercept), Zelboraf (Vemurafenib), Zinecard (Dexrazoxane Hydrochloride), Ziv-Aflibercept, Zoladex (Goserelin Acetate), Zoledronic Acid, Zolinza (Vorinostat), Zometa (Zoledronic Acid), Zydelig (Idelalisib), Zykadia (Ceritinib), Zytiga (Abiraterone Acetate), and combinations thereof. Specifically, the disclosed cytotoxic lipid particles may comprise a cyclin-dependent kinase 5 inhibitor, which may include, but is not limited to Dinaciclib (Dina).

The disclosed cytotoxic lipid particles may comprise a suitable concentration of a cytotoxic agent for treating a tumor. In some embodiments, the disclosed cytotoxic lipid particles may comprise a cytotoxic agent at a concentration value of at least about 1, 2, 5, 10, 20, 30, 40, 50, 60, 70, 80, 90, 100, 120, 140, 160, 180, 200, or 300 μg/mg; or the cytotoxic lipid particles may comprise the cytotoxic agent at a concentration value of no more than about 300, 200, 180, 160, 140, 120, 100, 90, 80, 70, 60, 50, 40, 30, 20, 10, 5, 2, or 1 μg/mg cytotoxic agent; or the cytotoxic lipid particles may comprise the cytotoxic agent within a concentration range bounded by any two of the preceding concentration values.

The disclosed cytotoxic lipid particles comprise lipids. In some embodiments, the disclosed cytotoxic lipid particles comprise amphipathic lipid molecules that form one or more lipid layers. In some embodiments, the cytotoxic lipid particles comprise lipid multi-layers, such as a lipid bi-layer as typically present in liposomes. In other embodiments, the cytotoxic lipid layers comprise amphipathic lipid molecules that form a micelle.

The disclosed cytotoxic lipid particles may comprise any lipid that a suitable for incorporating a cytotoxic agent and forming a particle. In some embodiments, the cytotoxic lipid particles comprise phospholipids. Suitable phospholipids may include, but are not limited to, phosphoglycerides, such as phosphocholines, phosphoethanolamines, and phosphatidylethanolamines. The disclosed cytotoxic lipid particles may comprise modified phosphoglycerides, for example, polyethylenene glycol (PEG)-modified phosphoglycerides. The disclosed cytotoxic lipid particles may comprise functionalized phospholipids as known in the art. (See, e.g., Avanti Polar Lipids, Inc., Catalog, "Functionalized Lipids," the content of which is incorporated herein by reference in its entirety). Optionally, the disclosed cytotoxic lipid particles may comprise functionalized phospholipids optionally functionalized with a group selected from a maleimidoalkyl group, a maleimidoaryl group, a N-succinimidylalkyl group, an aminoalkyl group, an oxoalkoxy group, a thiolalkyl group, a pyridyldithio group, a carboxyalkyl group, and a biotinyl group.

The disclosed cytotoxic lipid particles may sterols. Suitable sterols for the disclosed cytotoxic lipid particles may include, but are not limited to, cholesterol.

The disclosed cytotoxic lipid particles may be relatively small and have an effective average diameter suitable for administering the cytotoxic lipid particles to treat a cell proliferative disease and disorder (e.g., a brain cancer such as glioblastoma). In some embodiments, the disclosed cytotoxic lipid particles have an effective average diameter of less than about 10000, 5000, 4000, 3000, 2000, 1000, 900, 800, 700, 600, 500, 400, 300, 200, 100, 90, 80, 70, 60, or 50 nm, or an effective average diameter within a range bounded by any of these values (e.g., 1000-100 nm or where the cytotoxic lipid particles are cytotoxic lipid nanoparticles).

The disclosed cytotoxic lipid particles typically comprise a surface-associated antibody or antigen-binding fragment thereof against PD-L1. Anti-PD-L1 antibodies are known in the art and may include, but are not limited to, atezolizumab, avelumab, durvalumab, and KN035. (See also, U.S. Published Application No. 2019/0330351; and BioLegend Catalog, Purified anti-human CD274 (B7-H1, PD-L1) Antibody). Suitable antibody or antigen-binding fragment thereof against PD-L1 may include, but are not limited to monoclonal antibodies, human or humanized antibodies, chimeric antibodies, single chain antibodies, Fab fragments, Fv fragments, $F(ab')_2$ fragments, or scFv fragments, and/or IgG isotypes (e.g., IgG1 such as human IgG1).

The disclosed cytotoxic lipid particles typically include a surface-associated antibody or antigen-binding fragment thereof against PD-L1. In some embodiments, the surface-associated antibody or antigen-binding fragment thereof against PD-L1 is covalently attached to the cytotoxic lipid particles. The surface-associated antibody or antigen-binding fragment thereof against PD-L1 may have been functionalized (e.g., via reaction with a functionalizing agent such as 2-imiothiolane) and covalently attached to the cytotoxic lipid particles via functionalized phospholipids.

The disclosed cytotoxic lipid particles may comprise the surface-associated antibody or antigen-binding fragment thereof against PD-L1 at a suitable concentration for targeting the cytotoxic lipid particles to cells that express PD-L1, such as tumor-associated myeloid cells (TAMCs). In some embodiments, the cytotoxic lipid particles comprise the surface-associated antibody or antigen-binding fragment thereof at a concentration of at least about 1, 2, 5, 10, 20, 30, 40, 50, 60, 70, 80, 90, 100, 120, 140, 160, 180, or 200 μg/mg or within a concentration range bounded by any two of these values (e.g., 20-120 μg/mg).

The disclosed cytotoxic lipid particles may be utilized to treat a disease or disorder in a subject in need thereof, such as a subject having a cell proliferative disease or disorder (e.g., cancers such as glioblastoma). As such, the disclosed cytotoxic lipid particles may be utilized to prepare a pharmaceutical composition comprising the cytotoxic lipid particles and a suitable carrier, excipient, or diluent.

Also disclosed are methods of treating diseases or disorders such as cell proliferative diseases and disorders. Particularly disclosed are methods for treating cancers comprising tumor-associated myeloid cells (TAMCs) in a subject in need thereof, where in the disclosed methods, the subject is administered the disclosed cytotoxic lipid particles (e.g., as part of a pharmaceutical composition as disclosed herein). In some embodiments, the disclosed methods treat a subject having glioblastoma, where the subject is administered the disclosed cytotoxic lipid particles (e.g., as part of a pharmaceutical composition as disclosed herein). The disclosed cytotoxic lipid particles or pharmaceutical compositions comprising the disclosed cytotoxic lipid particles may be administered by any suitable route of delivery. In some embodiments, the disclosed cytotoxic lipid particles or pharmaceutical compositions comprising the disclosed cytotoxic lipid particles may be administered intracranially. In other embodiments, disclosed cytotoxic lipid particles or pharmaceutical compositions comprising the disclosed cytotoxic lipid particles may be administered intranasally.

The disclosed methods of a treatment further may include administering radiation therapy to a subject. In some embodiments of the disclosed methods of treatment, a subject is administered the disclosed cytotoxic lipid particles or pharmaceutical compositions comprising the disclosed cytotoxic lipid and subsequently is administered radiation therapy. In other embodiments, a subject is administered radiation therapy and subsequent is administered the cytotoxic lipid particles or pharmaceutical compositions comprising the disclosed cytotoxic lipid particles.

ILLUSTRATIVE EMBODIMENTS

The following Embodiments are illustrative and should not be interpreted to limit the scope of the claimed subject matter.

Embodiment 1. Cytotoxic lipid particles comprising a surface-associated antibody or antigen-binding fragment thereof against PD-L1.

Embodiment 2. The cytotoxic lipid particles of embodiment 1, wherein the cytotoxic lipid particles comprise a cytotoxic agent used in chemotherapy for treating cancer.

Embodiment 3. The cytotoxic lipid particles of embodiment 1, wherein the cytotoxic lipid particles comprise a cytotoxic agent selected from the group consisting of Abiraterone Acetate, Abitrexate (Methotrexate), Adriamycin (Doxorubicin Hydrochloride), Adrucil (Fluorouracil), Afatinib Dimaleate, Afinitor (Everolimus), Aldesleukin, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Asparaginase *Erwinia chrysanthemi*, Axitinib, Azacitidine, Becenum (Carmustine), Beleodaq (Belinostat), Belinostat, Bendamustine Hydrochloride, Bexarotene, Bicalutamide, BiCNU (Carmustine), Bleomycin, Bortezomib, Bosulif (Bosutinib), Bosutinib, Busulfan, Busulfex (Busulfan), Cabazitaxel, Cabozantinib-S-Malate, Camptosar (Irinotecan Hydrochloride), Capecitabine, Carboplatin, CARBOPLATIN-TAXOL, Carfilzomib, Carmubris (Carmustine), Carmustine, Casodex (Bicalutamide), CeeNU (Lomustine), Ceritinib, Cerubidine (Daunorubicin Hydrochloride), Chlorambucil, CHLORAMBUCIL-PREDNISONE, Cisplatin, Clafen (Cyclophosphamide), Clofarabine, Clofarex (Clofarabine), Clolar (Clofarabine), Cometriq (Cabozantinib-S-Malate), Cosmegen (Dactinomycin), Crizotinib, Cyclophosphamide, Cyfos (Ifosfamide), Cytarabine, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Dexrazoxane Hydrochloride, Dinaciclib (Dina), Docetaxel, Doxorubicin Hydrochloride, DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, Eribulin Mesylate, Erivedge (Vismodegib), Erlotinib Hydrochloride, Erwinaze (Asparaginase *Erwinia chrysanthemi*), Etopophos (Etoposide Phosphate), Etoposide, Etoposide Phosphate, Everolimus, Evista (Raloxifene Hydrochloride), Exemestane, Fareston (Toremifene), Farydak (Panobinostat), Faslodex (Fulvestrant), Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), FOLFIRINOX, FOLFOX, Folotyn (Pralatrexate), Fulvestrant, Gefitinib, Gemcitabine Hydrochloride, GEMCITABINE-CISPLATIN, GEMCITABINE-OXALIPLATIN, Gemzar (Gemcitabine Hydrochloride), Gilotrif (Afatinib Dimaleate), Gleevec (Imatinib Mesylate), Gliadel (Carmustine Implant), Glucarpidase, Goserelin Acetate, Halaven (Eribulin Mesylate), Hycamtin (Topotecan Hydrochloride), Ibrance (Palbociclib), Ibrutinib, Iclusig (Ponatinib Hydrochloride), Idamycin (Idarubicin Hydrochloride), Idarubicin Hydrochloride, Idelalisib, Ifex (Ifosfamide), Ifosfamide, Ifosfamidum (Ifosfamide), Imatinib Mesylate, Imbruvica (Ibrutinib), Inlyta (Axitinib), Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Keoxifene (Raloxifene Hydrochloride), Kyprolis (Carfilzomib), Lanreotide Acetate, Lapatinib Ditosylate, Lenalidomide, Lenvatinib Mesylate, Lenvima (Lenvatinib Mesylate), Letrozole, Leucovorin Calcium, Leukeran (Chlorambucil), Leuprolide Acetate, Levulan (Aminolevulinic Acid), Linfolizin (Chlorambucil), Lomustine, Lupron (Leuprolide Acetate), Lynparza (Olaparib), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitoxantrone Hydrochloride, Mitozytrex (Mitomycin C), Mozobil (Plerixafor), Mustargen (Mechlorethamine Hydrochloride), Mutamycin (Mitomycin C), Myleran (Busulfan), Mylosar (Azacitidine), Navelbine (Vinorelbine Tartrate), Nelarabine, Neosar (Cyclophosphamide), Nexavar (Sorafenib Tosylate), Nilotinib, Nolvadex (Tamoxifen Citrate), Nplate (Romiplostim), Olaparib, Omacetaxine Mepesuccinate, Ontak (Denileukin Diftitox), Oxaliplatin, Paclitaxel, Palbociclib, Palonosetron Hydrochloride, Pamidronate Disodium, Panobinostat, Paraplat (Carboplatin), Paraplatin (Carboplatin), Pazopanib Hydrochloride, Pemetrexed Disodium, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Promacta (Eltrombopag Olamine), Purinethol (Mercaptopurine), Purixan (Mercaptopurine), Radium 223 Dichloride, Raloxifene Hydrochloride, Regorafenib, Revlimid (Lenalidomide), Rheumatrex (Methotrexate), Romidepsin, Romiplostim, Rubidomycin (Daunorubicin Hydrochloride), Ruxolitinib Phosphate, Sorafenib Tosylate, Sprycel (Dasatinib), Stivarga (Regorafenib), Sunitinib Malate, Sutent (Sunitinib Malate), Synovir (Thalidomide), Synribo (Omacetaxine Mepesuccinate), Tafinlar (Dabrafenib), Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Thiotepa, Toposar (Etoposide), Topotecan Hydrochloride, Toremifene, Torisel (Temsirolimus), Totect (Dexrazoxane Hydrochloride), Trametinib, Treanda (Bendamustine Hydrochloride), Trisenox (Arsenic Trioxide), Tykerb (Lapatinib Ditosylate), Vandetanib, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vinorelbine Tartrate, Vismodegib, Vorinostat, Votrient (Pazopanib Hydrochloride), Wellcovorin (Leucovorin Calcium), Xalkori (Crizotinib), Xeloda (Capecitabine), Xofigo (Radium 223 Dichloride), Xtandi (Enzalutamide), Zaltrap (Ziv-Aflibercept), Zelboraf (Vemurafenib), Zinecard (Dexrazoxane Hydrochloride), Ziv-Aflibercept, Zoladex (Goserelin Acetate), Zoledronic Acid, Zolinza (Vorinostat), Zometa (Zoledronic Acid), Zydelig (Idelalisib), Zykadia (Ceritinib), Zytiga (Abiraterone Acetate), and combinations thereof.

Embodiment 4. The cytotoxic lipid particles of any of the foregoing embodiments, wherein the cytotoxic lipid particles comprise Dinaciclib (Dina).

Embodiment 5. The cytotoxic lipid particles of any of the foregoing embodiments, wherein the cytotoxic lipid particles comprise a suitable concentration of the cytotoxic agent for treating a tumor (e.g., the cytotoxic lipid particles may comprise the cytotoxic agent at a concentration value of at least about 1, 2, 5, 10, 20, 30, 40, 50, 60, 70, 80, 90, 100, 120, 140, 160, 180, 200, or 300 μg/mg; or the cytotoxic lipid particles may comprise the cytotoxic agent at a concentration value of no more than about 300, 200, 180, 160, 140, 120, 100, 90, 80, 70, 60, 50, 40, 30, 20, 10, 5, 2, or 1 μg/mg cytotoxic agent; or the cytotoxic lipid particles may comprise the cytotoxic agent within a concentration range bounded by any two of the preceding concentration values.

Embodiment 6. The cytotoxic lipid particles of any of the foregoing embodiments, wherein the cytotoxic lipid particles comprise a lipid multi-layers (e.g., wherein the cytotoxic lipid particles comprise bi-layers such as liposomes).

Embodiment 7. The cytotoxic lipid particles of any of the foregoing embodiments, wherein the cytotoxic lipid particles comprise micelles.

Embodiment 8. The cytotoxic lipid particles of any of the foregoing embodiments, wherein the cytotoxic lipid particles comprise phospholipids.

Embodiment 9. The cytotoxic lipid particles of any of the foregoing embodiments, wherein the cytotoxic lipid particles comprise phosphoglycerides (e.g., phosphocholines, phosphoethanolamines, and phosphatidylethanolamines)

Embodiment 10. The cytotoxic lipid particles of any of the foregoing embodiments, wherein the cytotoxic lipid particles comprise polyethylenine glycol (PEG)-modified phosphoglycerides.

Embodiment 11. The cytotoxic lipid particles of any of the foregoing embodiments, wherein the cytotoxic lipid particles comprise functionalized phospholipids, optionally phospholipids that are functionalized with a group selected from a maleimidoalkyl group, a maleimidoaryl group, a N-succinimidylalkyl group, an aminoalkyl group, an oxoalkoxy group, a thiolalkyl group, a pyridyldithio group, a carboxyalkyl group, and a biotinyl group.

Embodiment 12. The cytotoxic lipid particles of any of the foregoing embodiments, wherein the cytotoxic lipid particles comprise cholesterol.

Embodiment 13. The cytotoxic lipid particles of any of the foregoing embodiments, wherein the cytotoxic lipid particles having an effective average diameter of less than about 10000, 5000, 4000, 3000, 2000, 1000, 900, 800, 700, 600, 500, 400, 300, 200, 100, 90, 80, 70, 60, or 50 nm, or an effective average diameter within a range bounded by any of these values (e.g., 1000-100 nm or where the cytotoxic lipid particles are cytotoxic lipid nanoparticles).

Embodiment 14. The cytotoxic lipid particles of any of the foregoing embodiments, wherein the surface-associated antibody or antigen-binding fragment thereof against PD-L1 is covalently attached to the cytotoxic lipid particles.

Embodiment 15. The cytotoxic lipid particles of any of the foregoing embodiments, wherein the surface-associated antibody or antigen-binding fragment thereof against PD-L1 has been functionalized (e.g., via reaction with a functionalizing agent such as 2-imiothiolane) and covalently attached to the cytotoxic lipid particles via functionalized phospholipids.

Embodiment 16. The cytotoxic lipid particles of any of the foregoing embodiments, wherein the cytotoxic lipid particles comprise the surface-associated antibody or antigen-binding fragment thereof at a concentration of at least about 1, 2, 5, 10, 20, 30, 40, 50, 60, 70, 80, 90, 100, 120, 140, 160, 180, or 200 μg/mg or within a concentration range bounded by any two of these values (e.g., 20-120 μg/mg).

Embodiment 17. A pharmaceutical composition comprising the cytotoxic lipid particles of any of the foregoing embodiments and a suitable carrier, excipient, or diluent.

Embodiment 18. A method for treating a cancer comprising tumor-associated myeloid cells (TAMCs) in a subject in need thereof, the method comprising administering to the subject the pharmaceutical composition of embodiment 17.

Embodiment 19. The method of embodiment 18, wherein the cancer is glioblastoma.

Embodiment 20. The method of embodiment 18 or 19, wherein the pharmaceutical composition is administered intracranially.

Embodiment 21. The method of embodiment 18 or 19, wherein the pharmaceutical composition is administered intranasally.

Embodiment 22. The method of any of embodiments 18-21 further comprising administering to the subject radiotherapy.

Embodiment 23. The method of embodiment 22, wherein the radiotherapy is administered to the subject after the pharmaceutical composition is administered to the subject.

Embodiment 24. The method of embodiment 22, wherein the radiotherapy is administered to the subject before the pharmaceutical composition is administered to the subject.

Embodiment 25. A treatment protocol for a subject having glioblastoma, the protocol comprising: (i) administering to the subject the pharmaceutical composition of embodiment 17; and (ii) administering to the subject radiotherapy.

EXAMPLES

The followings Example is illustrative only should not be interpreted to limit the scope of the claimed subject matter.

Example 1—New Therapeutic Strategy for Anti-Cancer Therapy

Abstract

Tumor-associated myeloid cells (TAMCs) are a key driver of immunosuppression and therapy resistance in glioblastoma (GBM), the deadliest malignant brain tumors. The fact that TAMCs compose up to 50% of the brain tumor mass further highlighted the urgent need to develop new therapeutic strategy to effectively target TAMCs in GBM. We have established a lipid nanoparticle (LNP) platform capable of actively targeting and delivering therapeutics to mouse and human TAMCs. We have shown that therapeutic LNPs effectively eliminated TAMCs from glioma, and significantly improved therapeutic outcome in glioma models as combination with radiation therapy. This nanomedicine platform holds great potential for improved treatment of GBM and a rapid translation into clinical practice.

Applications

Applications of the disclosed technology may include, but are not limited to: (i) a new strategy to improve current checkpoint blockade therapy for cancer; (ii) a new and effective therapeutic platform for glioblastoma; (iii) a therapeutic platform that is translatable to clinical application as new immunotherapy strategy, or as combination therapy with radiation or checkpoint blockade therapy for improved therapeutic efficacy; and (iv) a versatile therapeutic platform that could be feasible for delivery of a variety of therapeutics in different disease models.

Advantages

Advantages of the disclosed technology may include, but are not limited to: (i) the technology provides new mechanism and enhanced efficacy compared to current immune checkpoint blockade therapy; (ii) the technology synergizes with radiation therapy, a standard of care in brain tumor treatment, to greatly improve the therapeutic outcome; (iii) LNPs have been approved by FDA as clinically used formulation to deliver therapeutics; and (iv) the technology is cost effective relative to checkpoint blockade therapy and gold nanoparticle based delivery strategy.

Brief Description of the Technology

Tumor-associated myeloid cells (TAMCs) are a key driver of immunosuppression in the tumor microenvironment, which profoundly impedes the clinical response to immune-dependent and conventional therapeutic modalities. As a hallmark of glioblastoma (GBM), TAMCs are massively recruited to reach up to 50% of the brain tumor mass. Thereby, TAMCs have recently been recognized as an appealing therapeutic target to blunt immunosuppression in GBM with the hope to maximize the clinical outcome of antitumor therapies. We have established a new nano-immunotherapy approach capable of actively targeting TAMCs in GBM. As we found that PD-L1 is highly expressed on glioma-associated TAMCs, we rationally designed a lipid nanoparticle (LNP) formulation surface-functionalized with anti-PD-L1 therapeutic antibody (αPD-L1). This system (αPD-L1-LNP) could enable effective and specific delivery of therapeutic payload to TAMCs. Specifically, encapsulation of dinaciclib, a cyclin-dependent kinase inhibitor, into PD-L1-targeted LNP led to a robust depletion of TAMCs, and an attenuation of their immunosuppressive functions. Importantly, the delivery efficiency of PD-L1-targeted LNP was robustly enhanced in the context of radiation therapy (RT). Accordingly, an RT combined with our nano-immunotherapy led to dramatically extended survival of mice in syngeneic glioma models. The high targeting efficiency of αPD-L1-LNP to human TAMCs isolated from GBM patients further validated the clinical relevance. Thus, we are proposing a new therapeutic platform with immense potential to improve the clinical response in the treatment of GBM, which warrants a rapid translation into clinical practice.

We are proposing a new nano-immunotherapy approach capable of actively targeting tumor-associated myeloid cells (TAMCs) to blunt the immunosuppression and enhance the therapeutic efficacy of radiotherapy for glioblastoma (GBM). By using a surface-functionalization of a lipid nanoparticle (LNP) formulation with anti-PD-L1 antibody (αPD-L1), we have established an innovative nano-delivery strategy which enables effective delivery of therapeutics to TAMCs. Current immunotherapy using αPD-L1 as immune checkpoint inhibitor only blocks the functions of the inhibitory ligand without degrading the ligands or eradicating PD-L1 expressing cells, likely limiting the overall therapeutic benefits of the treatment. The knowledge of continuous recycling of PD-L1 suggests that targeting of PD-L1 expressing cells with a payload that could inhibit de novo synthesis of PD-L1 and/or eliminate these immunosuppressive cells would be beneficial in context of anti-glioma treatment. A recent study highlighted the critical role of cyclin-dependent kinase 5 (CDK5) in interferon gamma (IFNy)-stimulated PD-L1 production in tumor cells. Herein, we established a new nano-formulation with encapsulation of dinaciclib (Dina), a small molecule CDK5 inhibitor, into PD-L1-targeting LNPs to create a dual-action system allowing a specific delivery of the therapeutic antibody and drug payloads to PD-L1 expressing TAMCs, which enabled synergistic inhibition of PD-L1 through neutralization of expressed PD-L1 on cell plasma as well as inhibition of de-novo synthesis of PD-L1 inside cells.

Interestingly, radiation therapy (RT), a standard of care in the treatment of GBM, significantly induced upregulation of PD-L1 on glioma-infiltrating TAMCs, which is considered as an important mechanism of tumor radioresistance. We have demonstrated that the RT-elicited increase in PD-L1 expression further enhanced the targeting efficiency of PD-L1 targeting nanoparticles. Accordingly, an RT combined with our nano-immunotherapy led to dramatically extended survival of tumor-bearing mice in different syngeneic glioma models. The high targeting efficiency of αPD-L1-LNP to human TAMCs isolated from tumor and blood samples of GBM patients further validated the clinical relevance of proposed system. Thus, this study establishes a new therapeutic approach with great potential to improve the clinical response in the treatment of GBM, and warrants a rapid translation into clinical practice.

Example 2—Therapeutic Targeting of Tumor-Associated Myeloid Cells Synergizes with Radiation Therapy for Glioblastoma Reference is made to Zhang et al., "Therapeutic targeting of tumor-associated myeloid cells synergizes with radiation therapy for glioblastoma," PNAS Nov. 19, 2019, vol. 116, no. 47, pages 23714-23723, published online Nov. 11, 2019, the content of which is incorporated herein by reference in its entirety.

Abstract

Tumor-associated myeloid cells (TAMCs) are a key driver of immunosuppression in the tumor microenvironment, which profoundly impedes the clinical response to immune-dependent and conventional therapeutic modalities. As a hallmark of glioblastoma (GBM), TAMCs are massively recruited to reach up to 50% of the brain tumor mass. Thereby, they have recently been recognized as an appealing therapeutic target to blunt immunosuppression in GBM with the hope to maximize the clinical outcome of antitumor therapies. Here we report a nano-immunotherapy approach capable of actively targeting TAMCs in vivo. As we found that PD-L1 is highly expressed on glioma-associated TAMCs, we rationally designed a lipid nanoparticle (LNP) formulation surface-functionalized with anti-PD-L1 therapeutic antibody (αPD-L1). We demonstrated that this system (αPD-L1-LNP) enabled effective and specific delivery of therapeutic payload to TAMCs. Specifically, encapsulation of dinaciclib, a cyclin-dependent kinase inhibitor, into PD-L1-targeted LNP led to a robust depletion of TAMCs, and an attenuation of their immunosuppressive functions. Importantly, the delivery efficiency of PD-L1-targeted LNP was robustly enhanced in the context of radiation therapy (RT) owing to the RT-induced upregulation of PD-L1 on glioma-infiltrating TAMCs. Accordingly, an RT combined with our nano-immunotherapy led to dramatically extended survival of mice in two syngeneic glioma models, GL261 and CT2A. The high targeting efficiency of αPD-L1-LNP to human TAMCs isolated from GBM patients further validated the clinical relevance. Thus, this study establishes a new therapeutic approach with immense potential to improve the clinical response in the treatment of GBM, and warrants a rapid translation into clinical practice.

Significance Statement

Tumor-associated myeloid cells (TAMCs) are a key driver of immunosuppression and therapy resistance in glioblastoma (GBM), the deadliest malignant brain tumors. The fact that TAMCs compose up to 50% of the brain tumor mass further highlights the urgent need to develop therapeutic strategy for effective targeting of TAMCs in GBM. Here we report a lipid nanoparticle (LNP) platform capable of actively targeting and delivering therapeutics to mouse and human TAMCs by recognizing highly expressed PD-L1 on TAMCs. We show that LNP encapsulated with dinaciclib robustly eliminated TAMCs from glioma, and significantly extended survival of mice in glioma models as combination with radiation therapy. This nanomedicine platform holds great potential for improved treatment of GBM and rapid translation into clinical practice.

Introduction

Compelling clinical findings in cancer immunotherapy have sparked profound hope and opened up a new era of cancer treatment. Specific targeting of immune cell populations has emerged as a promising therapeutic approach to reactivate antitumor immune response in several human and mouse tumor models (1-3). Indeed, the greatest success to date has been achieved in manipulating and engineering antitumor effector cells, particularly tumor-infiltrating T lymphocytes (4-6). However, mounting evidence has also emphasized the vital role of the immunosuppressive network in promoting therapy tolerance, which must be overcome to unleash the full power of antitumor immunity (7). As a major component of the solid tumor microenvironment (TME), immunosuppressive cells are recruited by tumor cells to evade immune surveillance, which profoundly influence the overall therapeutic outcome of both immune-dependent and conventional therapeutic modalities (8-11). That is especially true in the treatment of glioblastoma (GBM), the most common and deadliest malignant brain tumors in adults (12-14), which is largely attributed to its highly aggressive and immunosuppressive features (15, 16). There is an urgent need to develop new therapeutics actively targeting immunosuppressive cells to modulate the TME in GBM in hopes to maximize the clinical response of existing anti-tumor therapies.

Tumor-associated myeloid cells (TAMCs) are a major driver of immunosuppression in GBM (16-18). TAMCs are a heterogeneous population of myeloid cells originating from hematopoietic precursors, including tumor-associated macrophages (TAMs) and myeloid-derived suppressor cells (MDSCs), which are morphologically and phenotypically distinct, but share a functional commonality of strongly inhibiting both innate and adaptive immunity (19-21). Notably, they are a hallmark of GBM, as TAMCs account for a predominant population of immune cells at the tumor site, comprising 30%-50% of the tumor mass (22-24). These immunosuppressive cells dramatically impair antitumor immunity by suppressing function of immune effector cells through multiple pathways, including deprivation of nutrients essential for lymphocytes, generation of oxidative stress, and induction/recruitment of regulatory T cells (Tregs) (21).

Mechanistically, accumulating research has highlighted the functional importance of programmed death-ligand 1 (PD-L1) as an essential mechanism of immunosuppressive functions of TAMCs to impair the antitumor activity of T cells (25-27). TAMCs have recently been demonstrated to much more profoundly express PD-L1 over other subsets of immune cells, and even tumors themselves (25, 28). Interestingly, although PD-L1 has drawn considerable attention as a therapeutic target in immune checkpoint blockade therapy, it has been rarely employed as a targeted moiety for therapeutic delivery to PD-L1 expressing cells as tumor cells, which might be due to the lack of evidence to show binding of ligand to PD-L1 could promptly activate transmembrane transport mechanisms in those cells. However, the inherent phagocytic functions and scavenging capabilities of the $CD11b^+$ myeloid lineage cells (e.g., TAMCs) (29) raises the possibility that active binding of nanoparticles to highly expressed PD-L1 on such cells could be a novel and feasible approach to trigger active uptake of nanoparticles for targeted therapeutic delivery to TAMCs.

Here we describe a nano-immunotherapy approach capable of actively targeting TAMCs in vivo to blunt the immunosuppression in GBM (FIG. 1A). We hypothesized that surface functionalization of a lipid nanoparticle (LNP) formulation with anti-PD-L1 antibody (αPD-L1) might enable effective delivery of LNP-encapsulated therapeutics to TAMCs. Current immunotherapy using αPD-L1 as immune checkpoint inhibitor only blocks the functions of the inhibitory ligand without degrading the ligands or eradicating PD-$L1^+$ cells, likely limiting the overall therapeutic benefits of the treatment. The knowledge of continuous recycling of PD-L1 (30) suggests that targeting of PD-$L1^+$ cells with a payload that could inhibit de novo synthesis of PD-L1 and/or eliminate these immunosuppressive cells would be beneficial in context of anti-glioma treatment. A recent study highlighted the critical role of cyclin-dependent kinase 5 (CDK5) in interferon gamma (IFNγ)-stimulated PD-L1 production in tumor cells (31). In this work, we demonstrated that treatment of TAMCs with dinaciclib (Dina), a small molecule CDK5 inhibitor, effectively attenuated PD-L1 expression on TAMCs at a dose as low as 25 nM and induced an apoptosis of TAMCs at higher dose. Encapsulation of Dina into PD-L1-targeting LNPs created a dual-action system allowing a specific delivery of the therapeutic antibody and drug payloads to PD-L1 expressing TAMCs. Local intracranial treatment with this system resulted in robust TAMC depletion and attenuation of their immunosuppressive functions.

Interestingly, radiation therapy (RT), a standard of care in the treatment of GBM, induced upregulation of PD-L1 in glioma-infiltrating TAMCs, which is considered as an important mechanism of tumor radio-resistance. Here we demonstrated that the RT-elicited increase in PD-L1 expression further enhanced the targeting efficiency of PD-L1 targeting nanoparticles. Accordingly, an RT combined with our nano-immunotherapy led to dramatically extended survival of tumor-bearing mice in two different syngeneic glioma models, GL261 and CT2A. The high targeting efficiency of αPD-L1-LNP to human TAMCs isolated from tumor and blood samples of GBM patients further validated the clinical relevance of proposed system. Thus, this study establishes a new therapeutic approach with great potential to improve the clinical response in the treatment of GBM, and warrants a rapid translation into clinical practice.

Results

Engineering of LNPs targeted to glioma-associated TAMCs. Our first step was to identify a receptor that is highly expressed on TAMCs over other subsets of immune cells, which could be readily recognized by the complementary ligand functionalized on nanoparticles. Emerging evidence indicated that PD-L1 is overexpressed on myeloid lineage in several tumor models (25, 32). Herein we comprehensively analyzed an array of tumor-infiltrating immune cells in GL261 synergic mouse glioma model. Flow cytometric analysis revealed a PD-L1 expression by several immune cell subsets with a profound overexpression on TAMCs. Particularly, monocytic MDSCs (M-MDSCs) showed the highest expression of PD-L1, followed by TAMs and polymorphonuclear MDSCs (PMN-MDSCs), as judged by percentage of PD-L1 positive cells (FIG. 1B) and mean fluorescence intensity (MFI) (FIG. 1C). These data suggest that PD-L1 might be a viable targeted molecule for specific therapeutic delivery to glioma-associated TAMCs.

Figure 2:
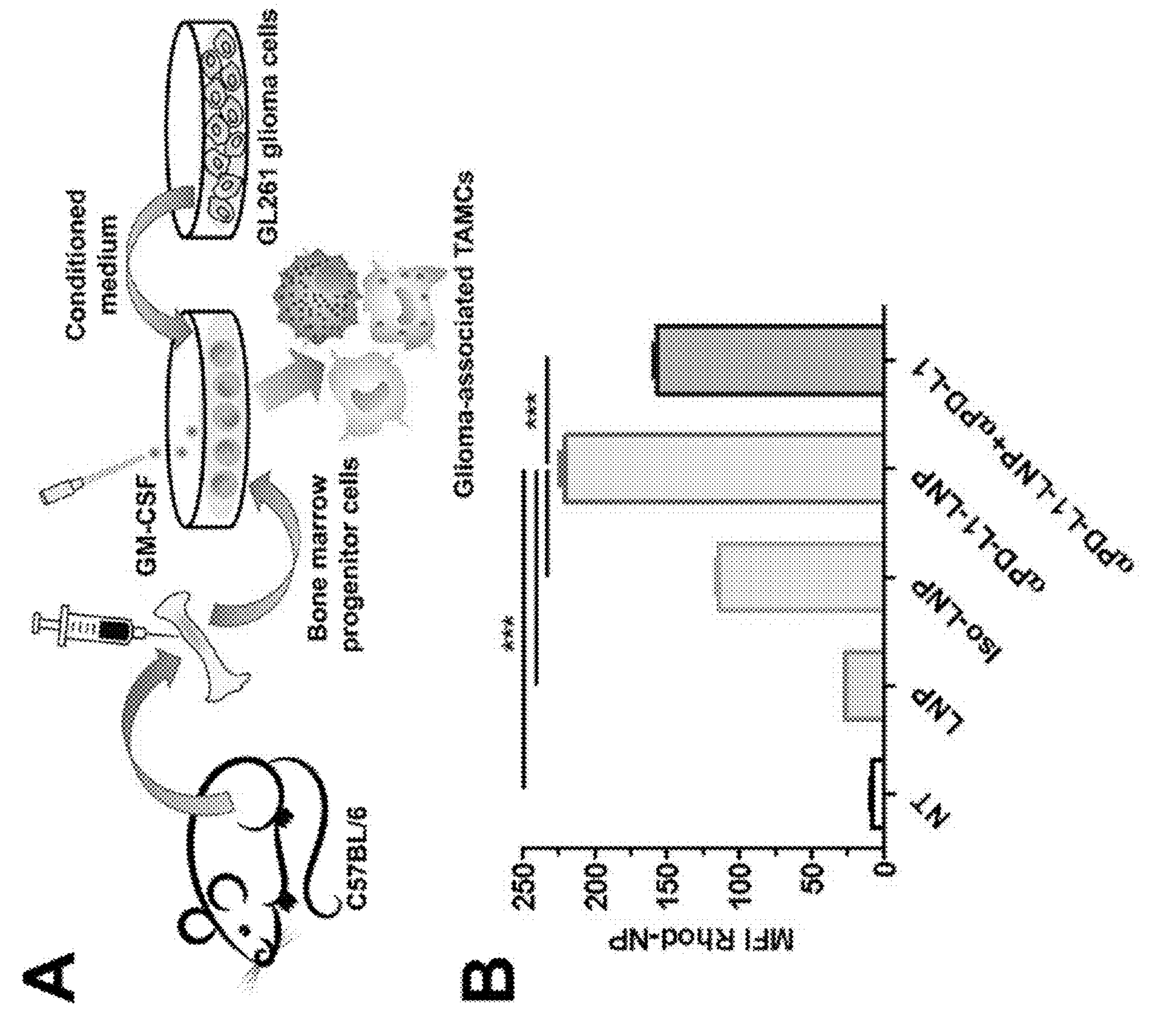
FIG. 2. αPD-L1-LNPs effectively target in vitro generated TAMC and impair PD-L1 recycling. (A) Schematic of in vitro generation of GL261 glioma-associated TAMCs. (B) Flow cytometric quantification of cellular binding of Rhod-PE labeled LNPs in TAMCs after 1 h of binding at 4° C. (C) Fluorescence microscopy images of cellular uptake of Rhod-PE labeled LNPs by TAMCs after 1 h of incubation at 37° C. Scale bar, 50 μm. (D) Intracellular trafficking of Rhod-PE labeled αPD-L1-LNPs in TAMCs after 1 h of incubation at 37° C. Cell membrane was stained by WGA, lysosome was stained by Lyso-Tracker DND26, and cell nucleus was stained by NucBlue. Scale bar, 50 μm. (E) Flow cytometric analysis of cellular uptake of Rhod-PE labeled LNPs within a co-culture of TAMCs and GL261 glioma cells after 1 h and 4 h of incubation. (F) Schematic of PD-L1 internalization and recycling assay. (G-H) Flow cytometric analysis of cell surface PD-L1 (G) and cell surface-bound αPD-L1 (H). Cells were treated with unconjugated αPD-L1 or αPD-L1-LNP, and collected after binding at 4° C. or subsequent incubation at 37° C. to allow internalization and recycling. Primaquine (PM) was used as recycling inhibitor. Data are represented as mean±SEM; n=3; *, $p<0.05$; ***, $p<0.001$; n.s., not significant; determined by one-way ANOVA (in B, G, and H) or two-way ANOVA (in E) with Tukey's multiple comparisons test.
Figure 2:
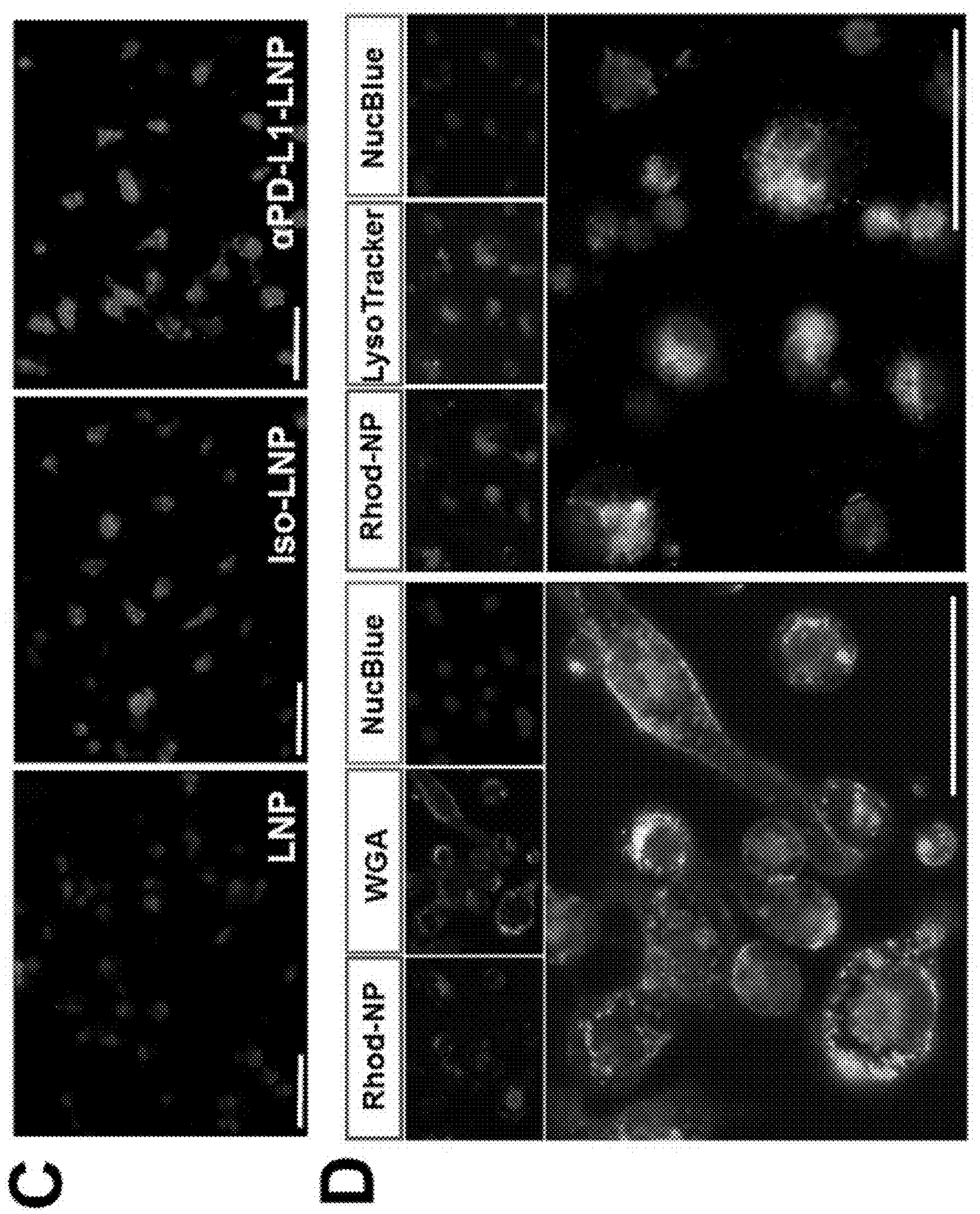
Figure 2:
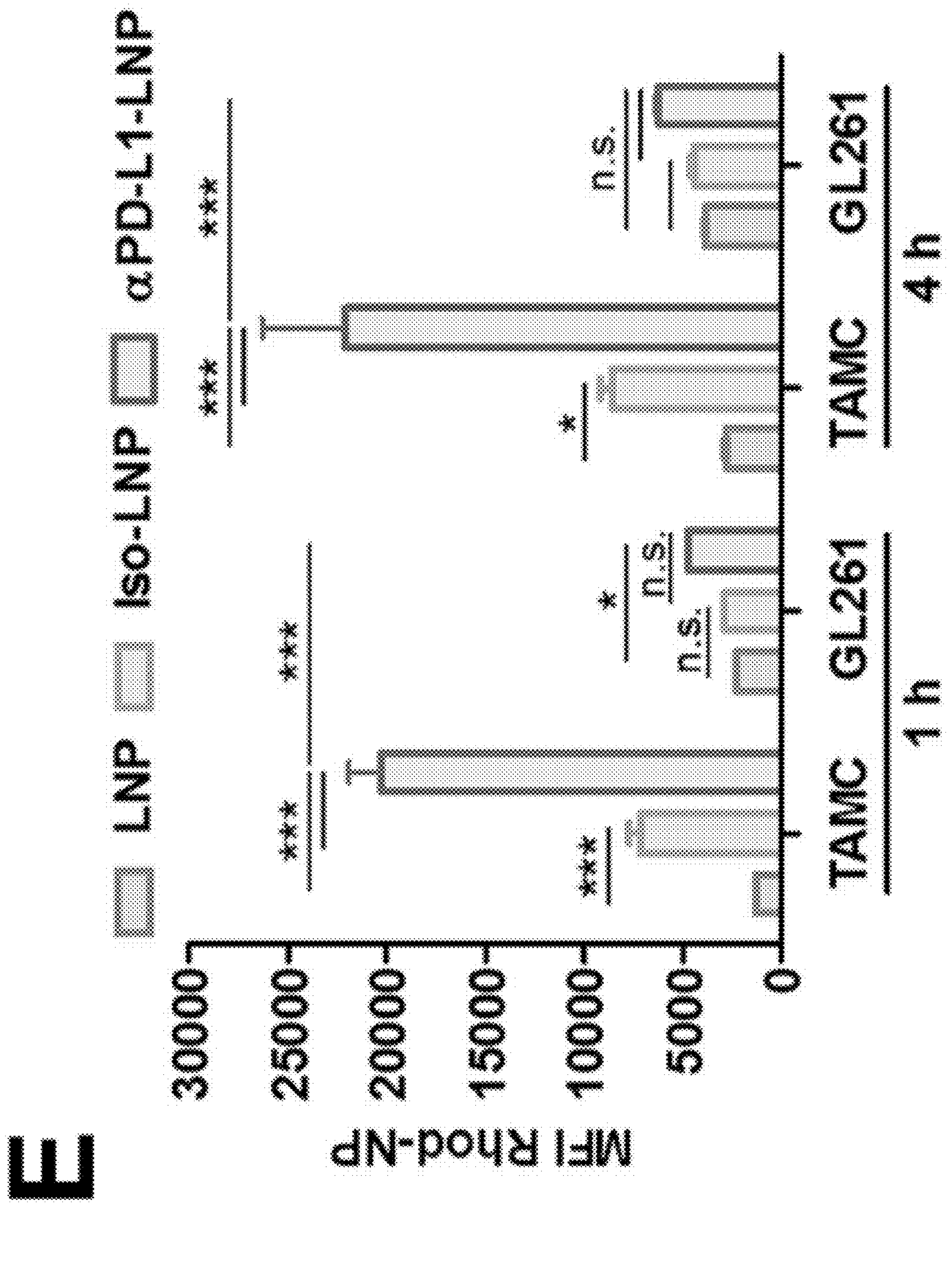
Figure 2:
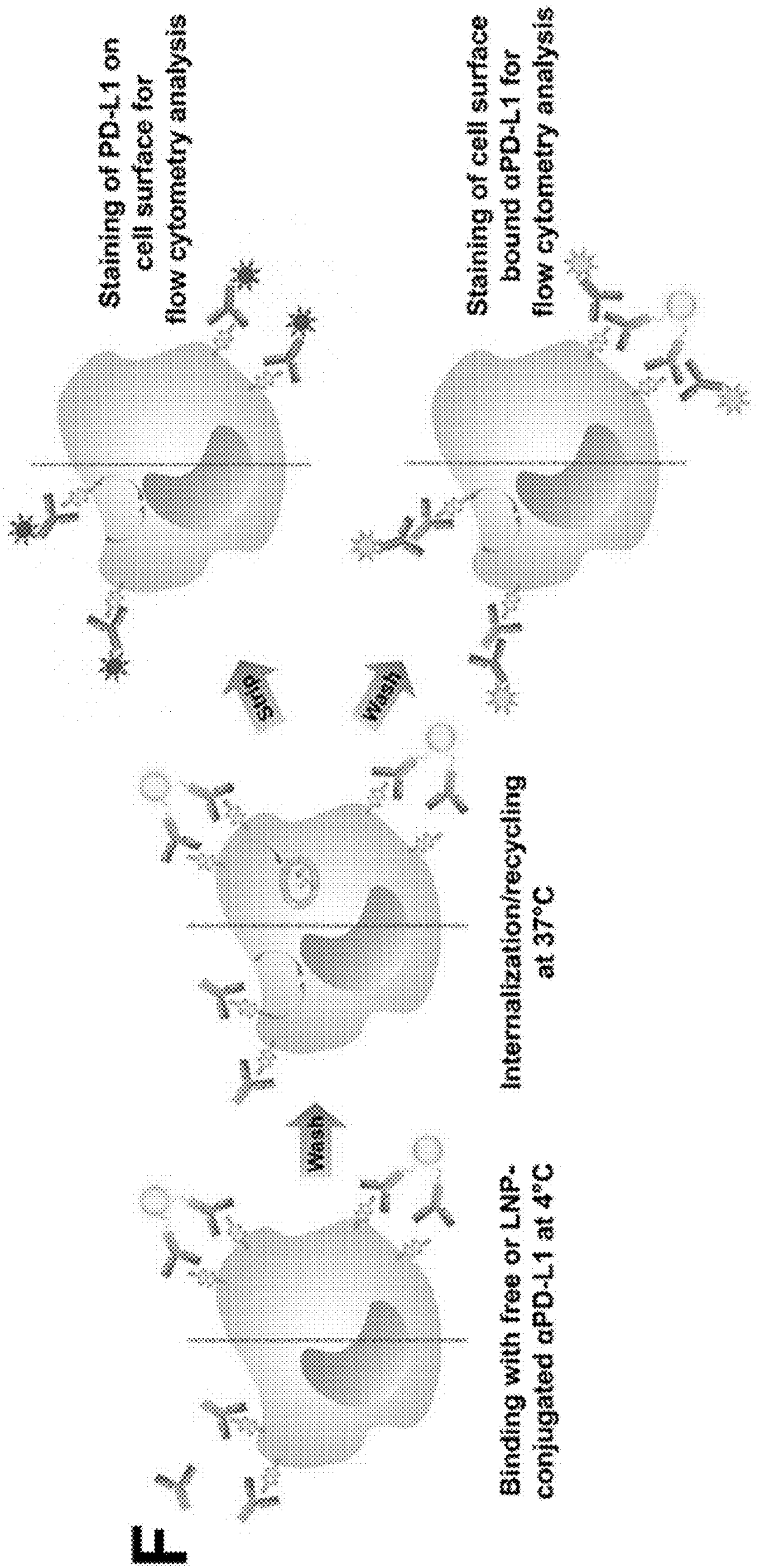
Figure 2:
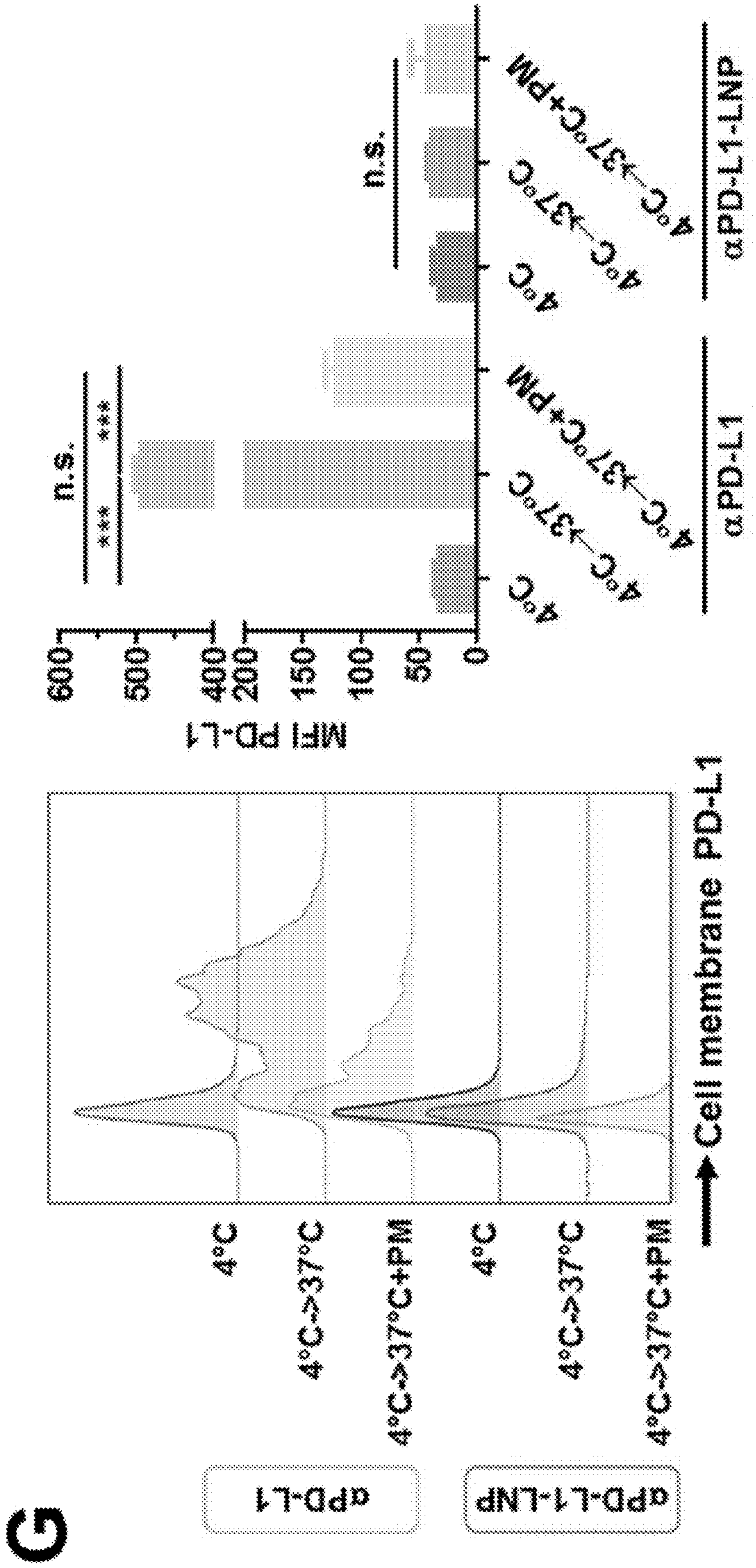
Figure 2:
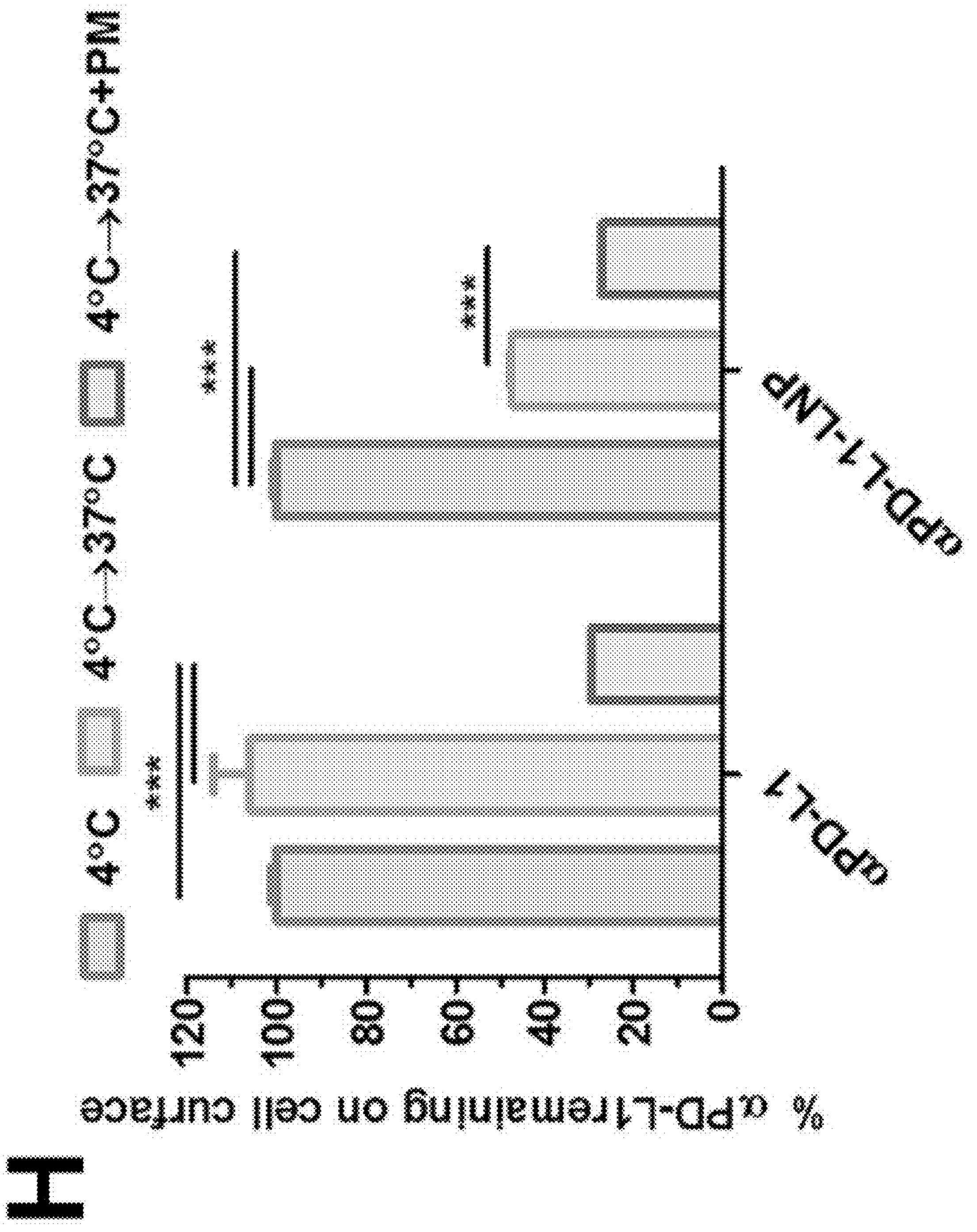
Figure 8:
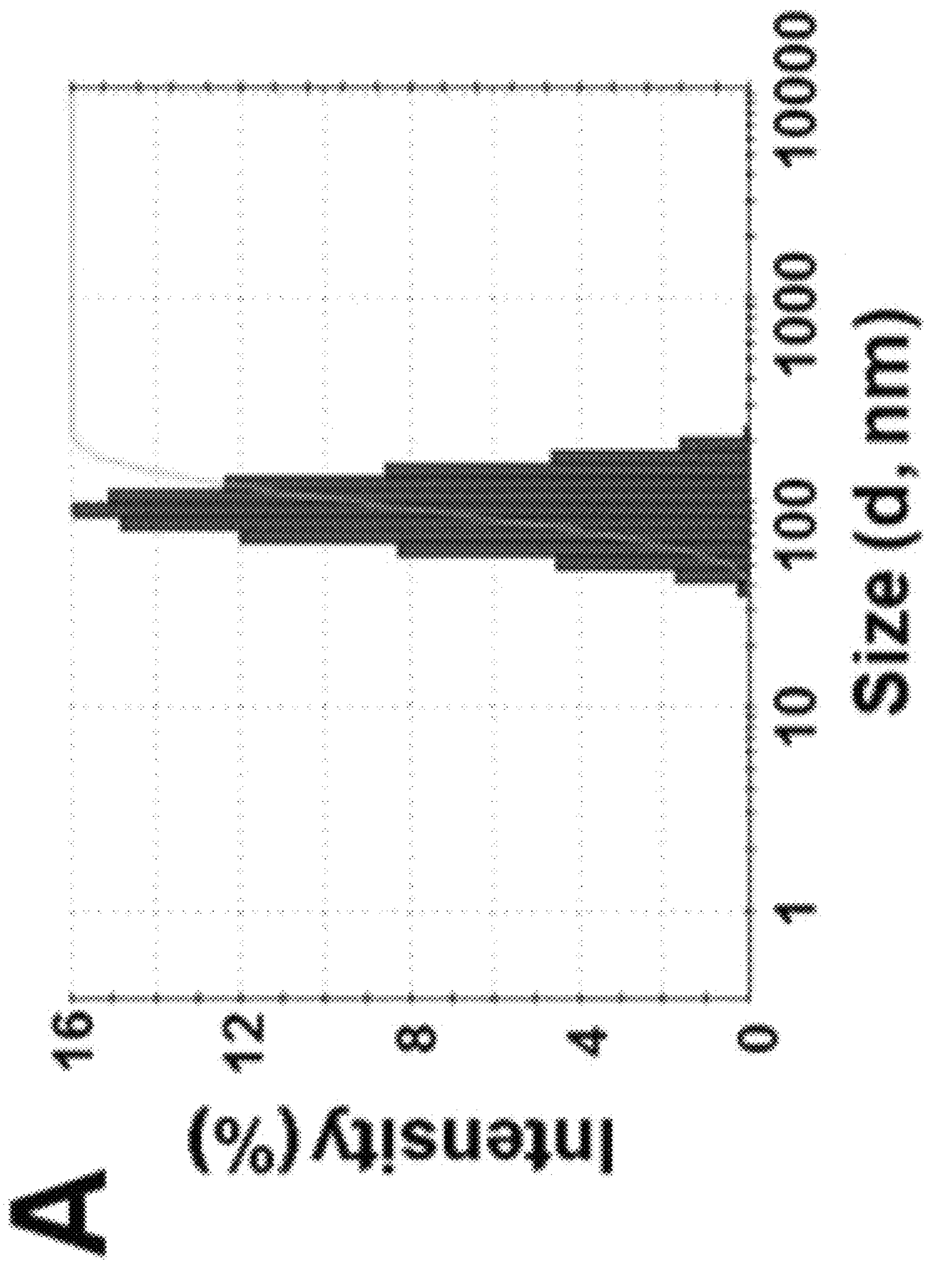
FIG. 8. Measurement of particle size distribution of LNP (A) and αPD-L1-LNP (B) by DLS.
Figure 8:
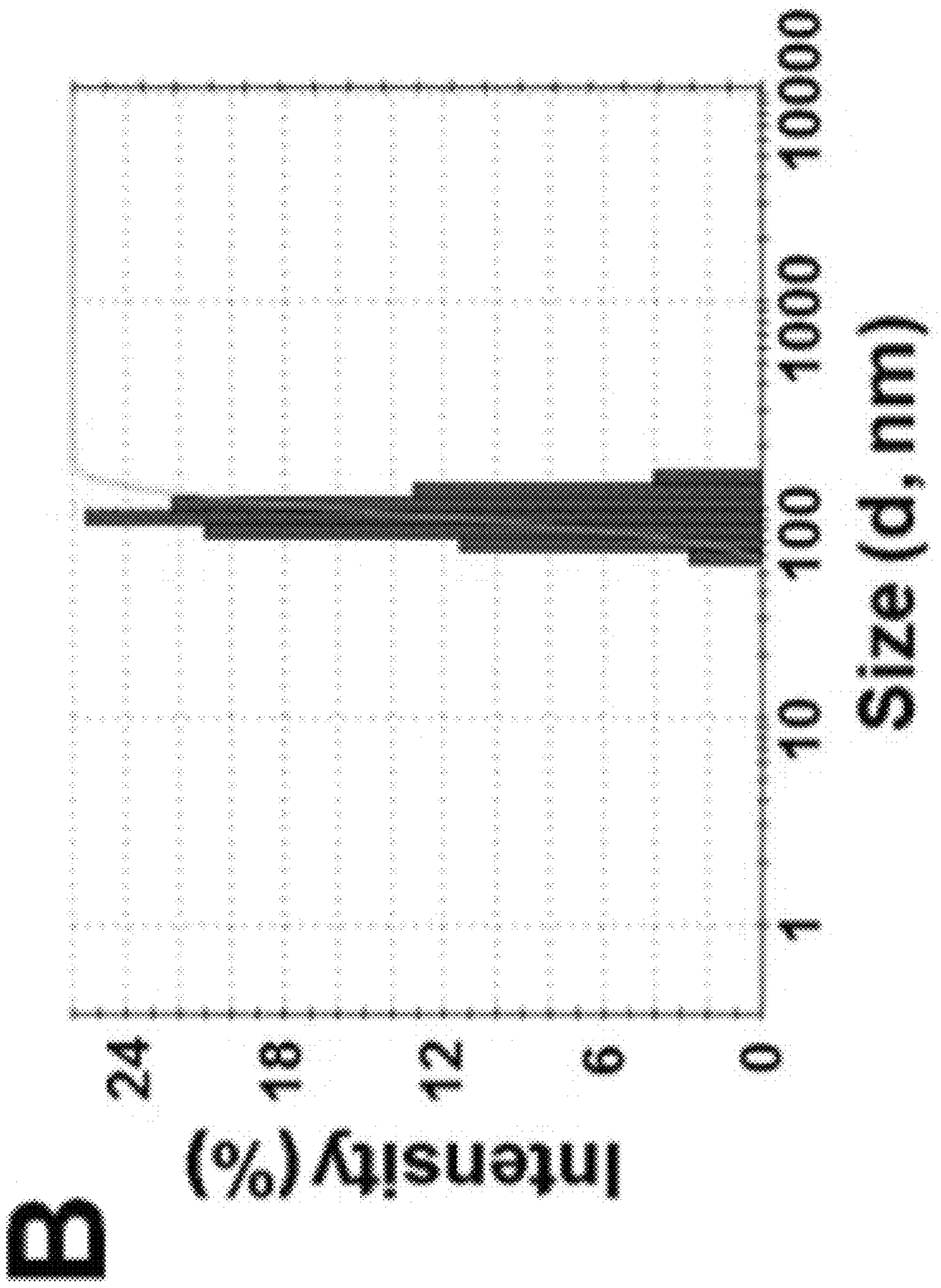
Figure 9:
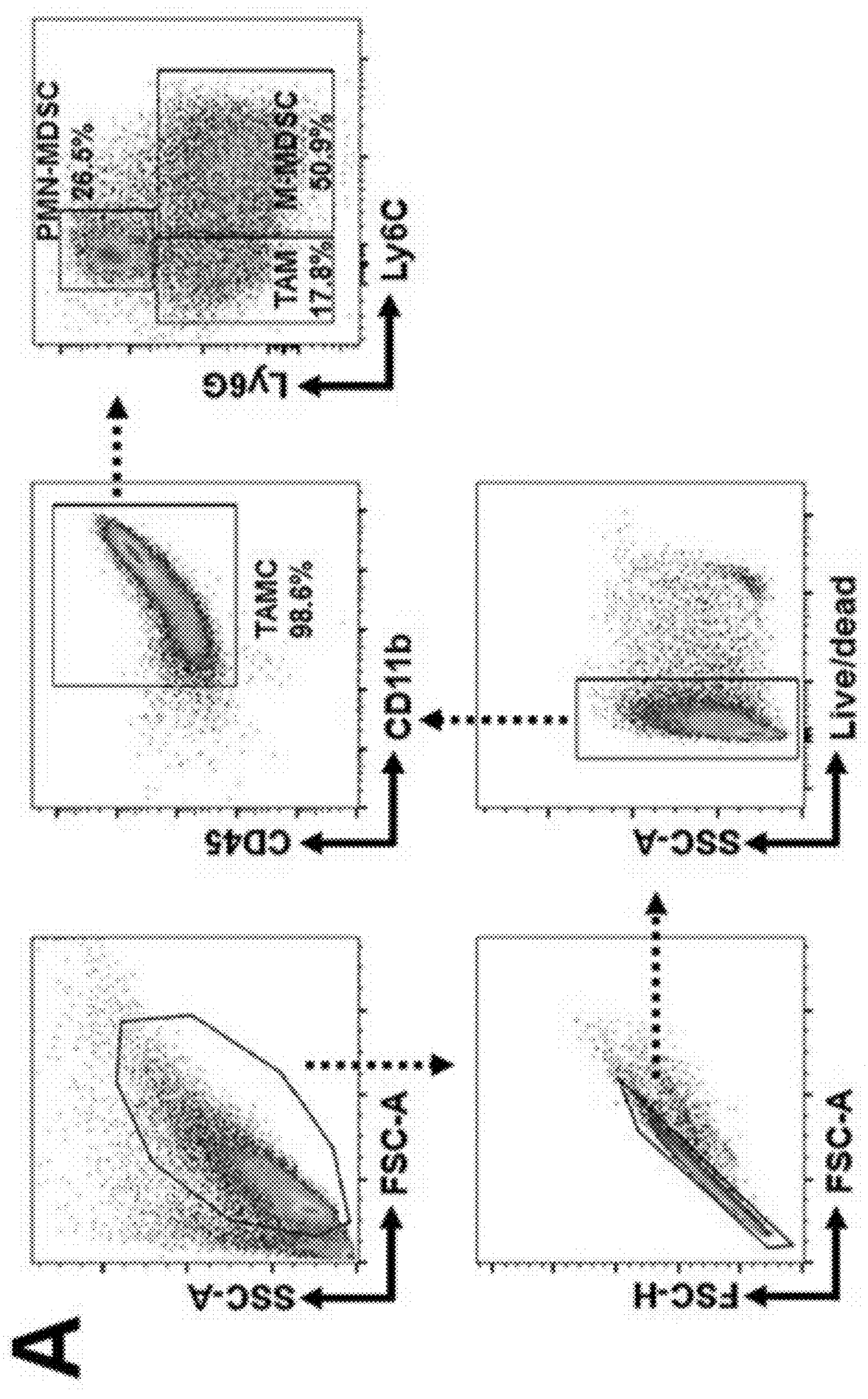
FIG. 9. Phenotyping of in vitro generated GL261-associated TAMCs. Subsets (A) and PD-L1 expression (B) on TAMCs generated in vitro from bone marrow progenitor cells were analyzed by flow cytometry.
Figure 9:
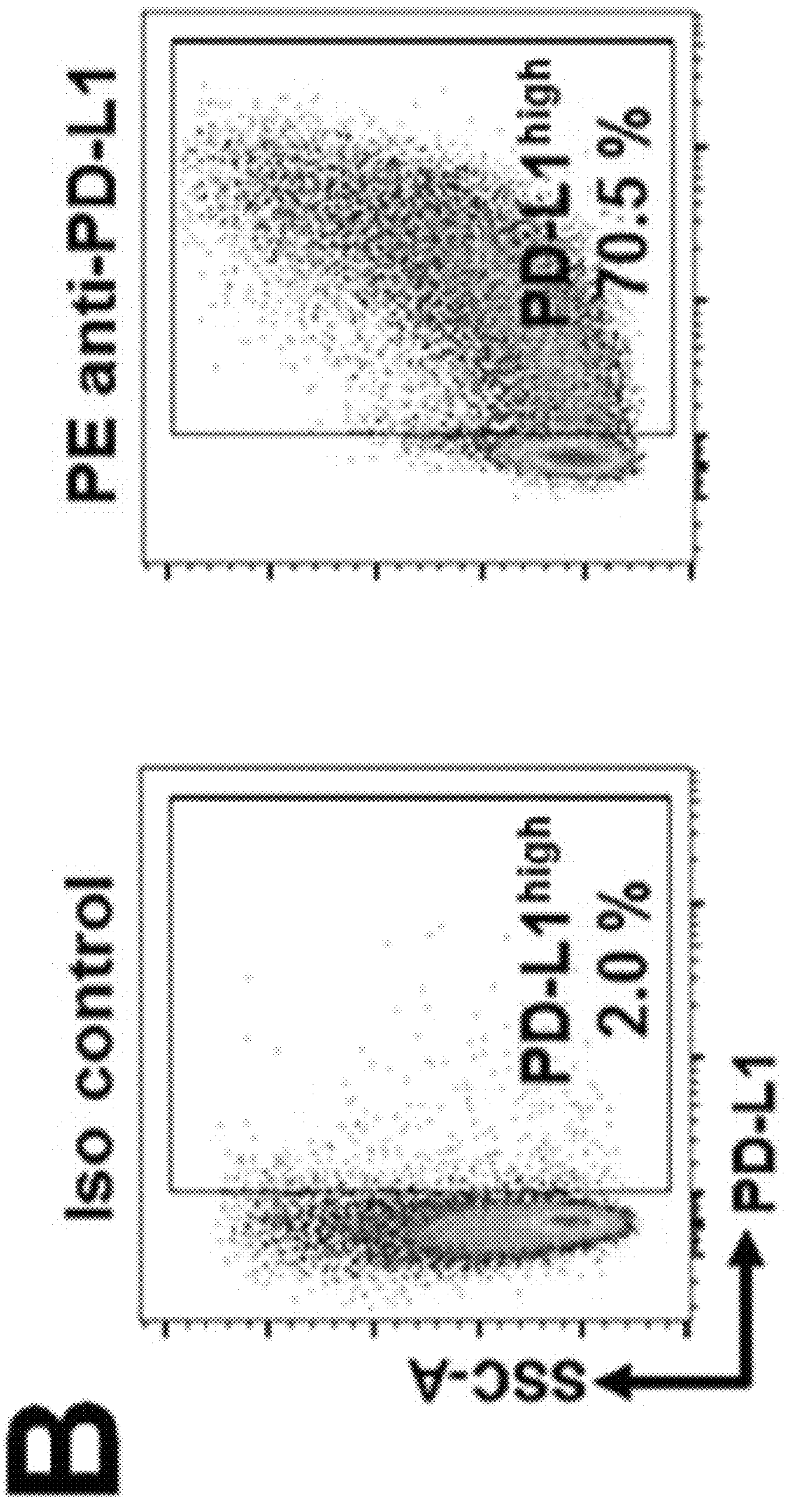
Figure 10:
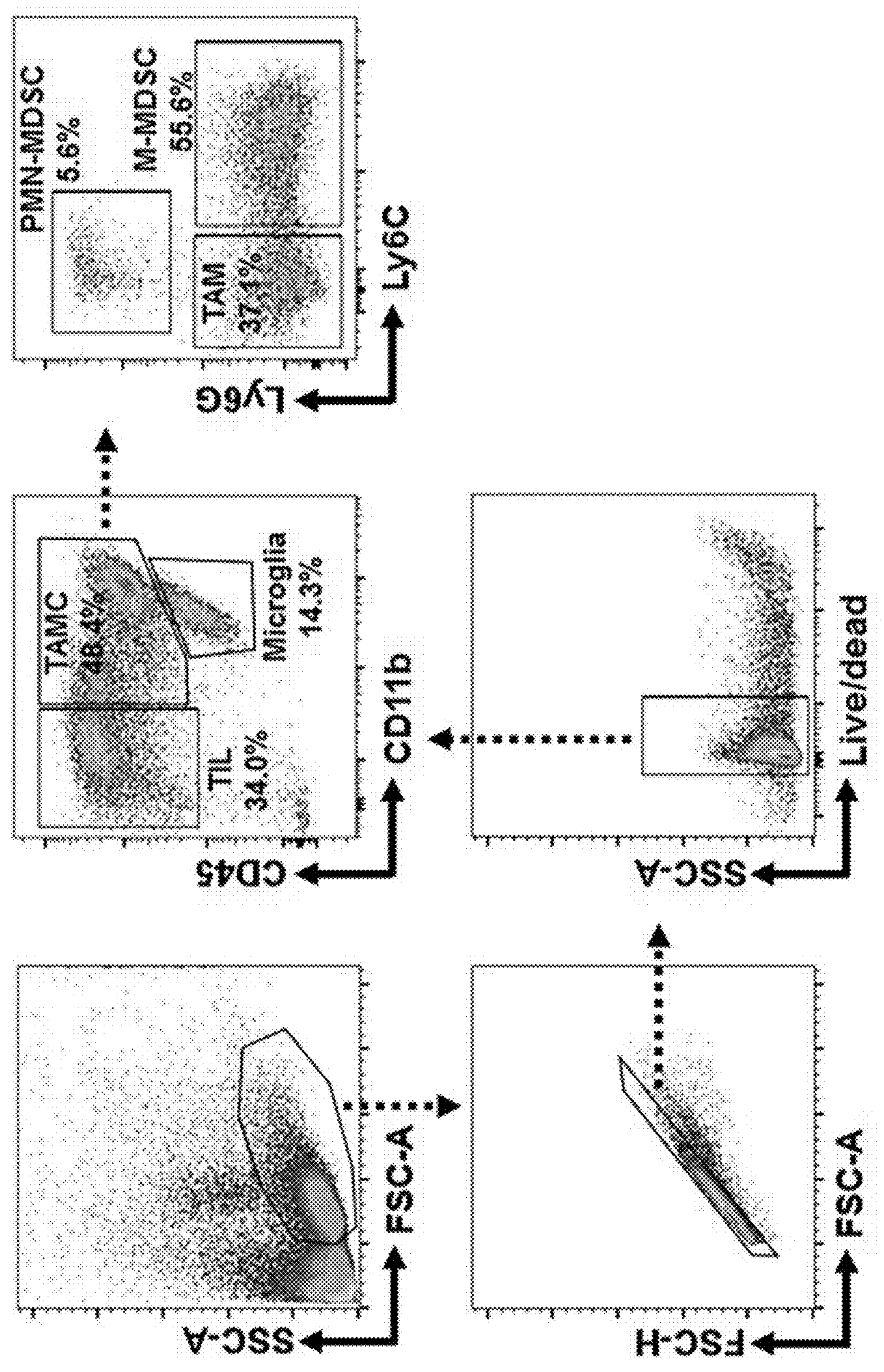
FIG. 10. TAMC subsets in a GL261 glioma model. Subsets of tumor-infiltrating TAMCs in the brain of GL261 glioma bearing mice were analyzed by flow cytometry.

Next, we designed a system allowing for simultaneous and specific drug and antibody delivery to TAMCs. A lipid-based nanoparticle formulation was prepared (FIG. 1A). DOPC, cardiolipin, and cholesterol are three components which constitute the hydrophobic membrane with phospholipid bilayer structure, in which the small hydrophobic molecule Dina can be well accommodated. The surface of formed LNPs was engineered with DSPE-$PEG_{2000}$ to provide high aqueous solubility and formulation stability. The corona of LNPs was then functionalized with αPD-L1 through conjugation with the terminal maleimide group of DSPE-$PEG_{2000}$. Cyro-EM images illustrate the spherical morphology of nanoparticles with diameter below 100 nm, and the surface coupled monoclonal antibodies (mAbs) (FIG. 1D, upper panels). Dynamic light scattering (DLS) demonstrates a particle size distribution of the αPD-L1 functionalized lipid nanoparticles (αPD-L1-LNP) around 90 nm in diameter, only slightly larger than non-modified LNPs (FIG. 1D, lower panels and FIG. 8). Zeta-potential analysis indicates a slightly negatively charged surface of nanoparticles.

αPD-L1-functionalized LNPs demonstrate a high avidity and specificity to glioma-associated TAMCs and impair recycling of PD-L1 in TAMCs. As an initial step to evaluate if surface conjugation of αPD-L1 could be an efficacious approach to target the therapeutic delivery to TAMCs, we generated glioma-associated TAMCs in vitro as our test system, as depicted in FIG. 2A. The in vitro generated TAMCs showed a high purity and highly expressed PD-L1 (FIG. 9), among which M-MDSCs were more prevalent over PMN-MDSCs, which is consistent with the in vivo phenotyping of GL261 glioma model (FIG. 10). αPD-L1-LNPs demonstrated high binding to TAMCs, traced by Rhod-PE labeled phospholipids, as compared to IgG isotype control conjugated LNP (Iso-LNP) as well as LNP without mAb decoration (FIG. 2B). In our experiments, all cells were pre-incubated with Fc receptor binding inhibitors to block non-specific binding of αPD-L1 to myeloid cells. Importantly, the enhancement in the cellular binding of αPD-L1-LNPs was significantly impeded by pre-blocking of TAMCs with excess amount of free αPD-L1 mAbs (FIG. 2B), further validating that the targeting of LNPs was largely mediated by surface interaction of αPD-L1 and PD-L1 on TAMCs.

To confirm if PD-L1 mediated surface binding could effectively trigger internalization of nanoparticles into TAMCs, we tracked the cellular uptake and intracellular distribution of nanoparticles in TAMCs. FIG. 2C shows a more robust accumulation of αPD-L1-LNPs in TAMCs after only one hour of incubation at 37° C., and the intracellular distribution of αPD-L1-LNPs was further indicated by wheat germ agglutinin (WGA) cell membrane staining and NucBlue cell nucleus staining (FIG. 2D, left panel). Moreover, Lyso-Tracker staining demonstrated a high co-localization of αPD-L1-LNPs with lysosomes, suggesting that binding of αPD-L1-LNPs to PD-L1 on TAMCs efficiently and promptly triggered nanoparticle internalization through endocytosis/phagocytosis pathway in myeloid cells (FIG. 2D, right panel).

Figure 11:
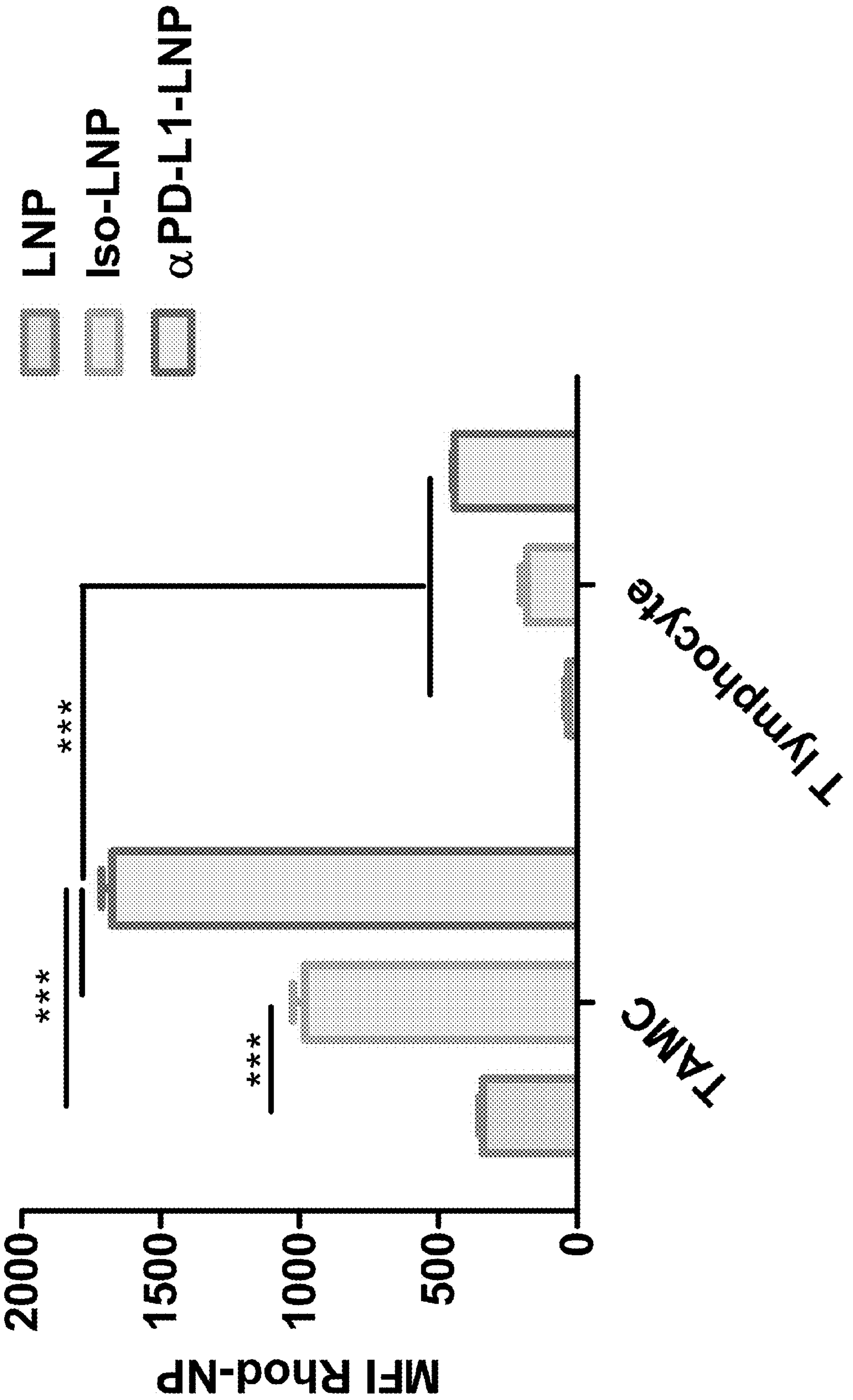
FIG. 11. Flow cytometric analysis of cellular uptake of Rhod-PE labeled LNPs within a co-culture of TAMCs and T cells. Data are represented as mean±SEM; n=3; ***$p<0.001$; determined by two-way ANOVA with Tukey's multiple comparisons test.
Figure 12:
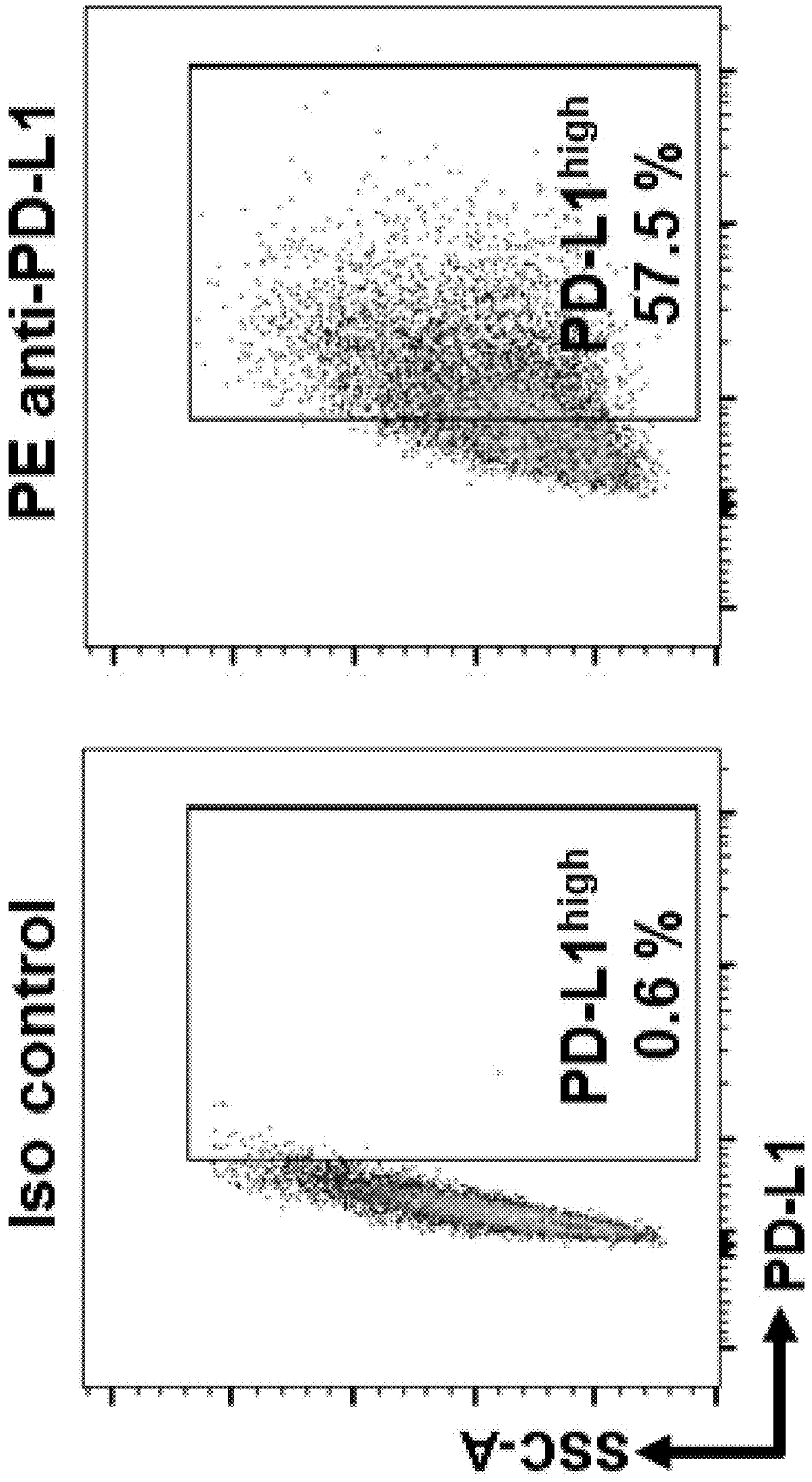
FIG. 12. Flow cytometric analysis of PD-L1 expression on GL261 glioma cells.

To further demonstrate the preferential uptake of αPD-L1-LNPs by TAMCs over T cells expressing PD-L1 at lower levels, we analyzed the interactions of αPD-L1-LNPs in a co-culture of TAMCs and T lymphocytes. Not surprisingly, owing to a higher expression of PD-L1 and phagocytic activity, TAMCs exerted dramatically stronger capability to engulf αPD-L1-LNPs as indicated by flow cytometry analysis, whereas T cells showed a minimal ability (FIG. 11). More importantly, we also evaluated the interactions of αPD-L1-LNPs in a co-culture of TAMCs and GL261 glioma cells, since PD-L1 is also well known expressed on tumor cells (FIG. 12). Interestingly, decoration by αPD-L1 did not elicit robust enhancement in targeting efficiency of LNP to GL261 glioma cells, which showed much lower cellular uptake of αPD-L1-LNPs than TAMCs (FIG. 2E). Altogether, these data strongly indicate the high avidity and specificity of αPD-L1-functionalized LNPs towards glioma-associated TAMCs.

Figure 13:
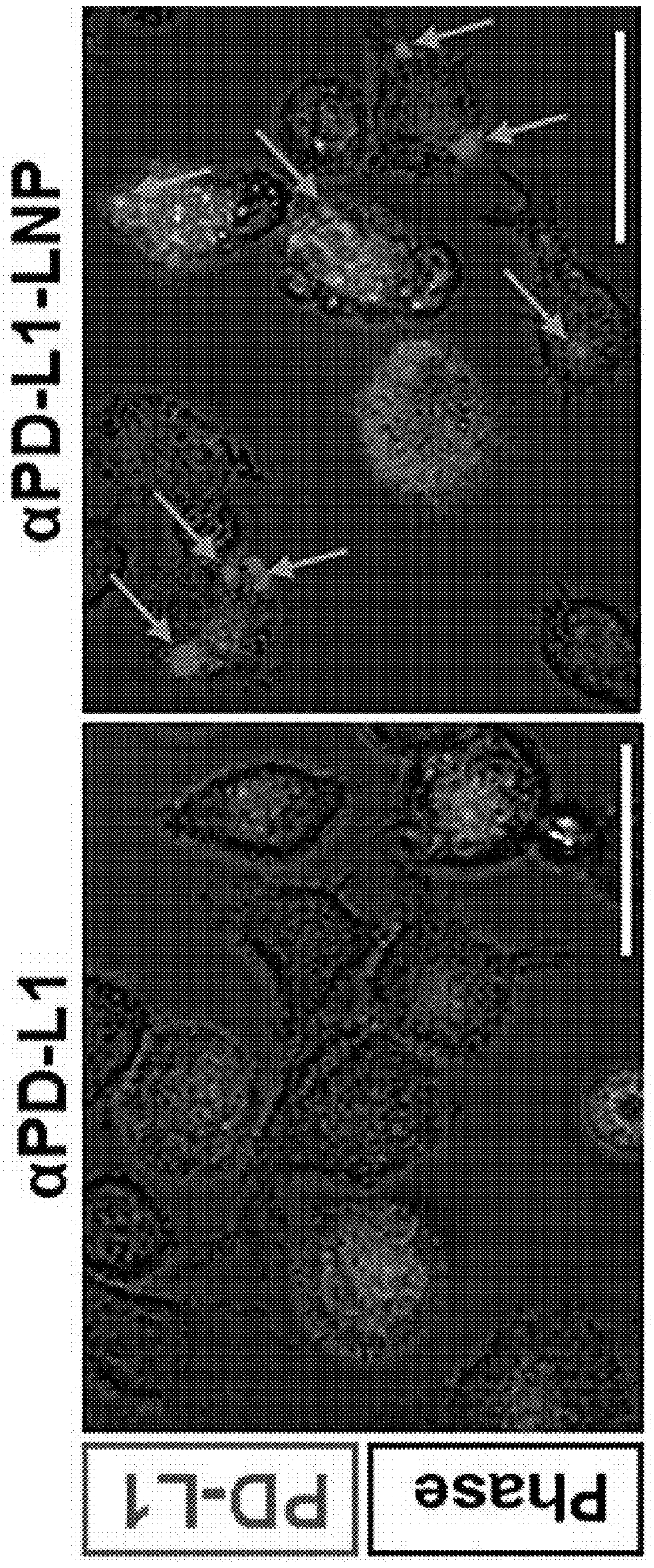
FIG. 13. Clustering of PD-L1 on the cell surface of TAMCs. Cells were incubated with unconjugated αPD-L1 or αPD-L1-LNP at 4° C. for 1 h followed by 37° C. for 15 min. The distribution of PD-L1 on the cell surface was detected by PE anti-PD-L1 antibody. Scale bar, 30 μm.

The interaction between αPD-L1-LNPs and PD-L1 on the plasma membrane of TAMCs was further assessed, using free unconjugated αPD-L1 as a control (FIG. 2F). An efficient blockade of cell surface PD-L1 on TAMCs was achieved after incubation with αPD-L1-LNP or free αPD-L1 at 4° C. Interestingly, binding of αPD-L1-LNP induced substantial loss of PD-L1 from surface of TAMCs after subsequent incubation at 37° C. to allow internalization, whereas free αPD-L1 treated TAMCs regained a high level of PD-L1 on the cell membrane, which could be largely reduced by a treatment with primaquine (PM), an inhibitor of endocytic recycling (33) (FIG. 2G). These data demonstrate a continuous internalization and recycling of PD-L1 on plasma membrane, and binding with αPD-L1-LNP may substantially impair the recycling pathway of PD-L1. Furthermore, our data suggest αPD-L1-LNP may direct PD-L1 to lysosomal degradation, as evidenced by high lysosomal accumulation of αPD-L1-LNP after only 1 h of incubation (FIG. 2D). In support of this hypothesis, incubation at 37° C. induced a dramatic internalization and thus reduction of cell surface-bound αPD-L1 in αPD-L1-LNP treated TAMCs; however, such reduction was not observed in cells treated with free αPD-L1 (FIG. 2H), which could be recycled back to cell surface with PD-L1 through endocytic recycling (30). This was further evidenced by the substantial loss of cell surface-bound free αPD-L1 in the presence of recycling inhibitor (FIG. 2H). The capability of αPD-L1-LNP to reroute the endocytic/recycling pathway of PD-L1 is yet to be fully understood, but may be due to the clustering of PD-L1 on plasma membrane (FIG. 13) caused by multivalent interactions (34) with LNP-conjugation of antibodies.

Figure 3:
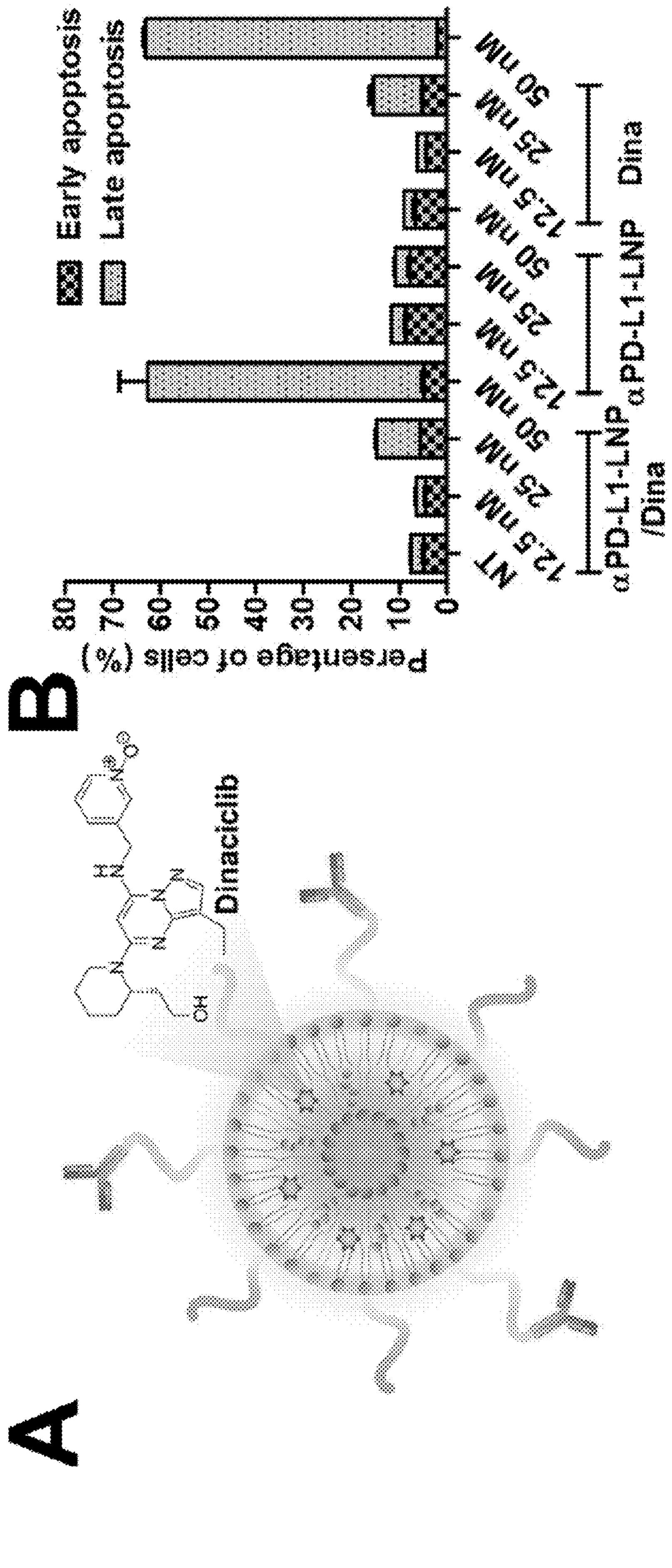
FIG. 3. Therapeutic LNPs effectively impair viability and immunosuppressive activities of TAMCs. (A) Schematic of the chemical structure and LNP-encapsulation of Dina. (B) Annexin v analysis of TAMCs 24 h after treatment of αPD-L1-LNP/Dina, αPD-L1-LNP, or Dina. (C) Expression of PD-L1 on TAMCs 24 h post-stimulation with IFNγ, as determined by RT-qPCR. mRNA levels were normalized to beta-actin and reported relative to control TAMC expression. (D) Flow cytometric analysis of PD-L1 expression on TAMCs 24 h post-stimulation with IFNγ, as presented by MFI. (E) Representative histograms of proliferating CD8$^+$ T cells 72 h after co-cultured with non-treated TAMCs (blue), or 25 nM of αPD-L1-LNP/Dina treated TAMCs (red), as traced by Cell Trace Violet and compared to CD8$^+$ T cells alone (gray shaded region). Data are represented as mean±SEM; n=3; *, $p<0.05$; ***, $p<0.001$; determined by one-way ANOVA with Tukey's multiple comparisons test.
Figure 3:
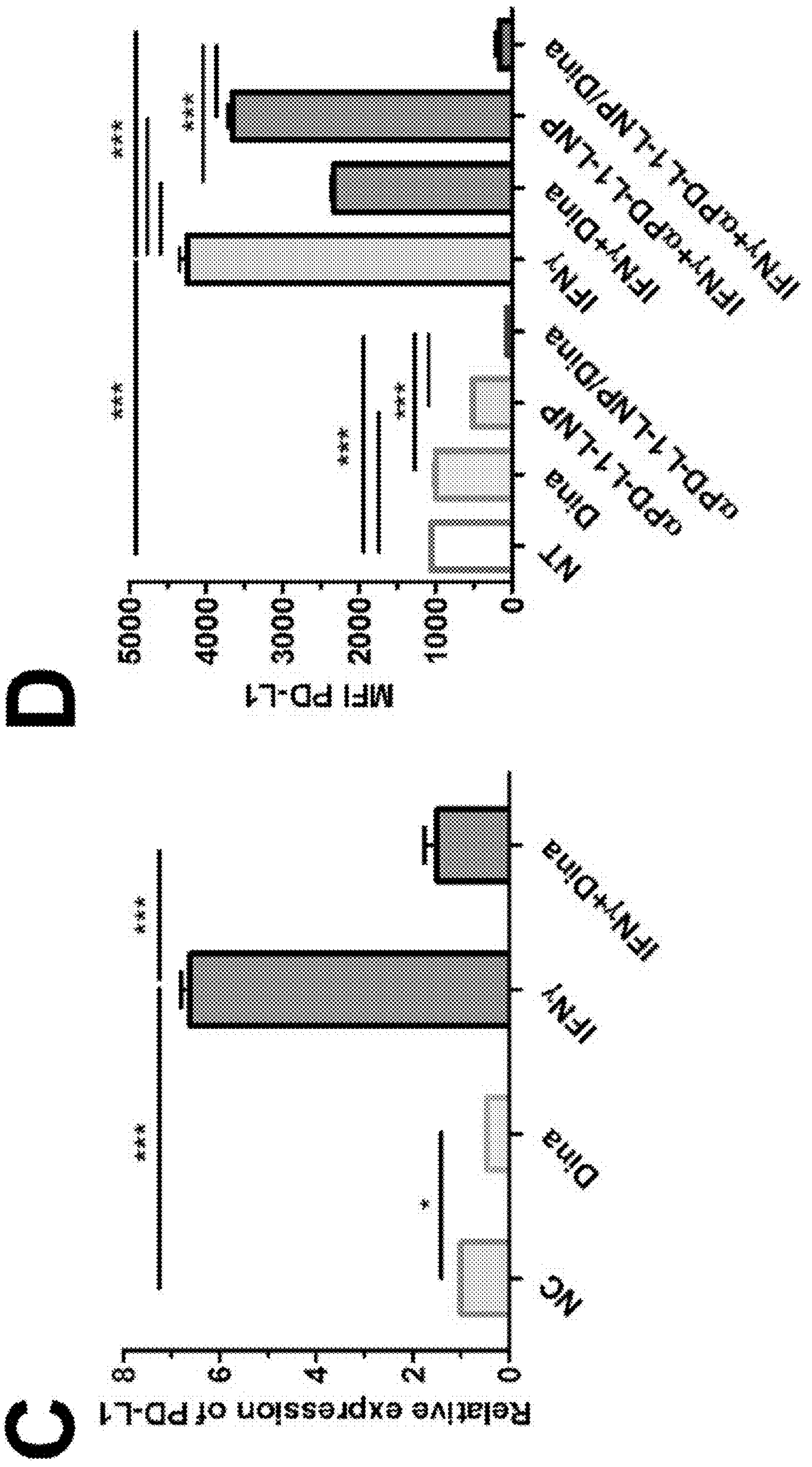
Figure 3:
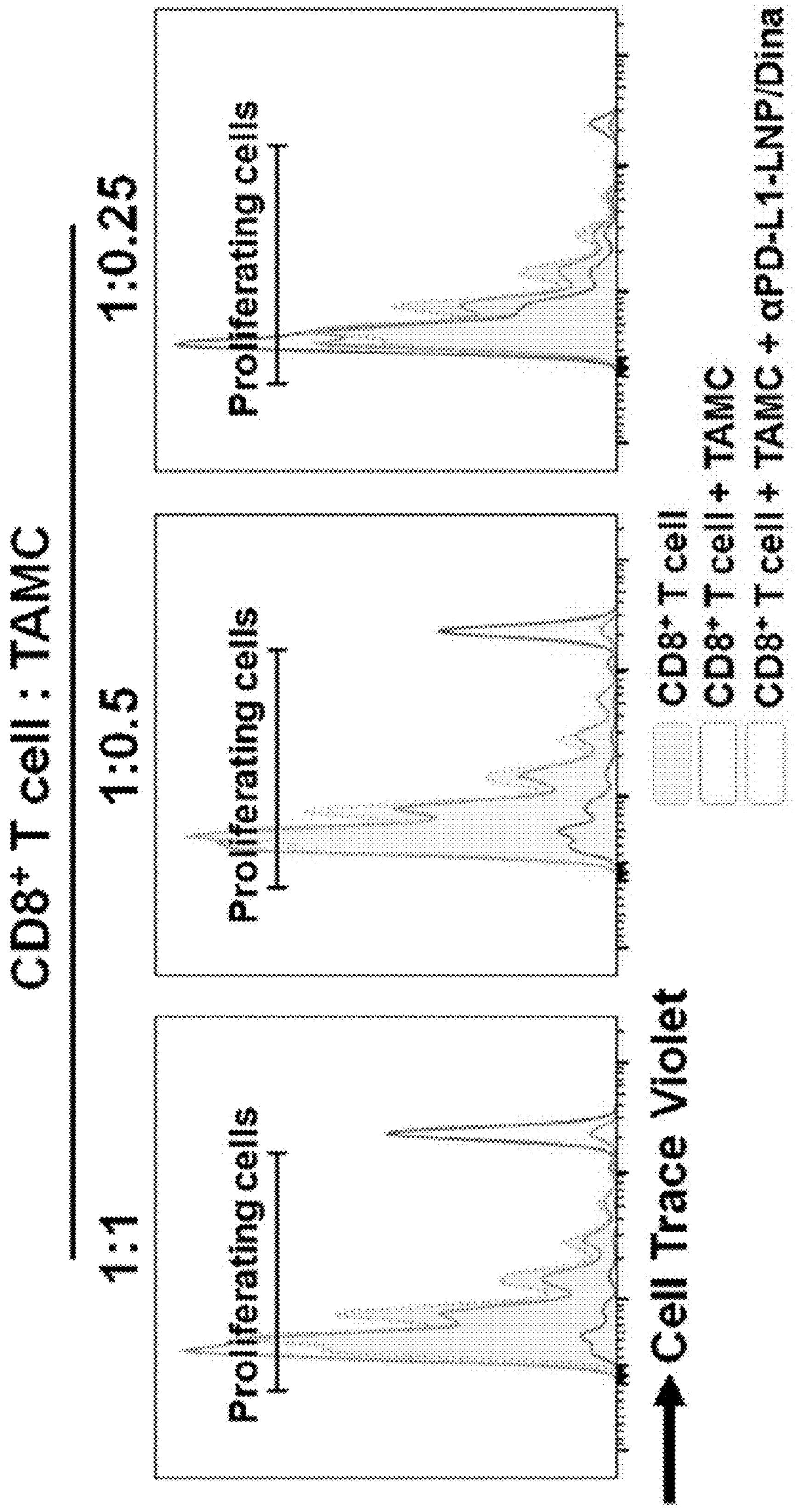
Figure 14:
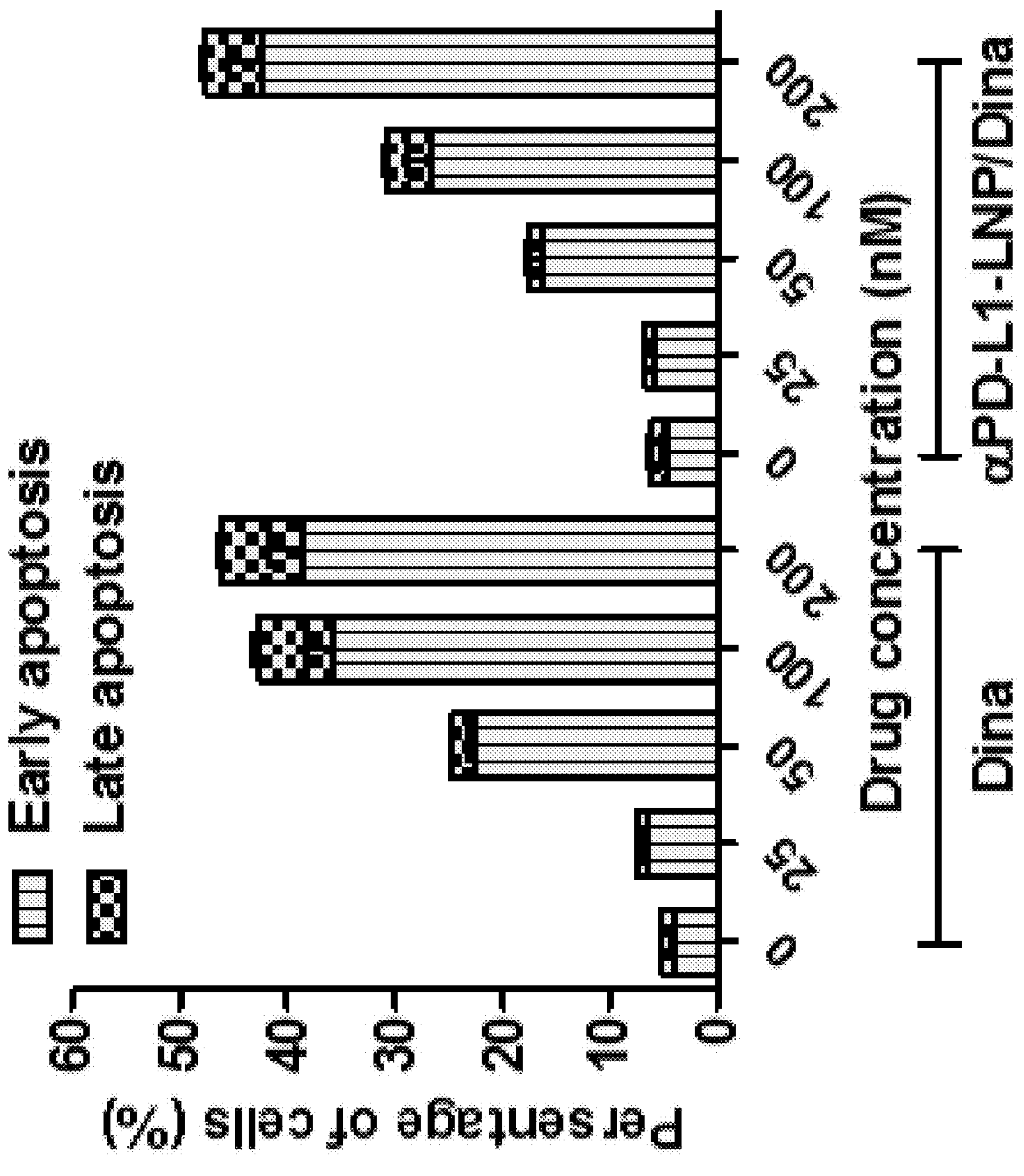
FIG. 14. Cytotoxicity of Dina and nano-formulation in GL261 glioma cells. Apoptosis of GL261 cells after treatment with Dina or αPD-L1-LNP/Dina at different concentrations was determined by annexin v staining 24 h post-treatment.

Therapeutic LNPs induce cytotoxicity and attenuate immunosuppressive functions of TAMCs. The effects of PD-L1 targeting LNPs carrying therapeutic payload were first evaluated in vitro. To construct the therapeutic LNPs, Dina, a small molecule CDK5 inhibitor, was readily encapsulated into the phospholipid bilayers (FIG. 3A). The resulting Dina-loaded LNPs (αPD-L1-LNP/Dina) demonstrated high effectiveness in inhibiting TAMCs in terms of viability as well as immunosuppressive activities. As shown in FIG. 3B, αPD-L1-LNP/Dina induced cytotoxicity in TAMCs in a dose-dependent manner. The treatment with αPD-L1-LNP/Dina at a Dina concentration of 12.5 and 25 nM for 24 h induced apoptosis in less than 20% of TAMCs; however, when the dose was increased to 50 nM, a vast majority of the TAMCs were effectively eliminated. Treatment of cells with free Dina demonstrated comparable cytotoxicity, confirming that the cytotoxic effect is caused by the payload drug (FIG. 3B). In contrast, drug-free nanoparticles did not affect the viability of TAMCs. Compared to TAMCs, GL261 glioma cells demonstrated lower sensitivity to Dina treatment (FIG. 14).

Figure 15:
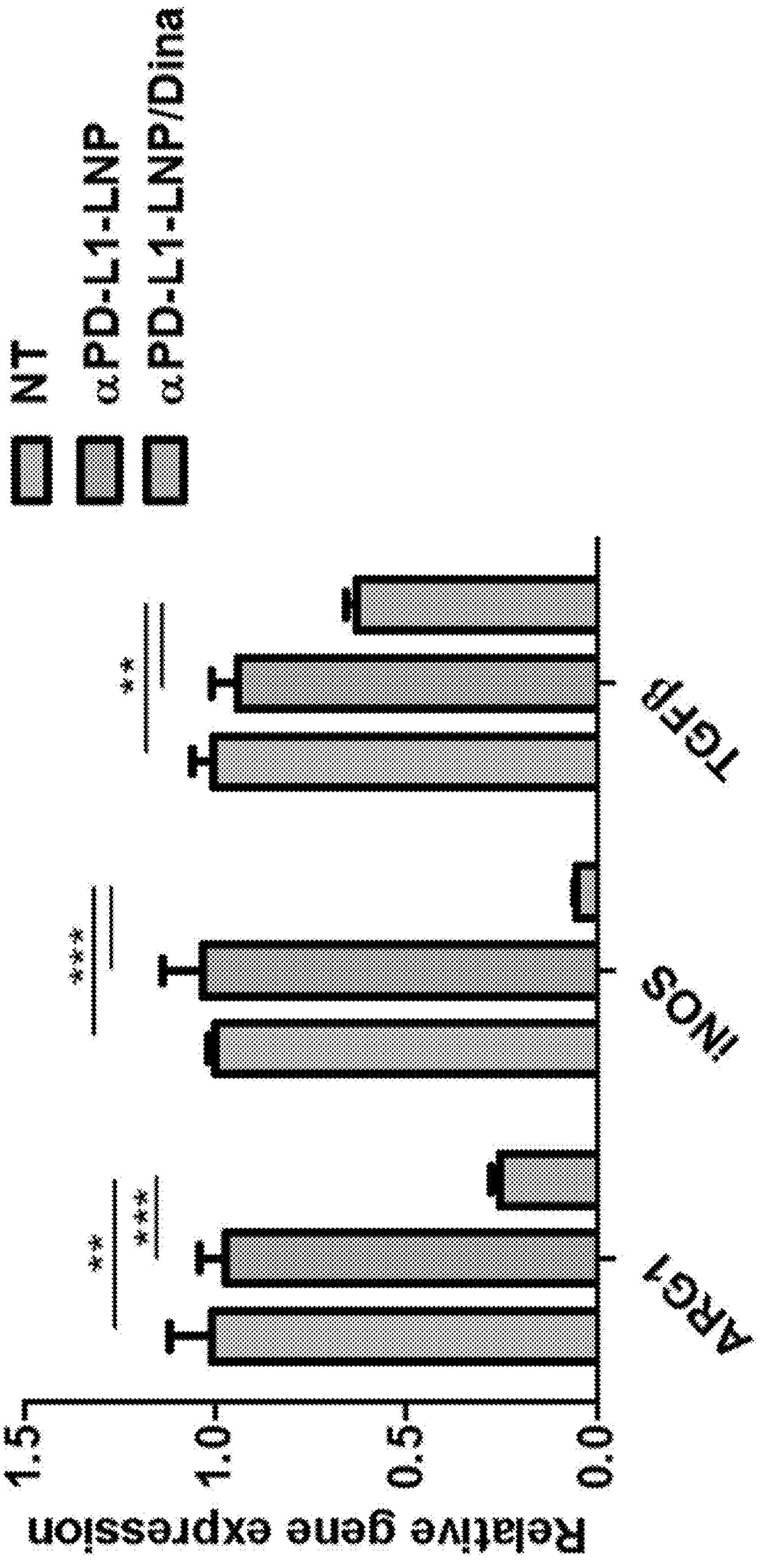
FIG. 15. Quantification of mRNA levels of ARG1, iNOS, and TGFβ in TAMCs by RT-qPCR. mRNA levels were normalized to beta-actin and reported relative to control TAMC expression. Data represented as mean±SEM; n=3; , $p<0.01$; *, $p<0.001$; determined by one-way ANOVA with Tukey's multiple comparisons test.

As an important mechanism to dampen T cell activity and induce immunosuppression, PD-L1 is highly upregulated on TAMCs, which is known inducible by IFNγ. Treatment with a low dose of Dina at 25 nM, a sub-lethal dose, was sufficient to remarkably inhibit the IFN-stimulated production of PD-L1 in TAMCs, as measured by both mRNA (FIG. 3C) and protein levels (FIG. 3D). Interestingly, compared to free drug, αPD-L1-LNP/Dina demonstrated a remarkably enhanced capacity of PD-L1 inhibition in TAMCs (FIG. 3D), which may be due to the synergistic effect of Dina+αPD-L1-LNP to simultaneously impair the de-novo synthesis of PD-L1 and induce its lysosomal degradation. Besides PD-L1, a variety of key factors associated with immunosuppressive activities of TAMCs, including arginase 1 (ARG1), inducible nitric oxide synthase (iNOS), and transforming growth factor beta (TGFβ) were also dramatically suppressed by the treatment of αPD-L1-LNP/Dina (FIG. 15).

Figure 16:
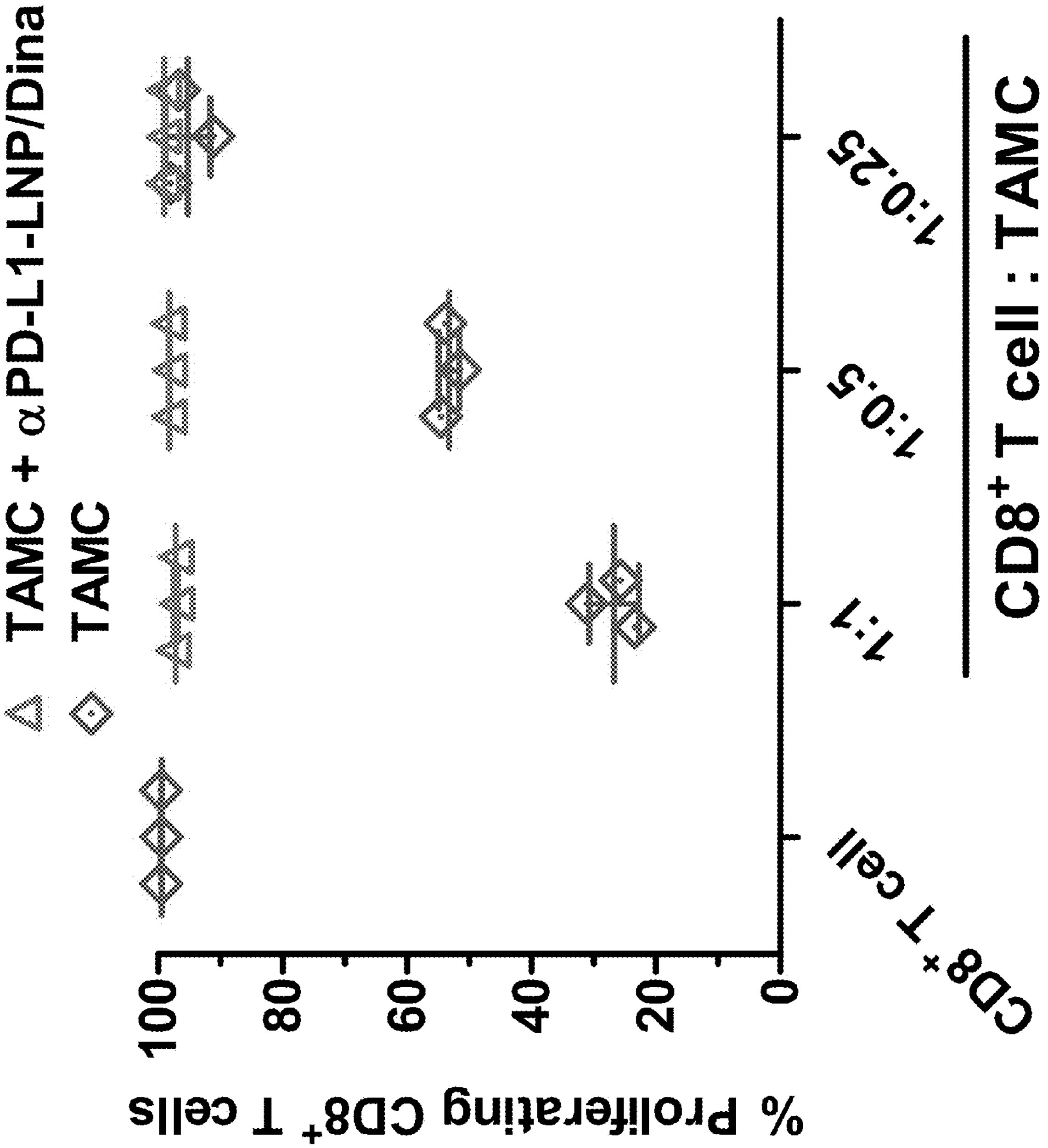
FIG. 16. Quantification of percentage positive population of proliferating $CD8^+$ T cells co-cultured with non-treated TAMCs or 25 nM of αPD-L1-LNP/Dina treated TAMCs as compared to $CD8^+$ T cells alone.

Since one of the major immunosuppressive mechanisms of TAMCs is to inhibit the proliferation of cytotoxic T lymphocytes (CTLs) (21), we next evaluated if our LNP treatment affects CTL proliferation. TAMCs were treated with 25 nM of αPD-L1-LNP/Dina and then co-cultured with $CD8^+$ T cells. As expected, TAMCs significantly inhibited proliferation of $CD8^+$ T cells. Only 26.8% and 53.3% of $CD8^+$ T cells remained proliferating in the presence of non-treated TAMCs at a CTL:TAMC ratio of 1:1 and 1:0.5, respectively (FIG. 3E and FIG. 16). However, after treatment with αPD-L1-LNP/Dina, the immunosuppressive activity of TAMCs was dramatically impaired as indicated by the lack of inhibition on $CD8^+$ T cell proliferation. Overall, these data may suggest a dual action of αPD-L1-LNP/Dina on TAMCs, by impairing the immunosuppressive functionalities and/or largely inducing apoptosis, in a dose-dependent manner.

Figure 4:
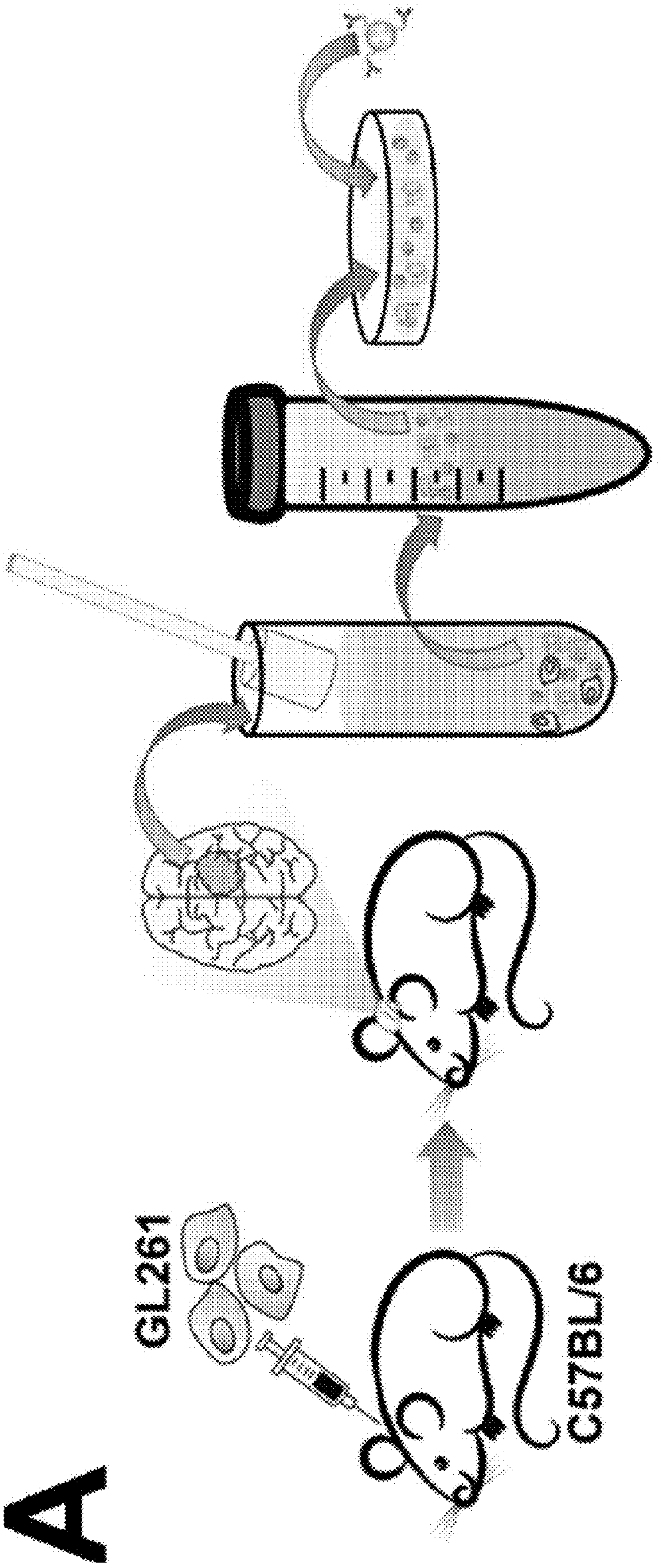
FIG. 4. Therapeutic LNPs actively target TAMCs in ex vivo and in vivo glioma model, and extend survival of glioma-bearing mice. (A) Schematic of isolating immune infiltrates in GL261 glioma model. (B) Flow cytometric analysis of distribution of Rhod-PE labeled LNPs among immune cell subsets, as represented by MFI (n=3). (C-D) Flow cytometric analysis of glioma-associated immune cells after treatment with αPD-L1-LNP/Dina at a Dina concentration of 0, 25, and 50 nM for 72 h (n=4). (C) Representative gating of $CD45^{high}$ CD11b-tumor-infiltrating lymphocyte (TIL), $CD45^{high}$ $CD11b^+$ TAMC, and $CD45^{int}$ $CD11b^+$ microglia. (D) The cell abundance was determined by cell counts and flow cytometry analysis, as normalized to non-treated control. (E) Distribution of Rhod-PE labeled αPD-L1-LNPs at brain tumor site 24 h post-injection. Scale bar, 100 μm. (F) Survival curves of GL261-bearing mice after two administrations of saline, drug-free αPD-L1-LNP, Iso-LNP/Dina, or αPD-L1-LNP/Dina at 2.5 mg/kg Dina on day 7 and 14 after intracranial implantation of $5\times10^4$ GL261 glioma cells. n=7-8 mice per group. Data are represented as mean±SEM; *, $p<0.05$; , $p<0.01$; *, $p<0.001$; determined by one-way ANOVA (in D) or two-way ANOVA (in B) with Tukey's multiple comparisons test, or Log-rank method with p values adjusted by Bonferroni correction (in F).
Figure 4:
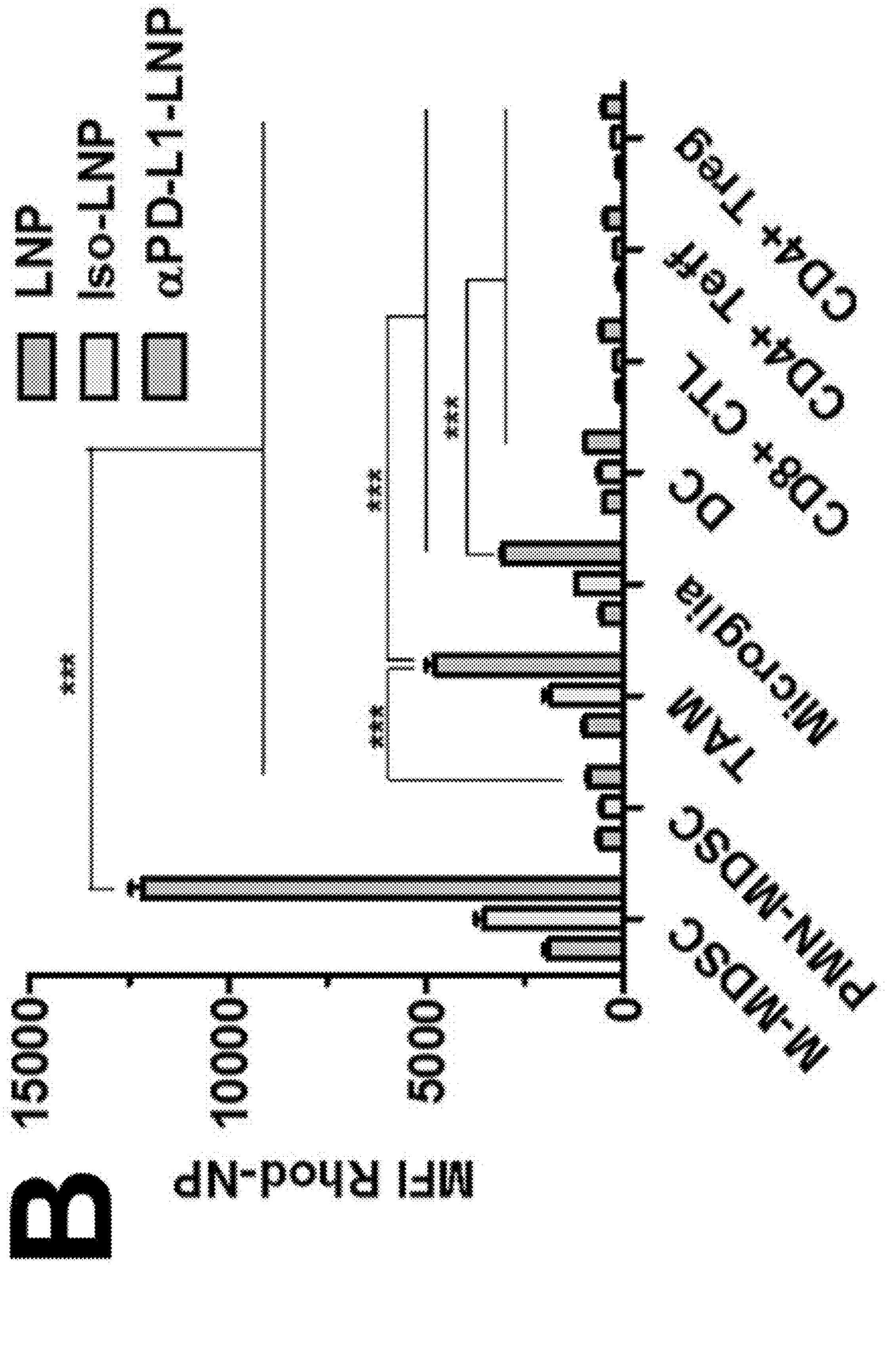
Figure 4:
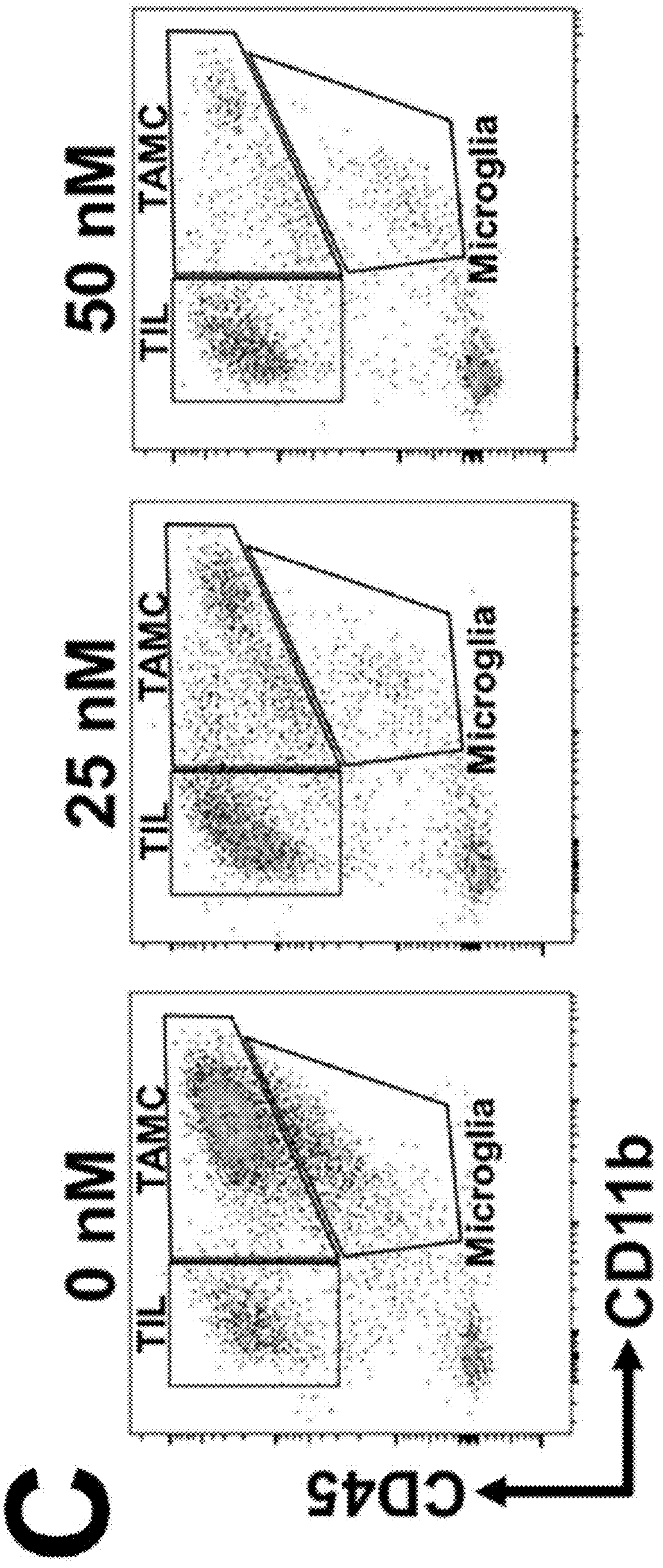
Figure 4:
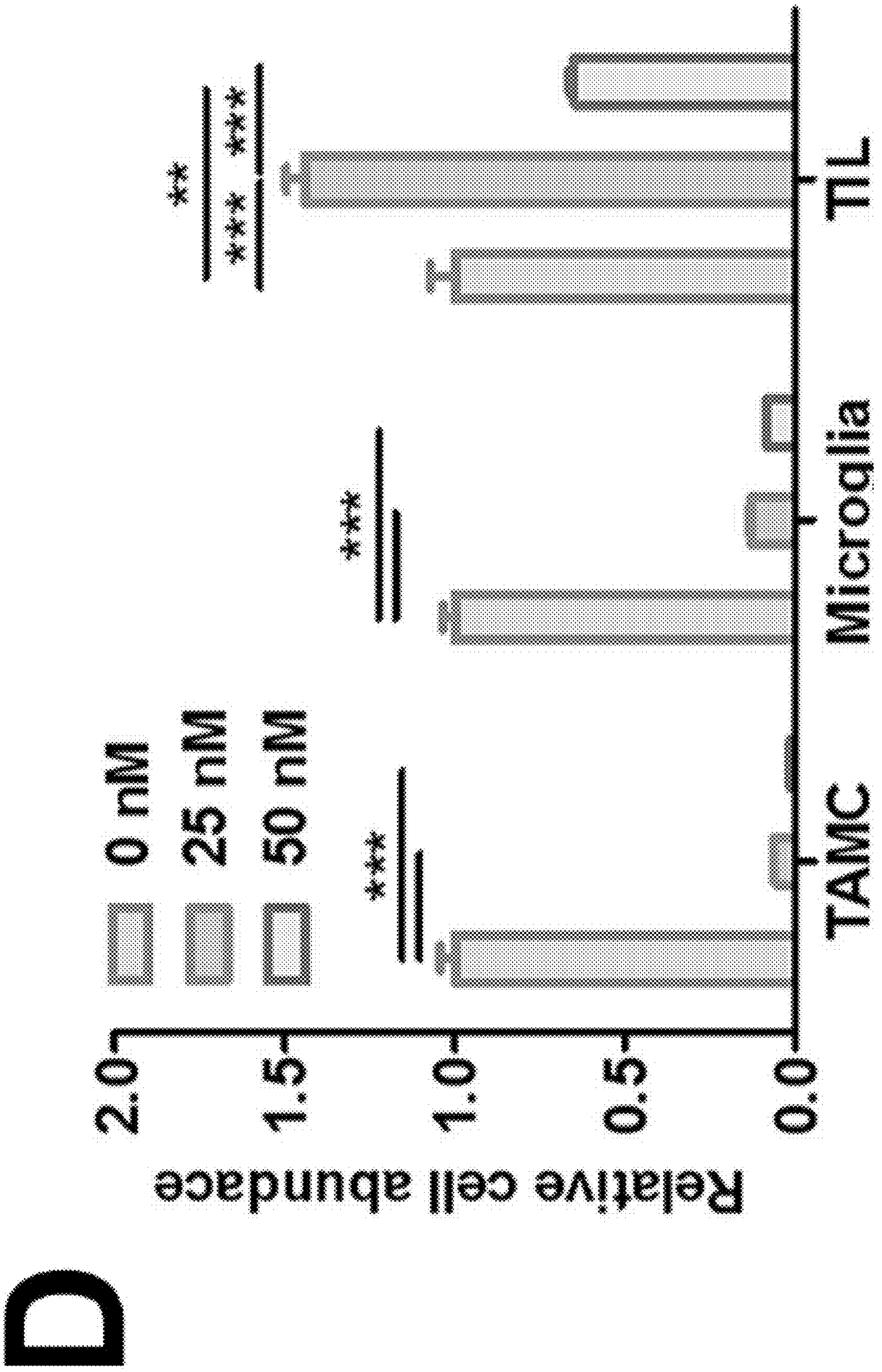
Figure 4:
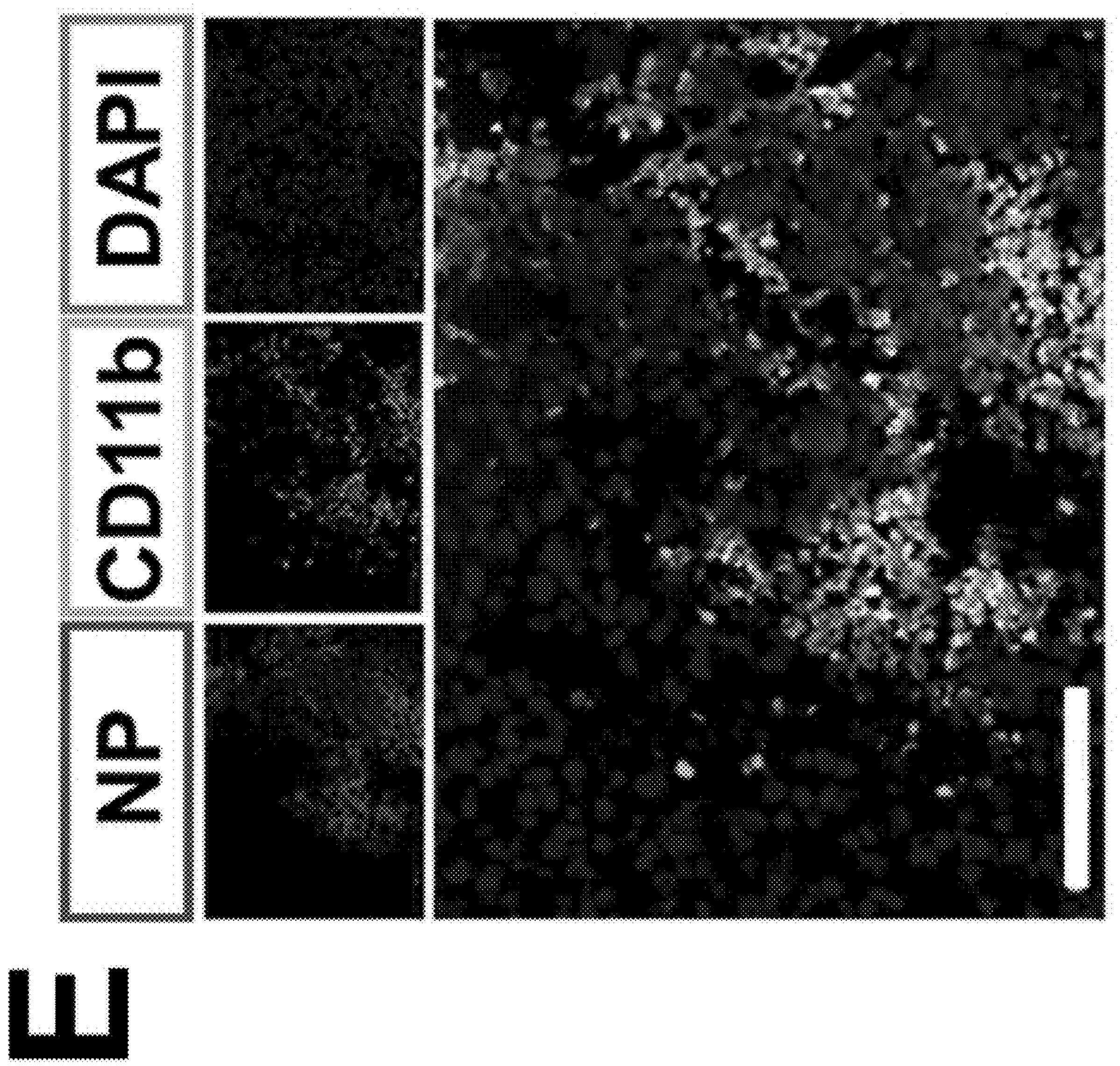
Figure 4:
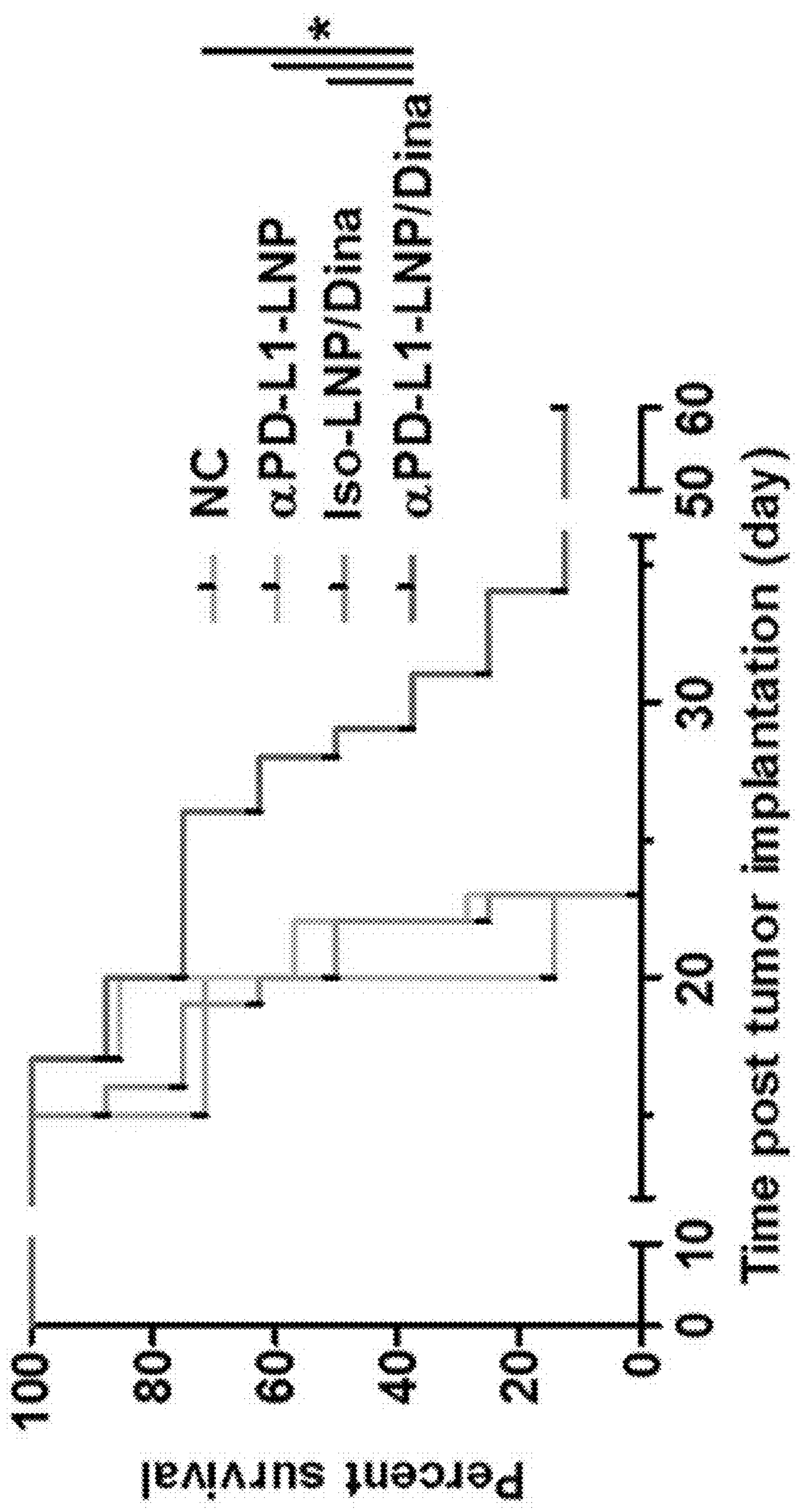

Therapeutic LNPs actively target and eliminate TAMCs in ex vivo model. The targetability of αPD-L1-LNPs were further assessed using an ex vivo model, in which immune infiltrates were isolated by percoll gradient from the intracranial GL261 glioma tumors in mice (FIG. 4A). Consistent with the in vitro results, surface modified αPD-L1 actively targeted LNPs to TAMCs and dramatically increased the cellular uptake in comparison to control LNPs (FIG. 4B). Among all the examined immune cell subsets, M-MDSCs and TAMs were the major targets and presented highest efficiency in taking up αPD-L1 decorated LNPs. In contrast, LNPs were not highly distributed into PMN-MDSCs, of which the phagocytic activity is known much lower (35).

Figure 17:
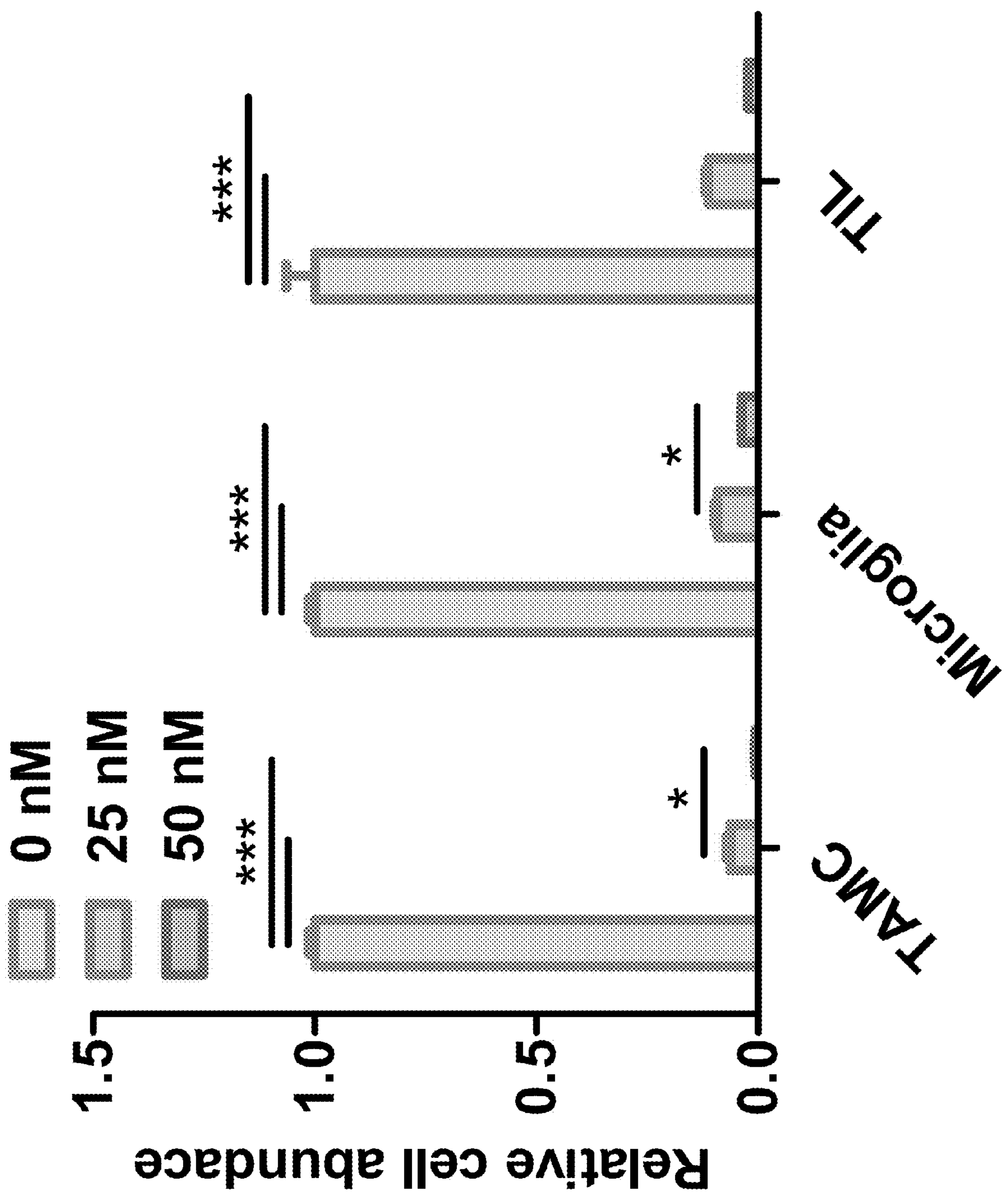
FIG. 17. Flow cytometric analysis of glioma-associated immune cells after treatment with free Dina at 0, 25, and 50 nM for 72 h. Data are represented as mean±SEM; n=3; *, $p<0.05$; ***, $p<0.001$; determined by one-way ANOVA with Tukey's multiple comparisons test. The abundance of TAMC, microglia, and TIL after treatment with Dina was determined by cell counts and flow cytometry analysis, as normalized to non-treated control.
Figure 18:
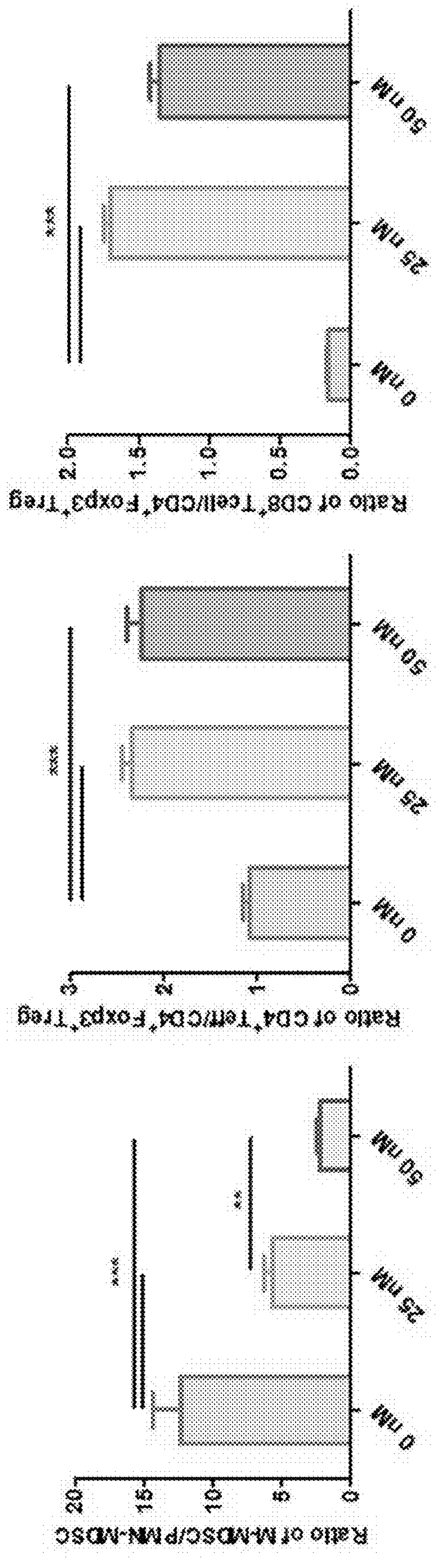
FIG. 18. Quantification of M-MDSC/PMN-MDSC, $CD4^+$ $Foxp3^-$ T cell/$CD4^+$ $Foxp3^+$ Treg, and $CD8^+$ T cell/$CD4^+$ $Foxp3^+$ Treg ratio. Data are represented as mean±SEM; n=4; , $p<0.01$; *, $p<0.001$; determined by one-way ANOVA with Tukey's multiple comparisons test.

Building on the capability of highly efficient and selective delivery to TAMCs, ex vivo treatment with αPD-L1-LNP/Dina effectively eliminated TAMCs without showing significant off-target toxicity to tumor-infiltrating lymphocytes (TIL) (FIG. 4C), as further quantified by the change in cell abundance (FIG. 4D), whereas free Dina caused severe off-target cytotoxicity and non-specific elimination of all immune cell populations (FIG. 17). Among subsets of MDSCs, αPD-L1-LNP/Dina presented higher potency in eliminating M-MDSCs (FIG. 18), which is correlated with the highest targetability towards M-MDSCs as demonstrated by such nanoparticles (FIG. 4B). And it is also worth noting that frequency of $CD4^+$ $Foxp3^+$ Tregs was decreased by the treatment (FIG. 18), which might be a downstream effect of the elimination/inactivation of TAMCs.

Figure 19:
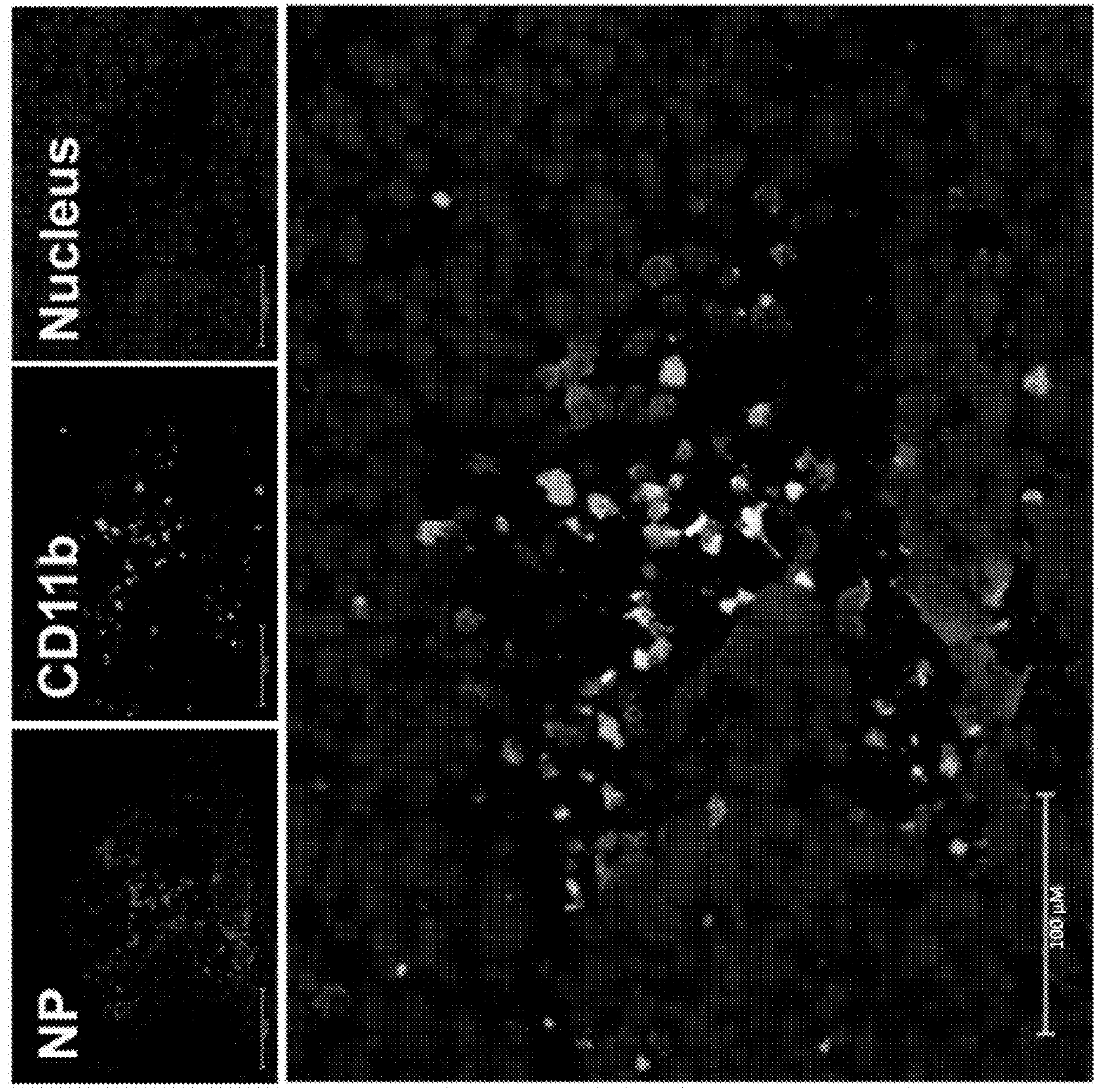
FIG. 19. Distribution of Rhod-PE labeled LNPs at the brain tumor. The brain was harvested from GL261-bearing mouse 24 h post intracranial delivery of Rhod-PE labeled LNPs through cannula. Myeloid cells were stained with Alexa Fluor 488 CD11b and cell nuclei were stained with DAPI. Scale bar, 100 μm.

Therapeutic LNPs effectively target TAMCs in vivo and extend survival of glioma-bearing mice. We next determined the in vivo ability of αPD-L1-LNP/Dina to target TAMCs and to control tumor progression in GL261 glioma bearing mice. A cannula implantation system was established for multiple intracranial injections of nanoparticles into mice. Biodistribution of TAMC targeting LNPs in brain tumor was tracked by Rhod-PE tagged phospholipids 24 h post intracranial administration. As shown in FIG. 4E, αPD-L1-LNPs were highly retained at the brain tumor site and, importantly, substantially co-localized with TAMCs. In contrast, much lower retention of control LNPs was observed at tumor site (FIG. 19).

Figure 20:
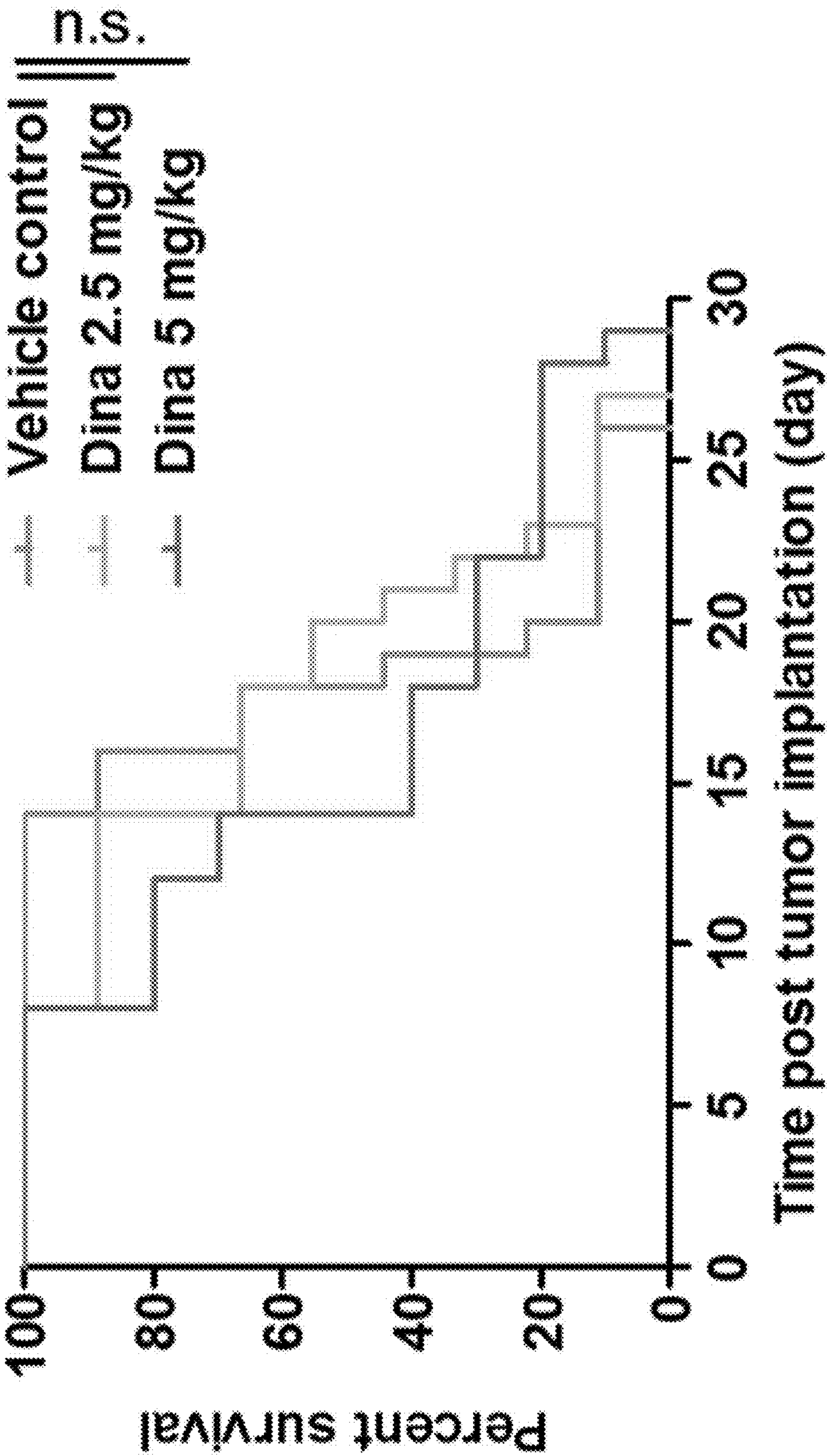
FIG. 20. Survival curves of GL261-bearing mice after administration of free Dina. The therapeutic efficacy of free Dina was evaluated with two injections of vehicle or Dina dissolved in 20% 2-hydroxypropyl-β-cyclodextran at 2.5 mg or 5 mg Dina per kg on the seventh and fourteenth day post-intracranial inoculation of $5\times10^4$ GL261 glioma cells. n=9-10 mice per group; n.s., not significant; determined by Log-rank method with p values adjusted by Bonferroni correction.

The therapeutic efficacy of the proposed nano-immunotherapy strategy was evaluated in mice bearing GL261 glioma. GL261 is known as an aggressive murine glioma model, which led to a short median survival of 20 days in glioma bearing mice (FIG. 4F). Intracranial injection of drug-free LNPs (αPD-L1-LNP) and non-targeting nanoparticles (Iso-LNP/Dina) showed no significant benefit on overall survival. However, administration of αPD-L1-LNP/Dina led to a dramatically enhanced therapeutic effect ($p<0.05$). Only two injections of αPD-L1-LNP/Dina at a dose of 2.5 mg Dina/kg substantially extended the median survival of glioma-bearing mice to 28.5 days. In comparison, administration of free Dina at two different doses (2.5 and 5 mg/kg) did not lead to notable improvement in animal survival (FIG. 20), likely due to the lack of specificity and off-target toxicity.

Figure 5:
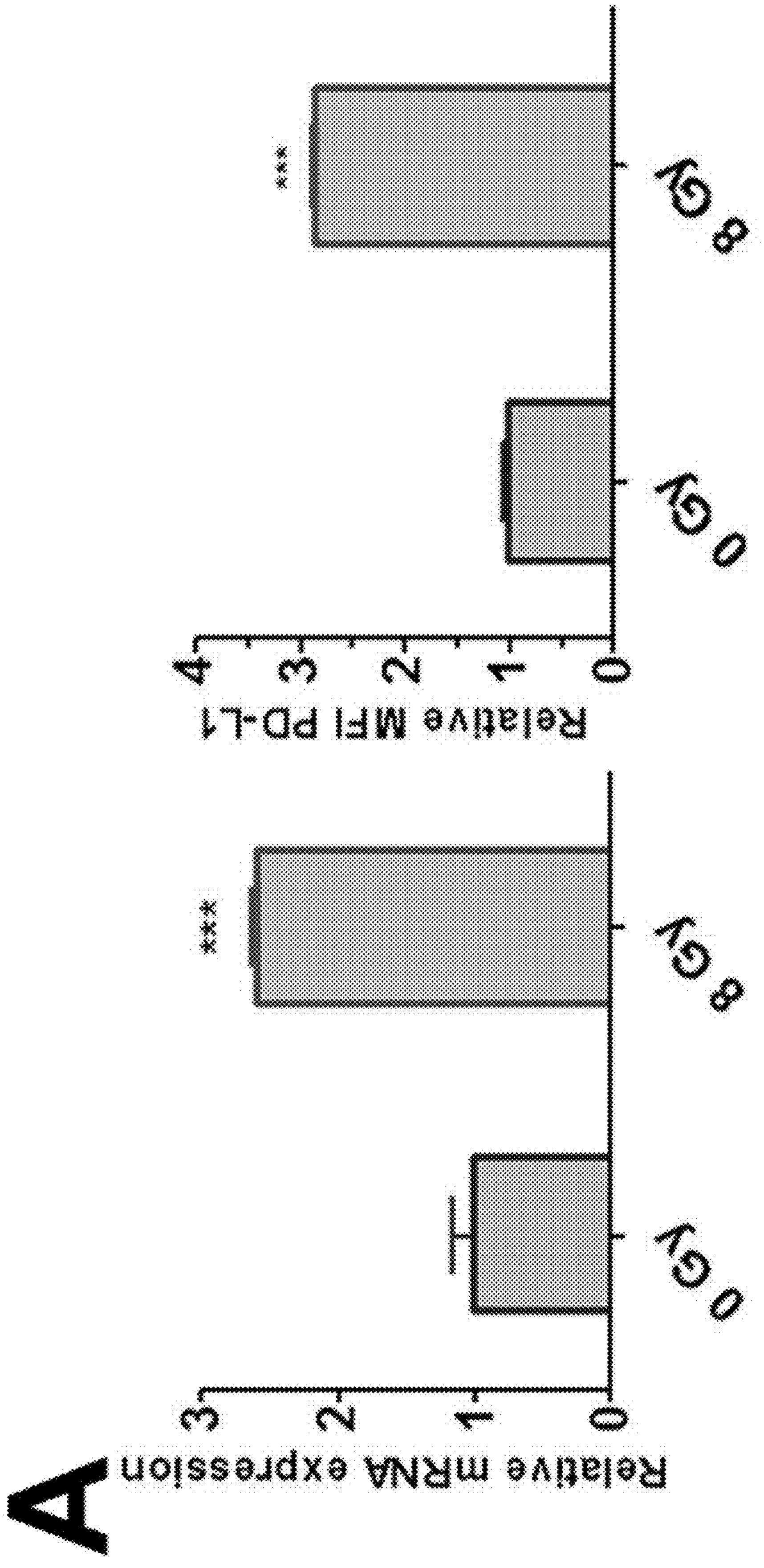
FIG. 5. Irradiation upregulates PD-L1 expression on TAMCs and enhances targeted delivery to TAMCs. (A) RT-qPCR and flow cytometric quantification of PD-L1 expression on TAMCs as normalized to control TAMC expression. (B) Flow cytometric quantification of cellular uptake of Rhod-PE labeled LNPs in TAMCs after 1 h of incubation, as presented by the percentage of $NP^+$ cells (blue, non-treated TAMCs). (C) Flow cytometric quantification of percentage of PD-L1 positive TAMCs (blue, Iso control). (D) Cell circle analysis of TAMCs treated with PBS, RT (8 Gy), αPD-L1-LNP, αPD-L1-LNP/Dina (25 nM Dina), or RT+αPD-L1-LNP/Dina (25 nM Dina). Data are represented as mean±SEM; n=3; *, $p<0.05$; ***, $p<0.001$; determined by Student's t-test (in A), or one-way ANOVA with Tukey's multiple comparisons test (in D).
Figure 5:
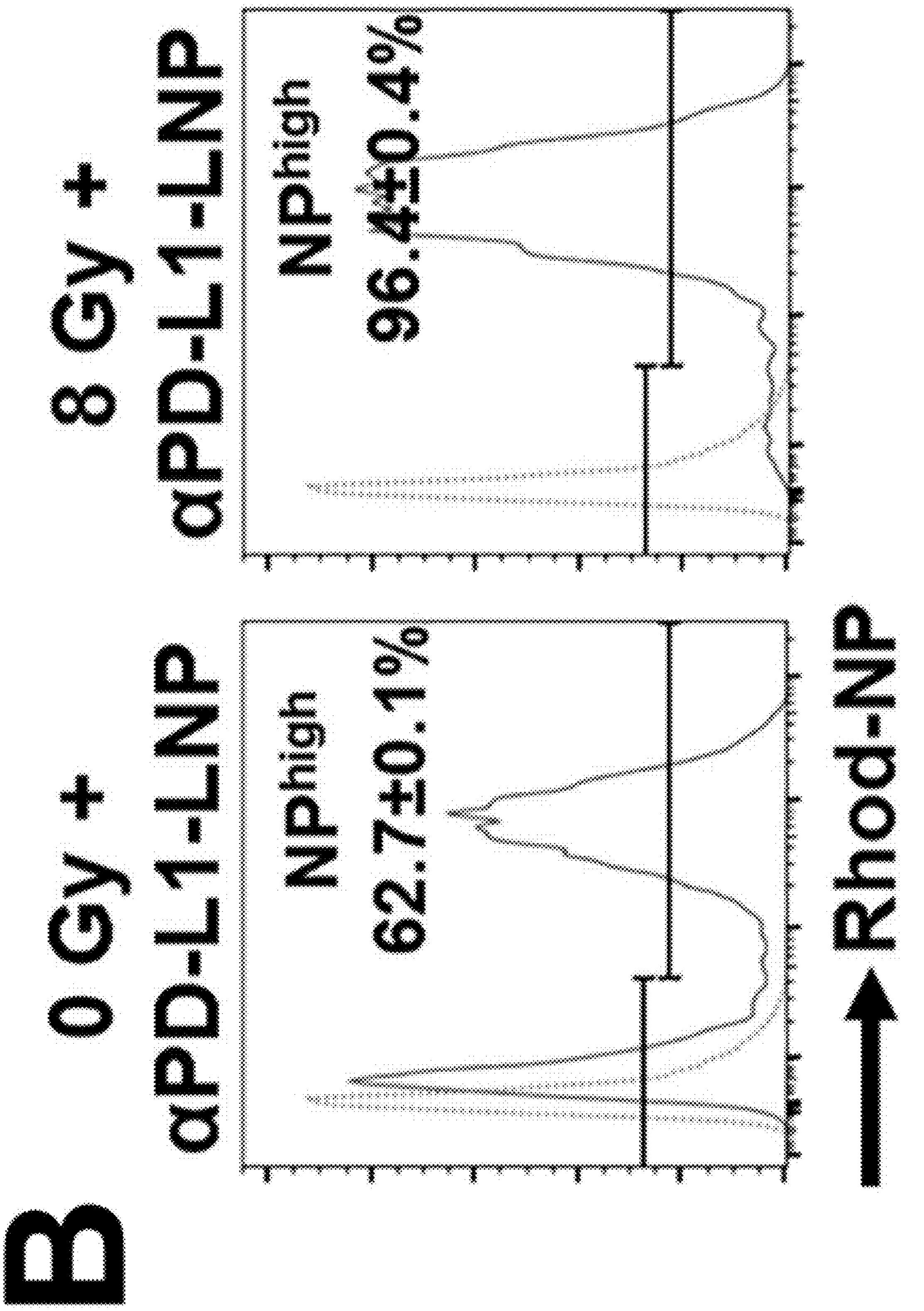
Figure 5:
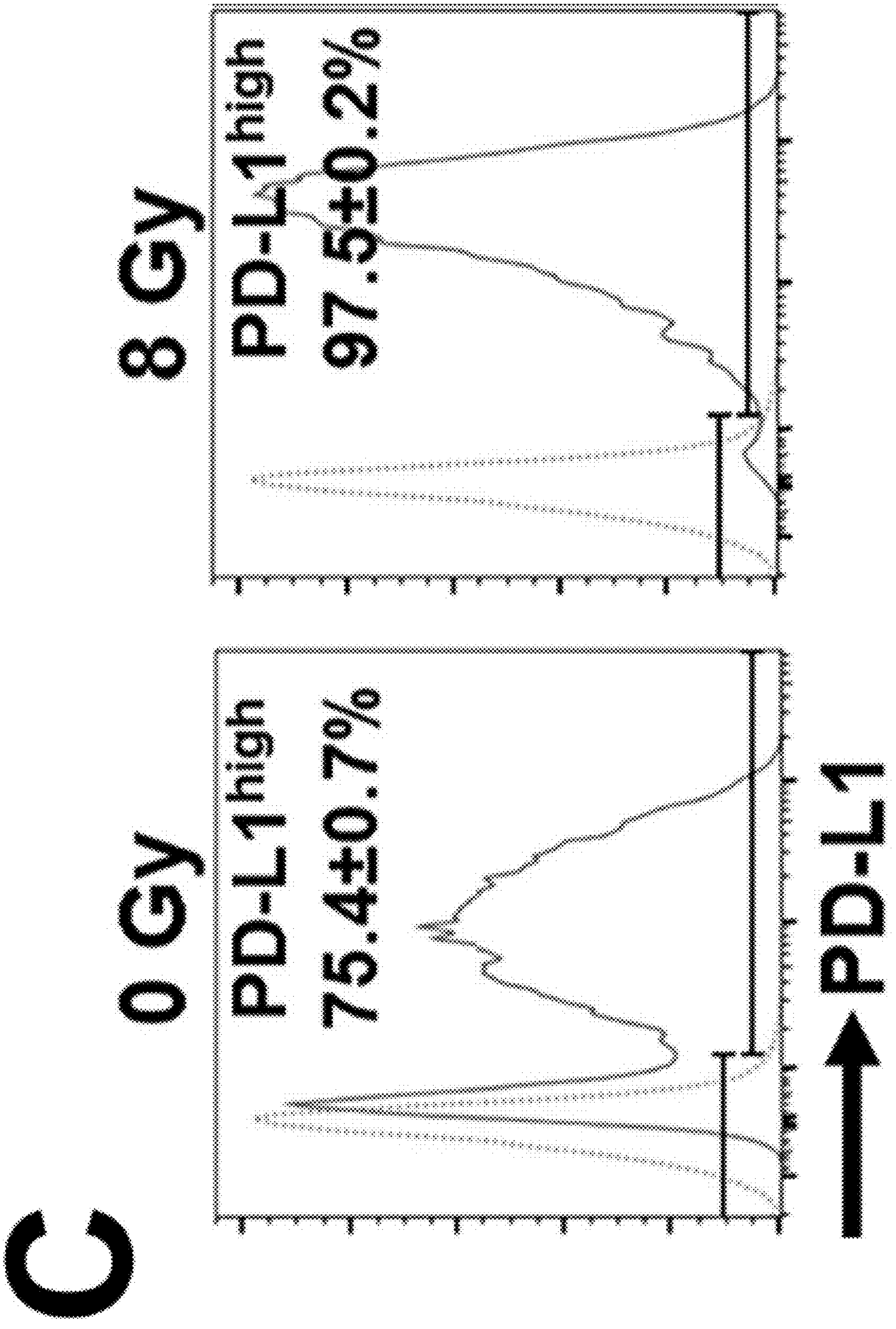
Figure 5:
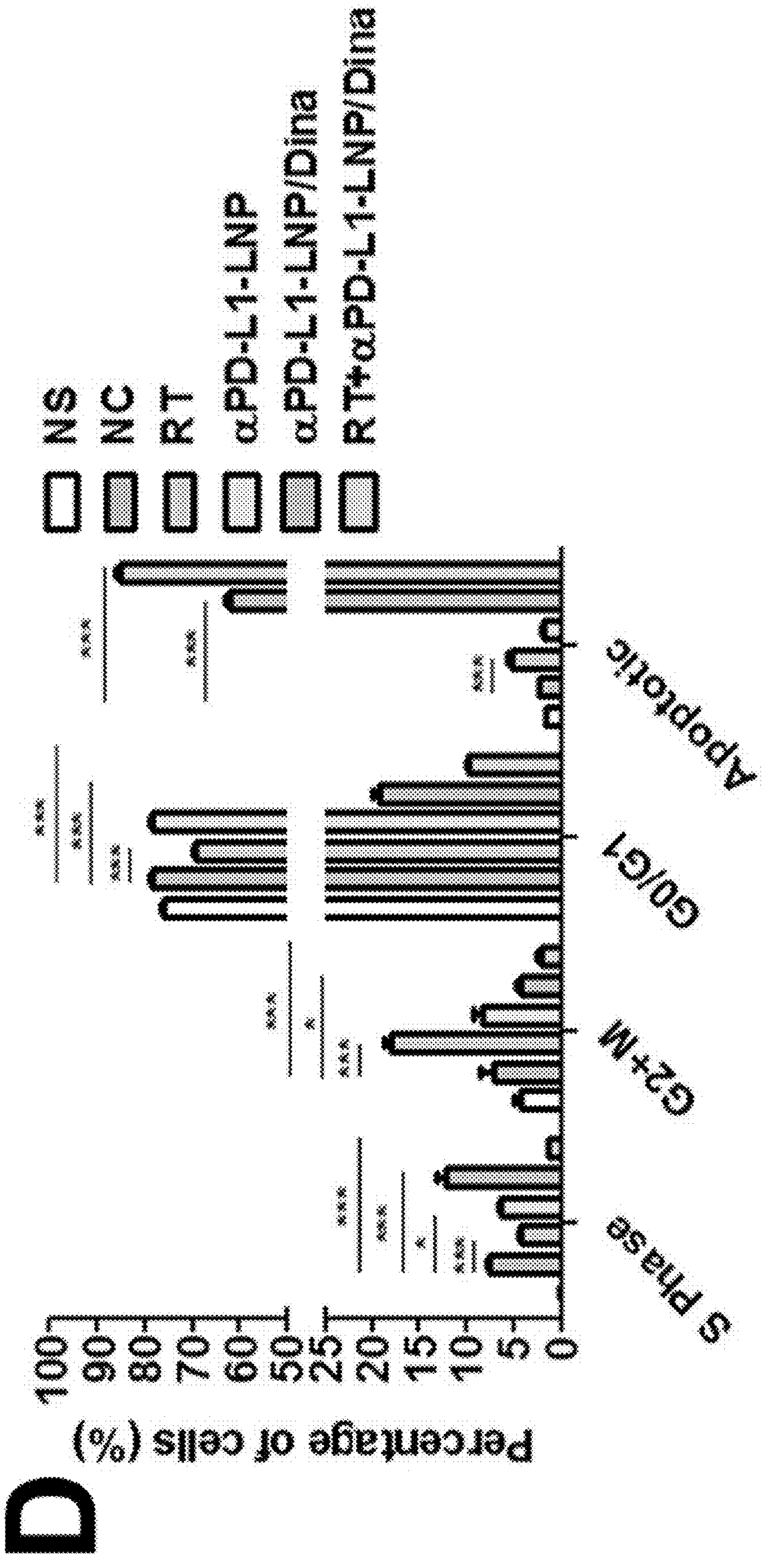
Figure 21:
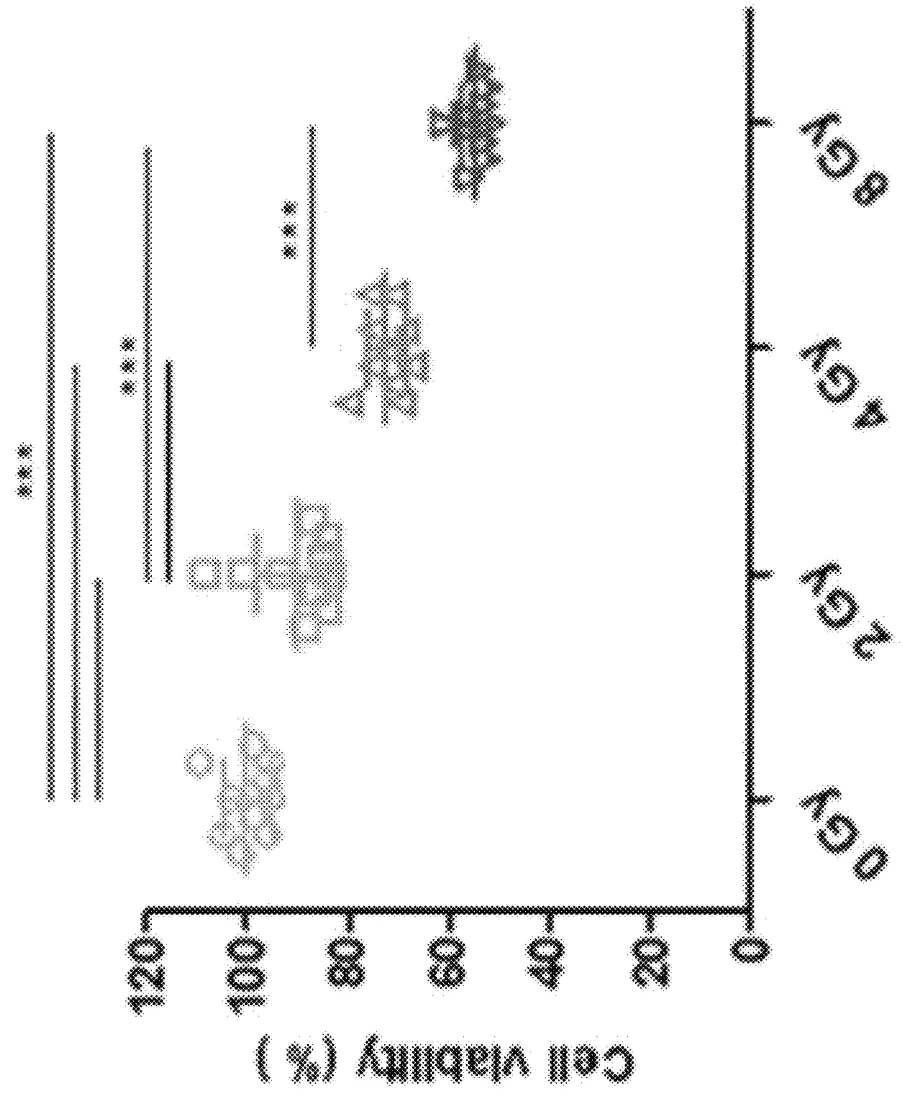
FIG. 21. RT-induced apoptosis of GL261 glioma cells. Apoptosis of GL261 cells was determined 72 h post-RT by (A) MTT assay (n=10; ***, p<0.001; determined by one-way ANOVA with Tukey's multiple comparisons test), and (B) annexin v staining analyzed by flow cytometer.
Figure 21:
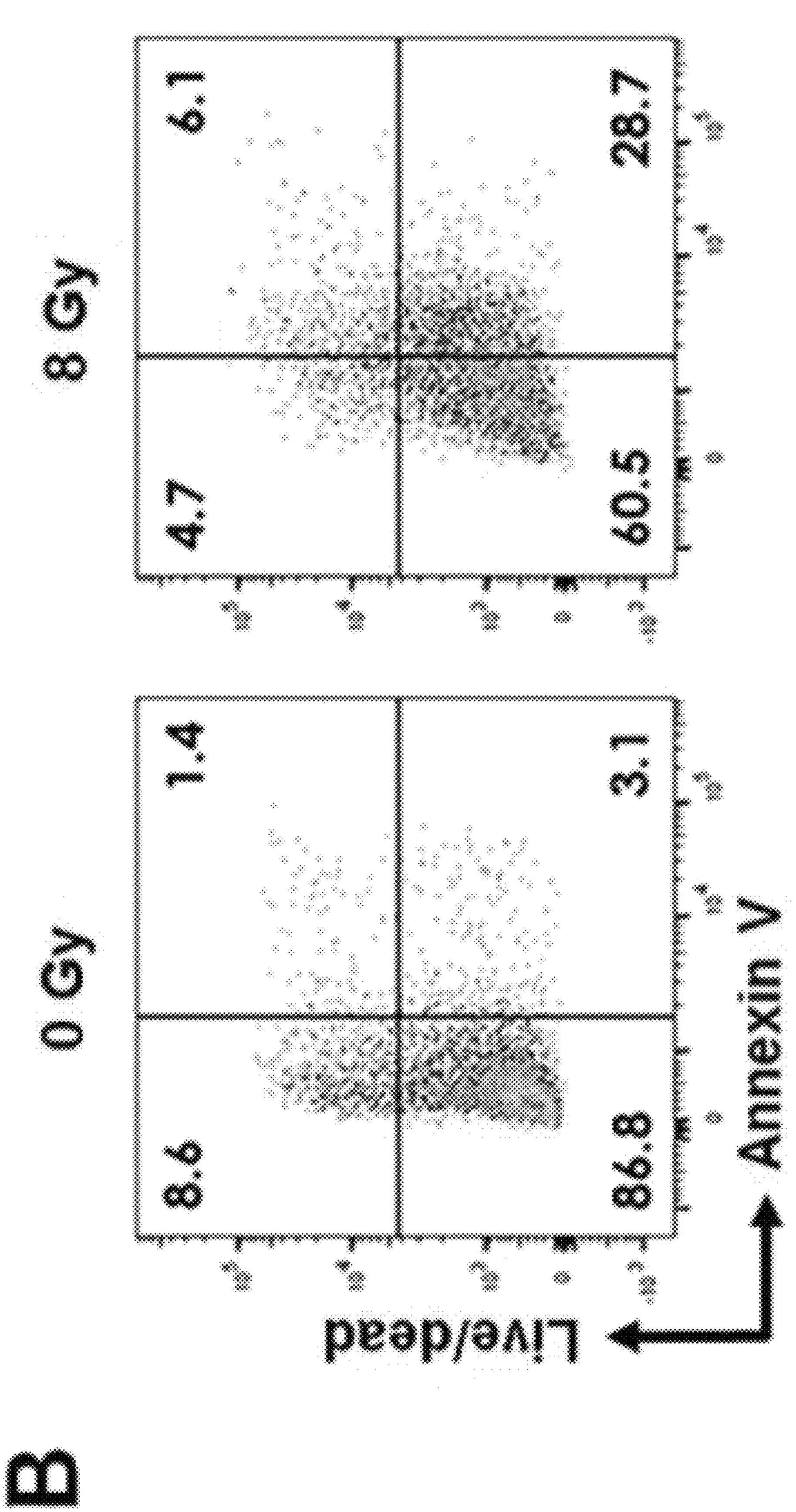
Figure 22:
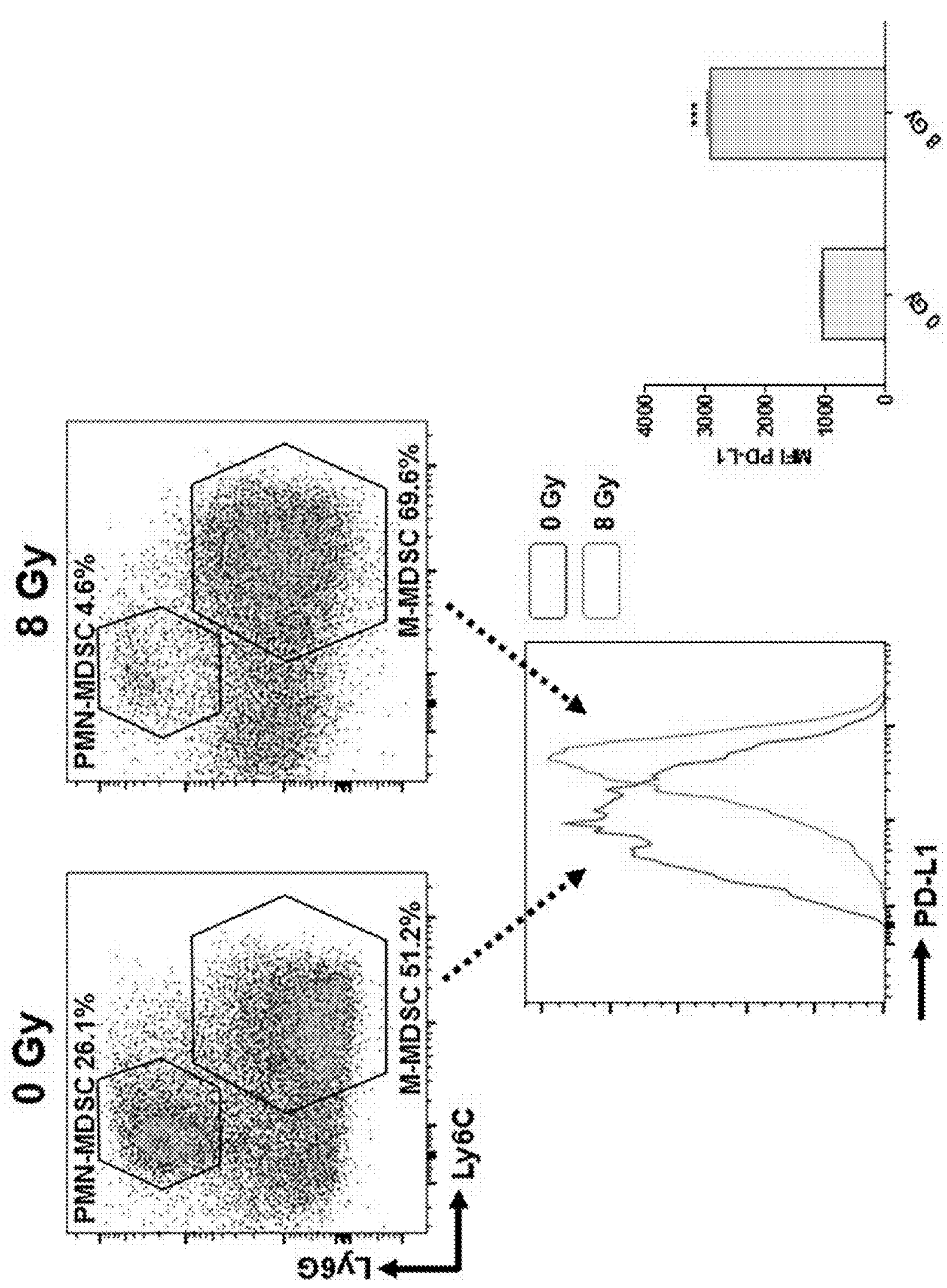
FIG. 22. Phenotyping of GL261-associated TAMCs post-RT. Subsets and PD-L1 expression on TAMCs were analyzed by flow cytometry 72 h post-RT and quantified by mean fluorescence intensity. Data are represented as mean±SEM; n=3; ***, p<0.001; determined by Student's t-test.
Figure 23:
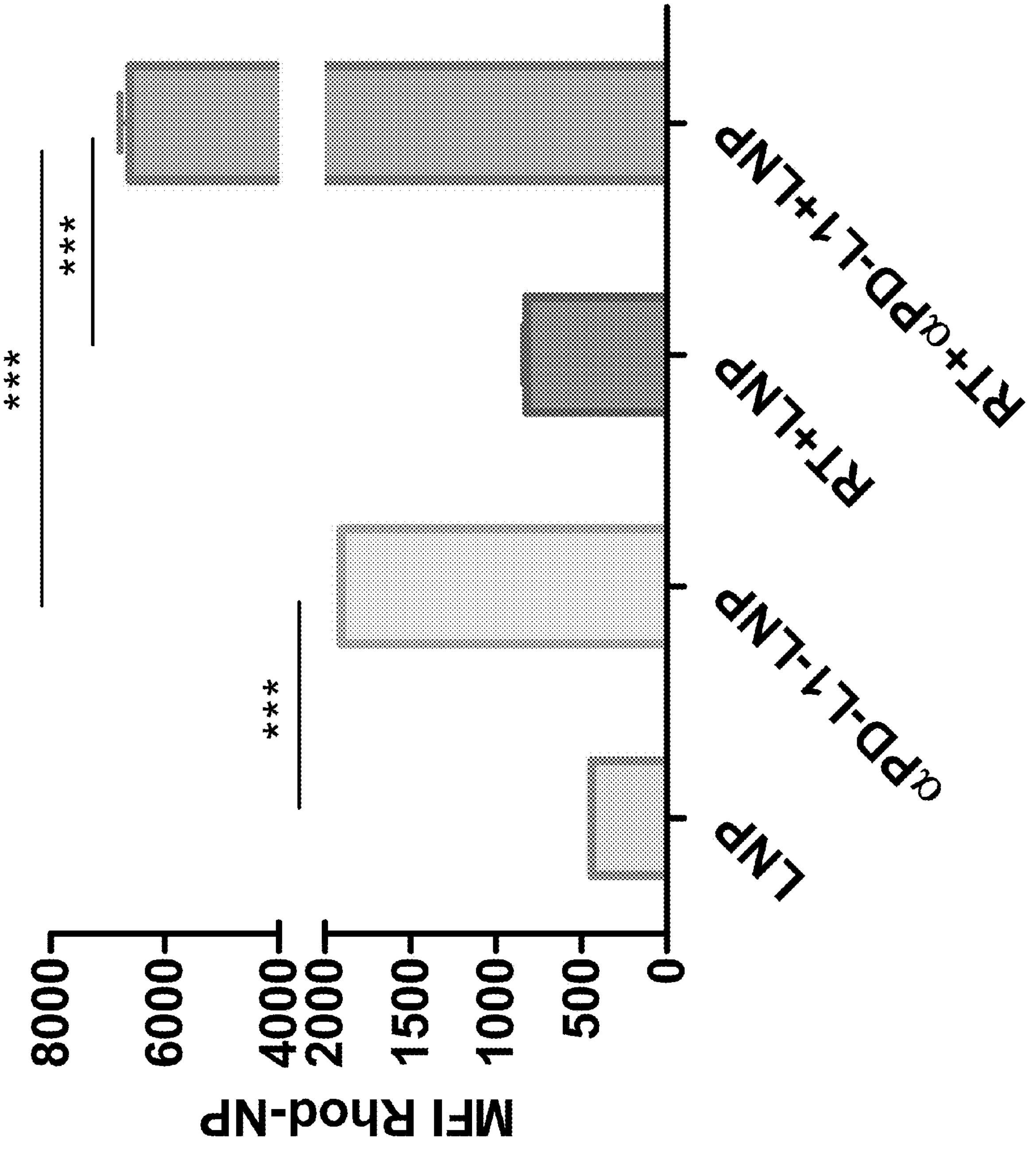
FIG. 23. Flow cytometric quantification of RT-enhanced cellular uptake of Rhod-PE labeled LNPs in TAMCs after 1 h of incubation, as presented by MFI. Data are represented as mean±SEM; n=3; ***, p<0.001; determined by one-way ANOVA with Tukey's multiple comparisons test.

Irradiation upregulates PD-L1 expression on TAMCs and enhances delivery efficiency to TAMCs. Radiation therapy (RT) has been widely used as a mainstay treatment of GBM in clinic, which induces apoptosis of tumor cells through damage of DNA (36). Indeed, irradiation caused cytotoxicity in GL261 glioma cells in a dose-dependent manner (FIG. 21). Importantly, the ability of irradiation to shape TME and host immunity has also been recognized, indicating an impact of RT on both tumor cells and immune cells (37-39). As shown in FIG. 5A, irradiation profoundly upregulated the expression of PD-L1 on in vitro generated TAMCs, as determined by both flow cytometry and RT-qPCR analysis. Notably, irradiation reduced the abundance of PMN-MDSCs, a PD-$L1^{low}$ sub-population of TAMCs, while further elevating PD-L1 expression on the PD-$L1^{high}$ sub-population, M-MDSCs (FIG. 22). This suggests that remaining radio-resistant subset of TAMCs (M-MDSCs) are more targetable by PD-L1 targeting LNPs. Indeed, the percentage of targetable TAMCs by αPD-L1-LNPs was dramatically increased from 62% to 96% post-irradiation (FIG. 5B), which was highly correlated with the capability of RT to reshape the composition and PD-L1 expression of TAMCs (FIG. 5C). Overall, irradiation induced a 3.5-fold increase in accumulative cellular uptake of αPD-L1-LNPs by TAMCs (FIG. 23), leading to an increased cytotoxicity in TAMCs after combination therapy over monotherapy (FIG. 5D).

Figure 6:
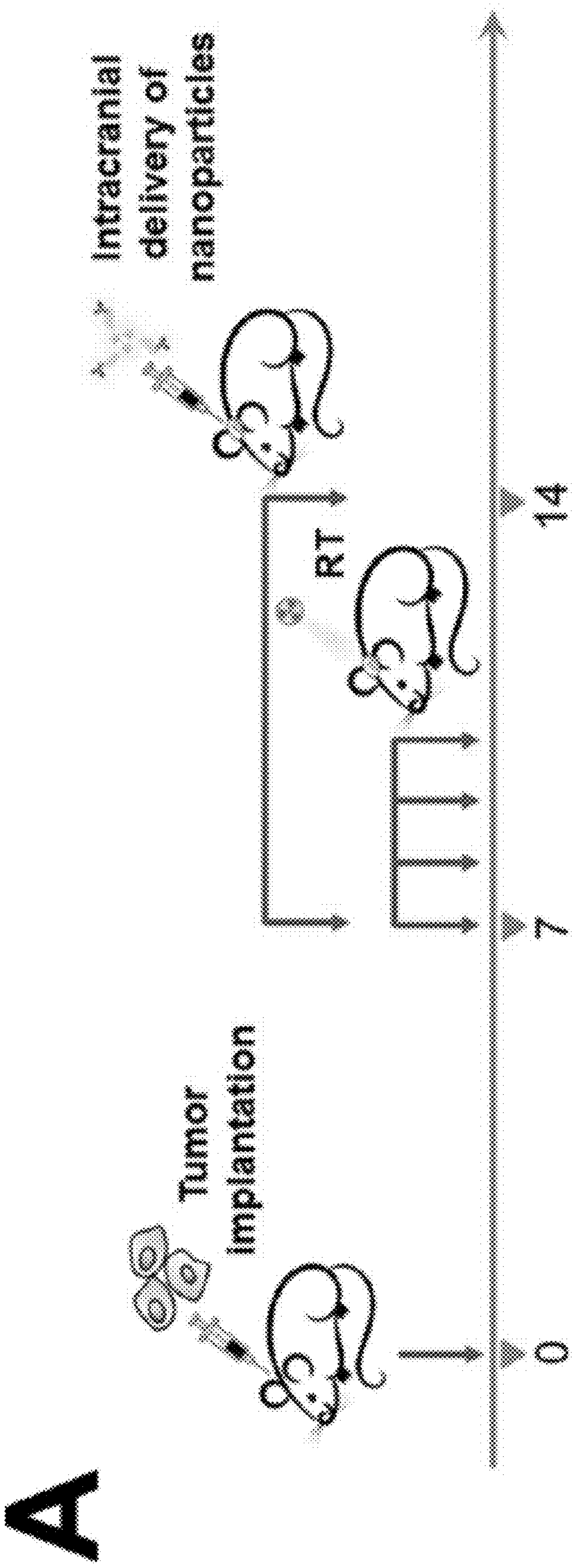
FIG. 6. Therapeutic nanoparticles synergize with radiation therapy to eliminate TAMCs and improve therapeutic efficacy in glioma-bearing mice. (A) Schematic representation of the experimental workflow of combination therapy in GL261 or CT2A-bearing mice. Selected groups received RT (2 Gy×4) as monotherapy or combination therapy. (B) Survival curves of mice received intracranial implantation of $2\times10^5$ GL261 glioma cells and two administrations of saline, drug-free αPD-L1-LNP, or αPD-L1-LNP/Dina (5 mg/kg Dina). n=10 mice per group. (C-G) Flow cytometric analysis of GL261 glioma-associated immune cells. The abundance of TAMCs was determined by cell counts and flow cytometry analysis, as normalized to control mice (C). Subsets of TAMCs (M, M-MDSC; P, PMN-MDSC; T, TAM) were analyzed by abundance (D) and percentage (E). PD-L1 expression on TAMCs was determined by percentage of PD-L1 positive population (F) and MFI (G). Data are represented as mean±SEM; n=3-4. (H) The experimental workflow of combination therapy through intranasal delivery. (I) Survival curves of mice received intracranial implantation of $5\times10^4$ GL261 glioma cells and eight administrations of saline or αPD-L1-LNP/Dina (5 mg/kg Dina) through intranasal approach. n=8 mice per group. (J) Survival curves of mice received intracranial implantation of $5\times10^4$ CT2A glioma cells and two administrations of saline or αPD-L1-LNP/Dina (2.5 mg/kg Dina) through intracranial cannula system. n=10 mice per group. *, $p<0.05$; , $p<0.01$; *, $p<0.001$; determined by one-way ANOVA with Tukey's multiple comparisons test (in C, D, and G), or Log-rank method with p values adjusted by Bonferroni correction (in B, I, and J).
Figure 6:
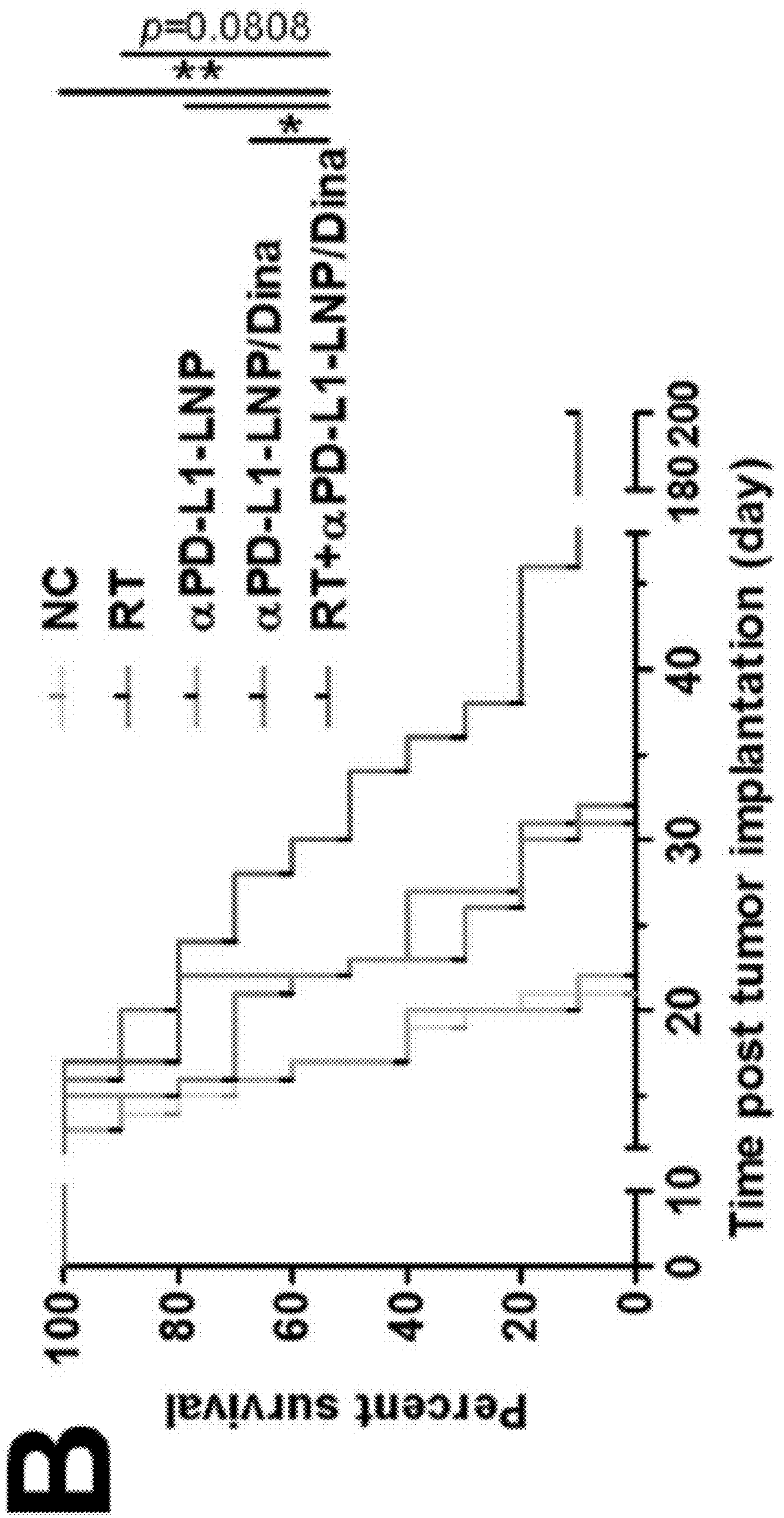
Figure 6:
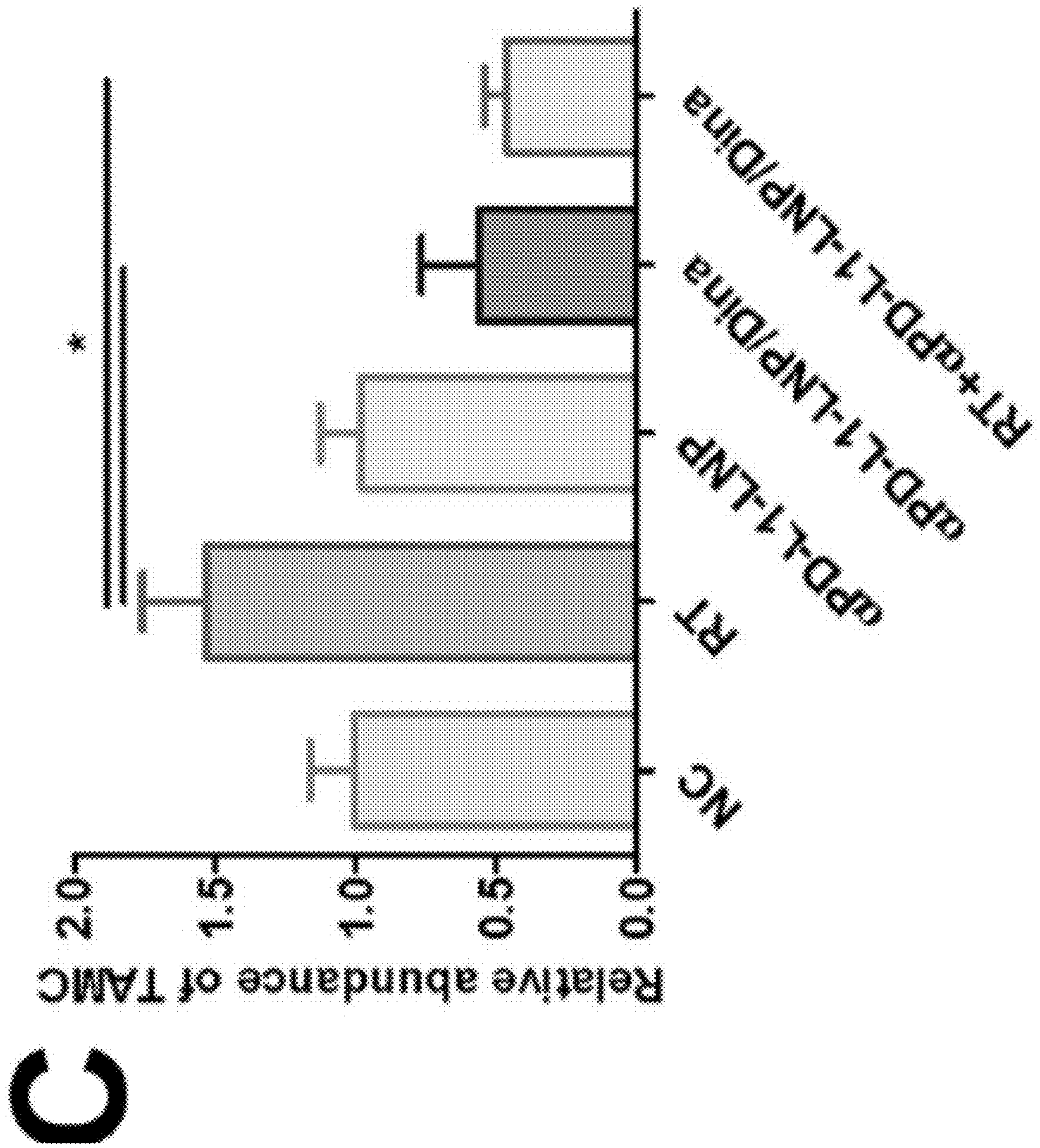
Figure 6:
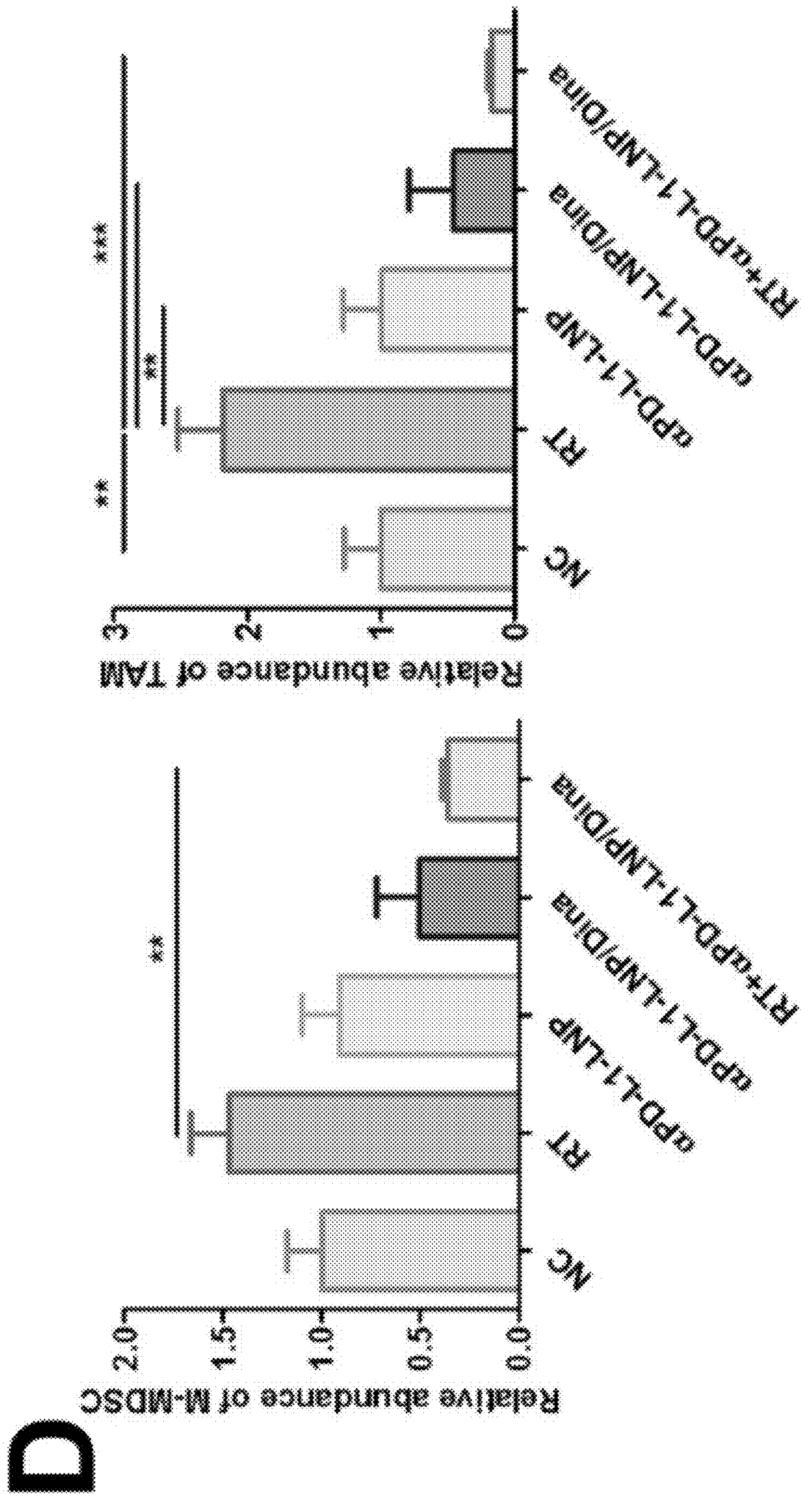
Figure 6:
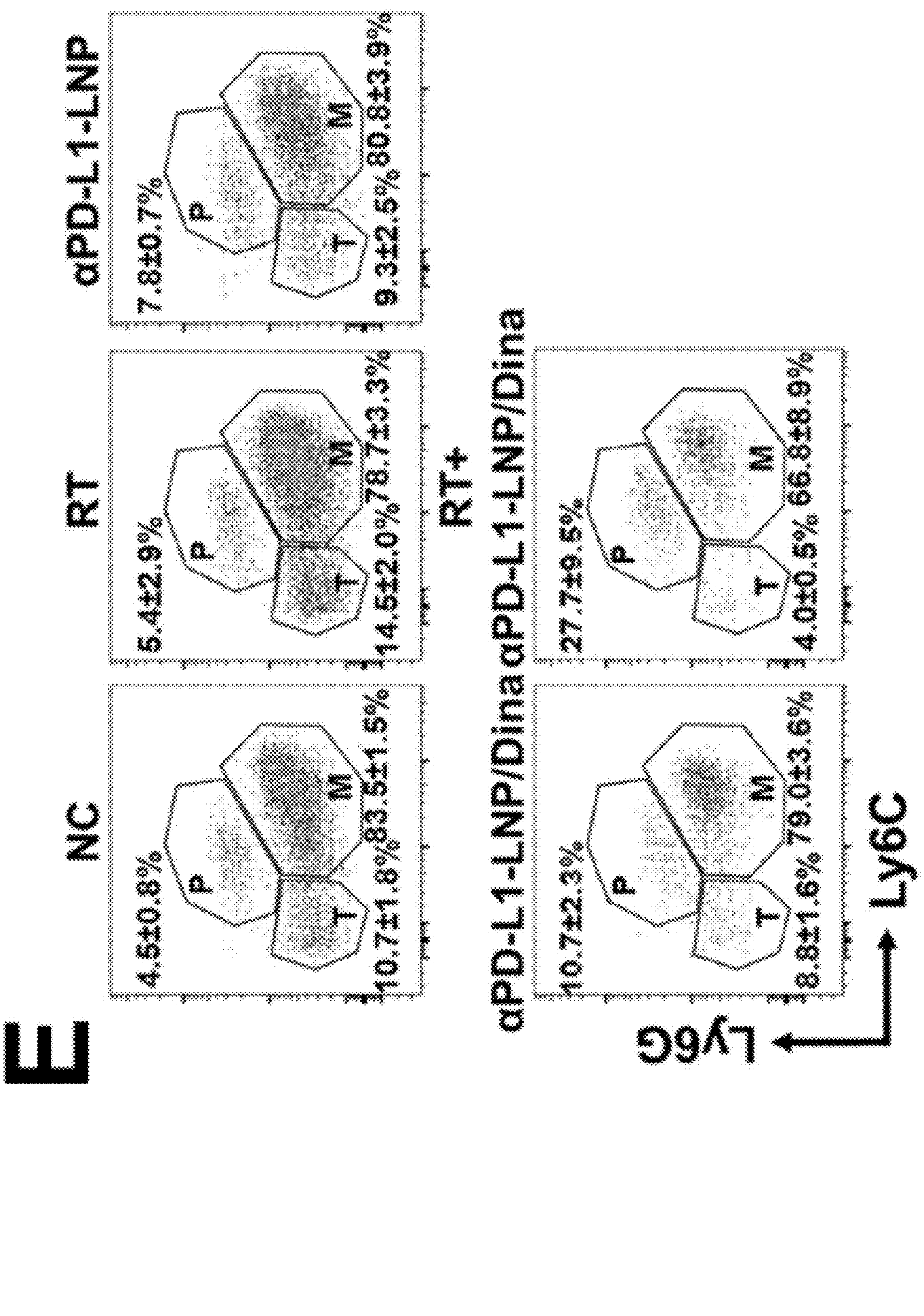
Figure 6:
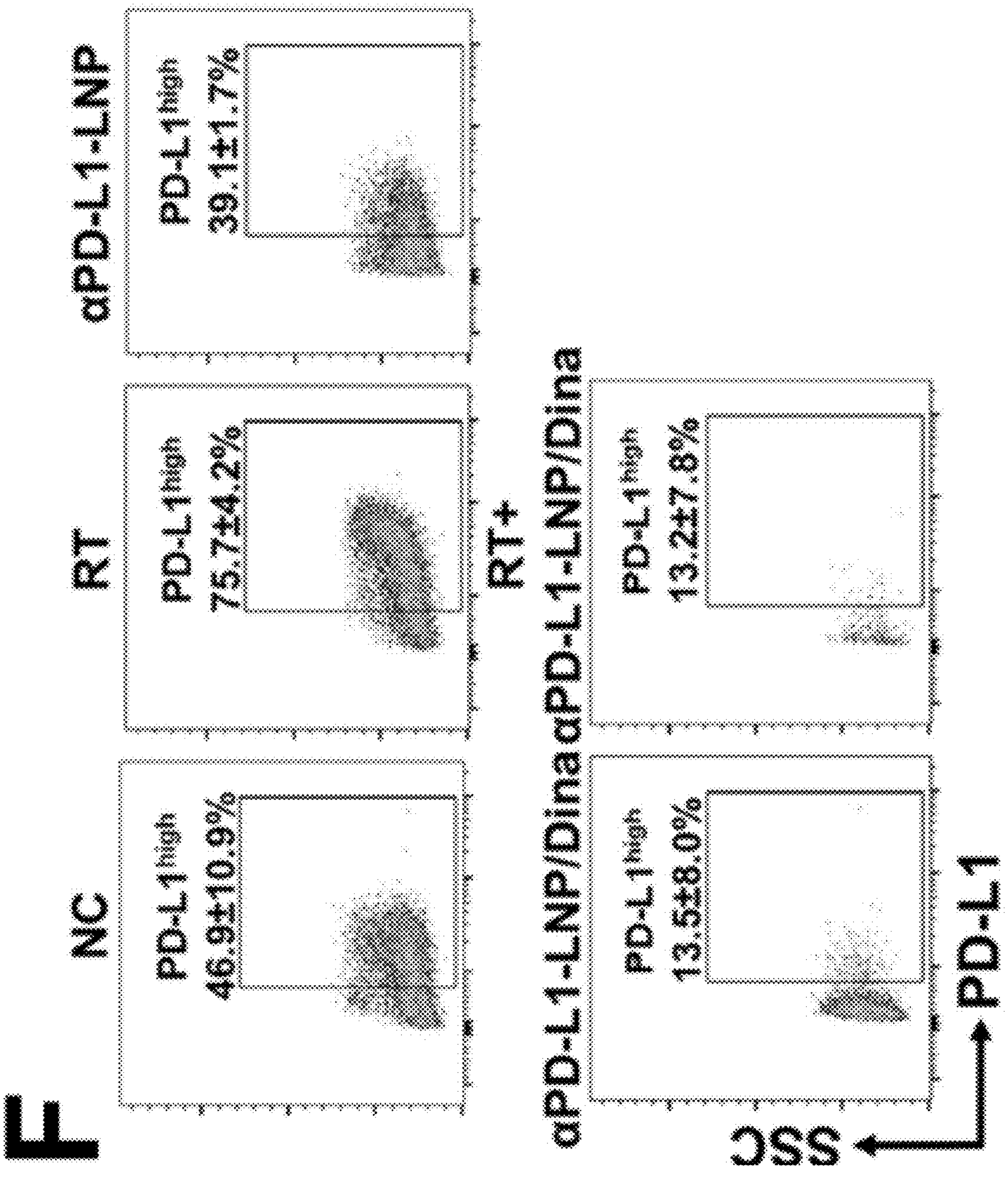
Figure 6:
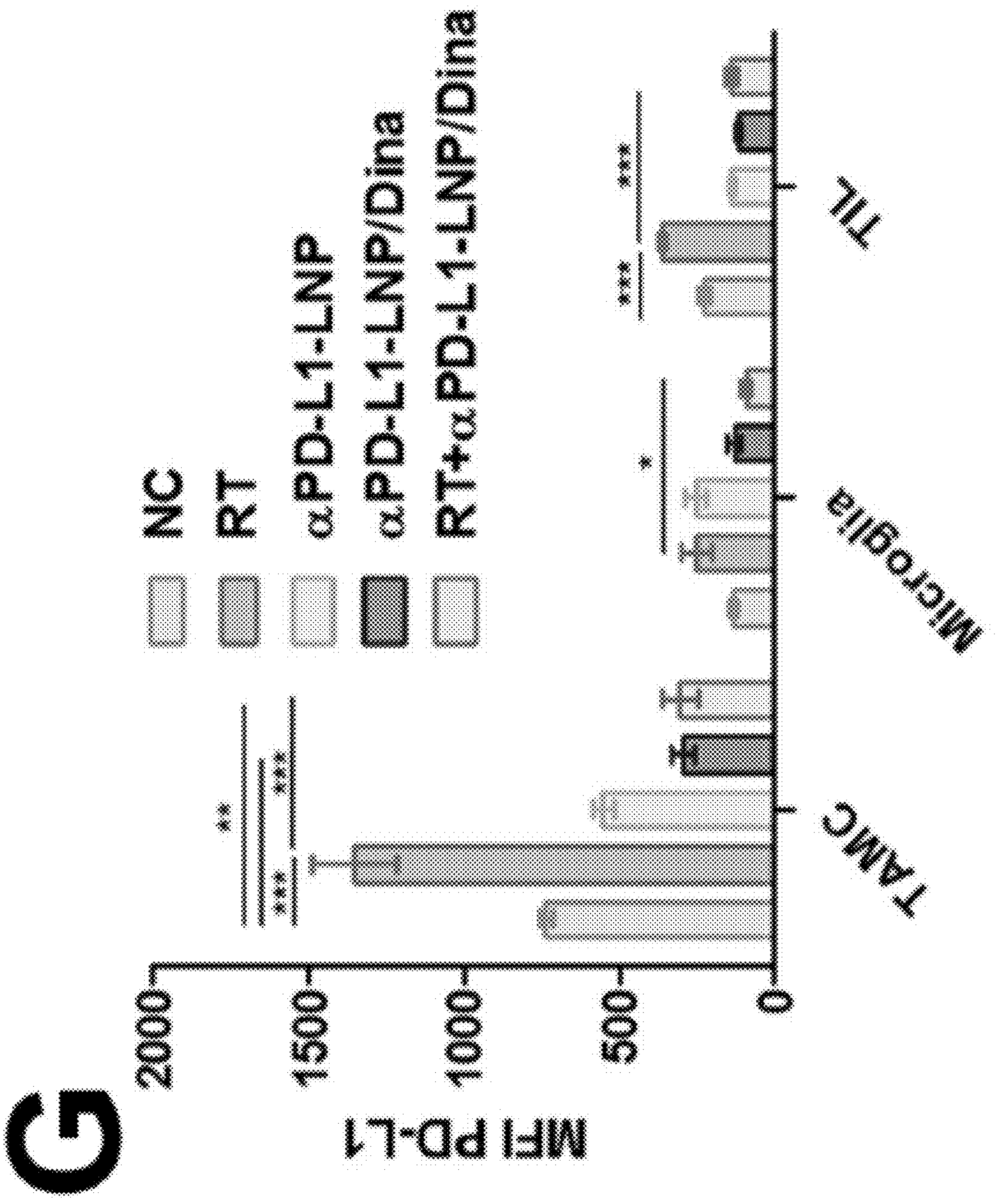
Figure 6:
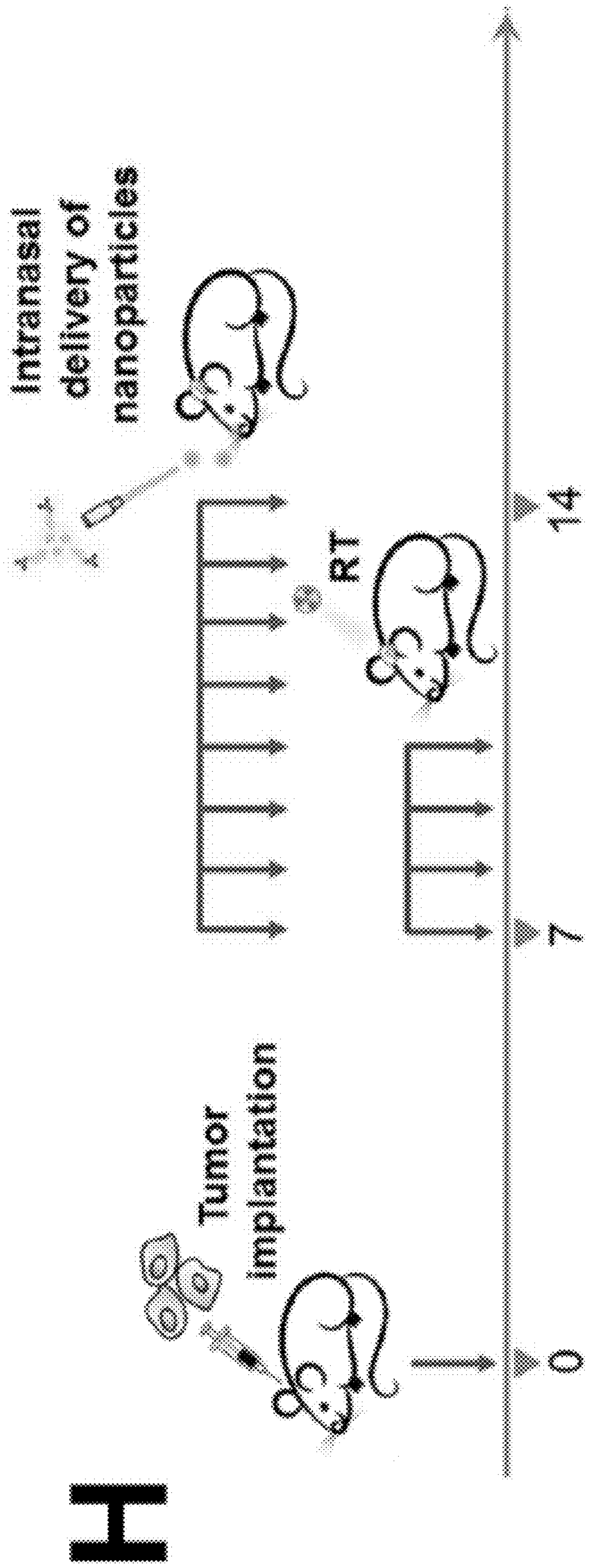
Figure 6:
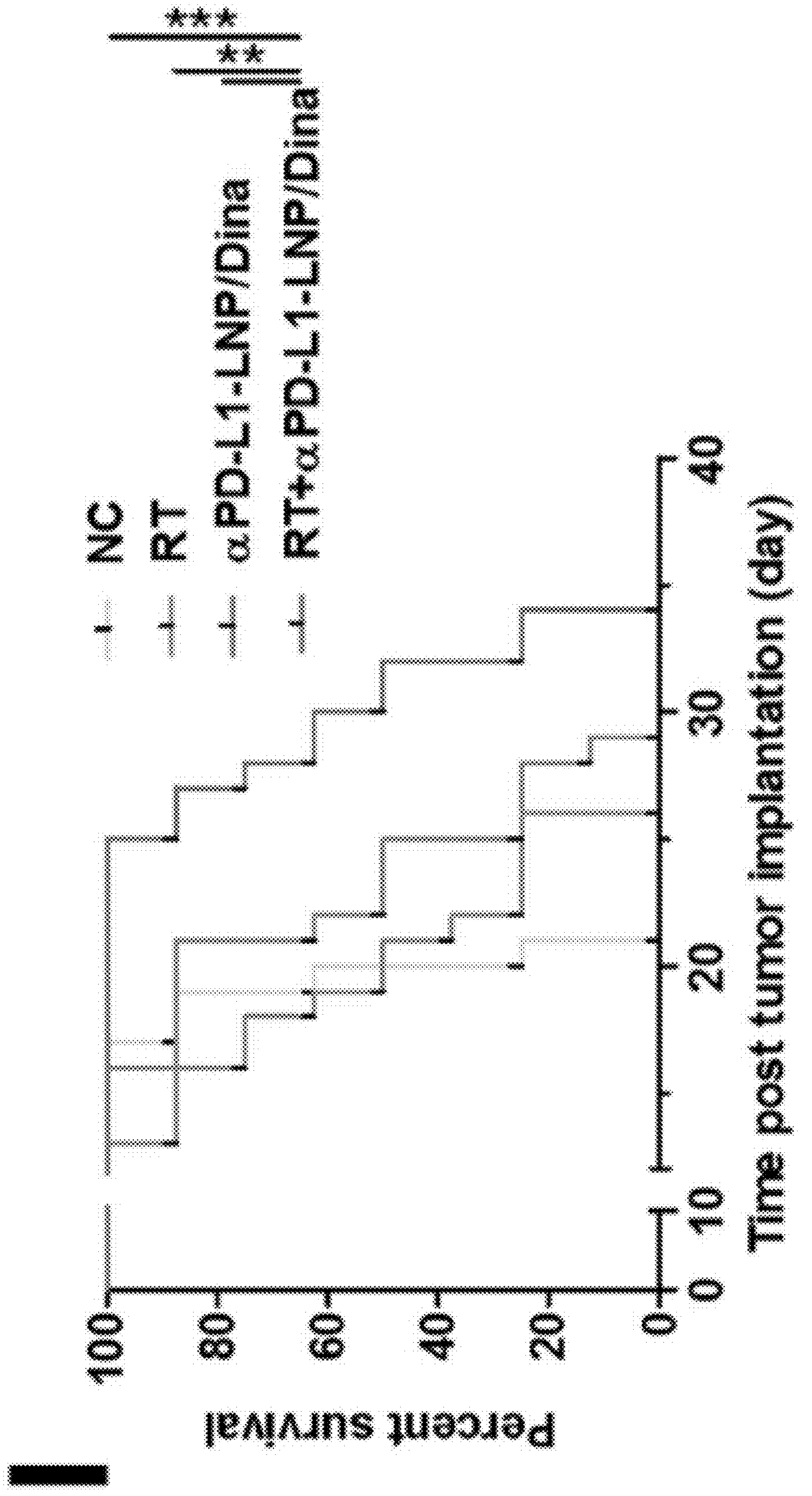
Figure 6:
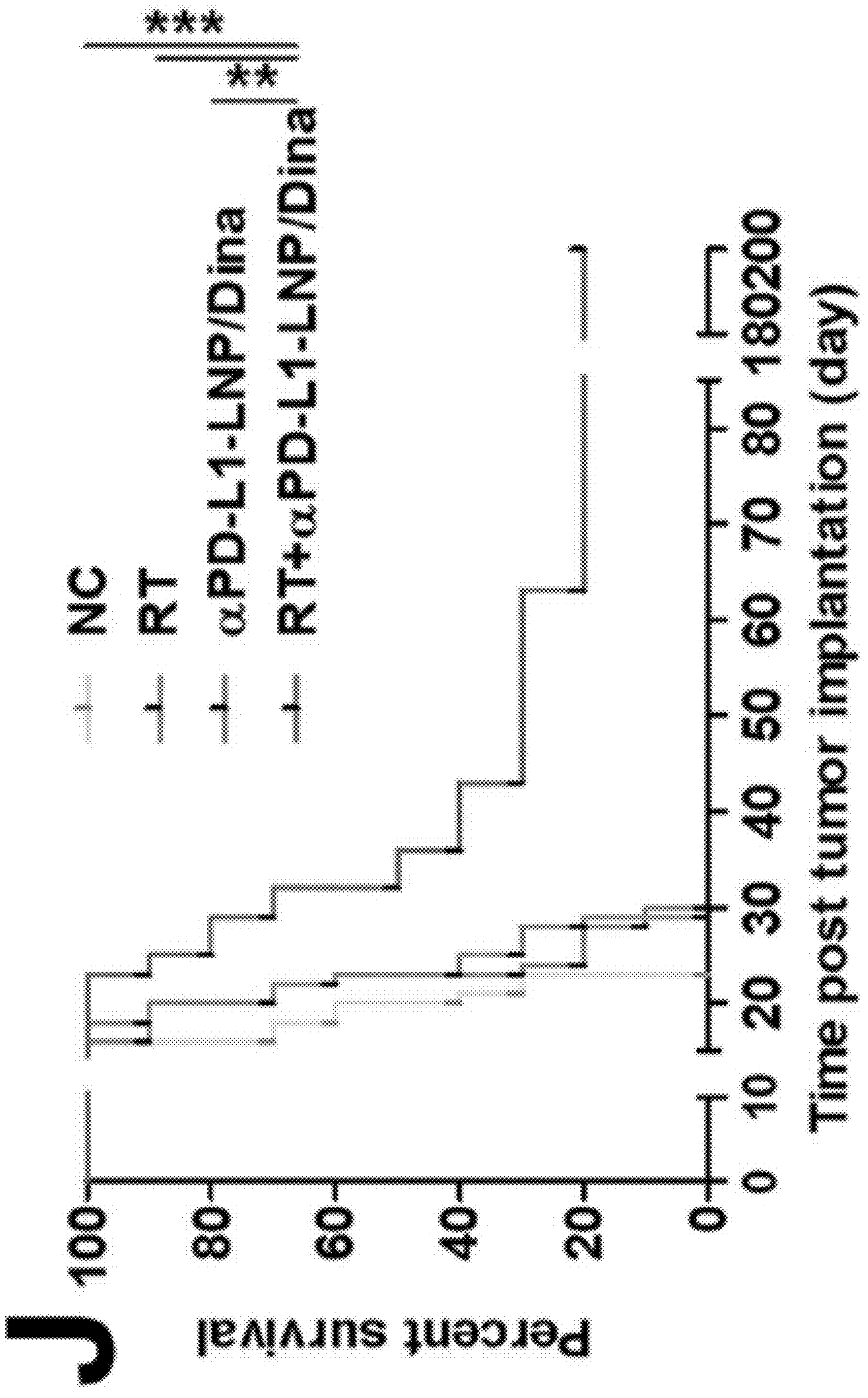
Figure 24:
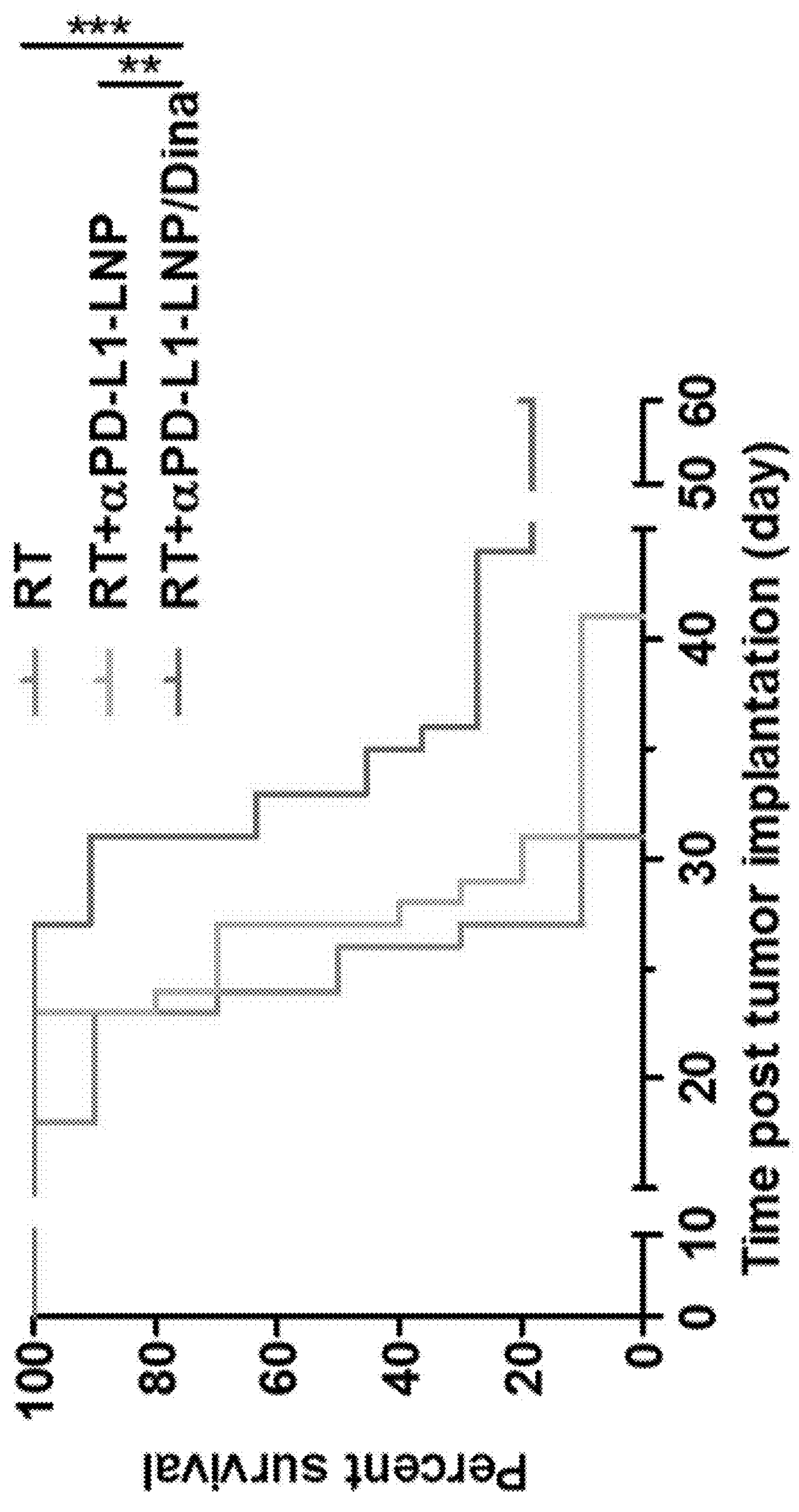
FIG. 24. Survival curves of GL261-bearing mice after combination therapy. Mice were intracranially inoculated with $2\times10^5$ GL261 glioma cells, given two administrations of saline, drug-free αPD-L1-LNP, or αPD-L1-LNP/Dina (2.5 mg/kg Dina) on the seventh and fourteenth day post tumor cell implantation, and exposed to a 2 Gy daily dose of irradiation for four consecutive days starting on the seventh day after tumor cell implantation. n=10-11 mice per group; , p<0.01; *, p<0.001; determined by Log-rank method with p values adjusted by Bonferroni correction.
Figure 25:
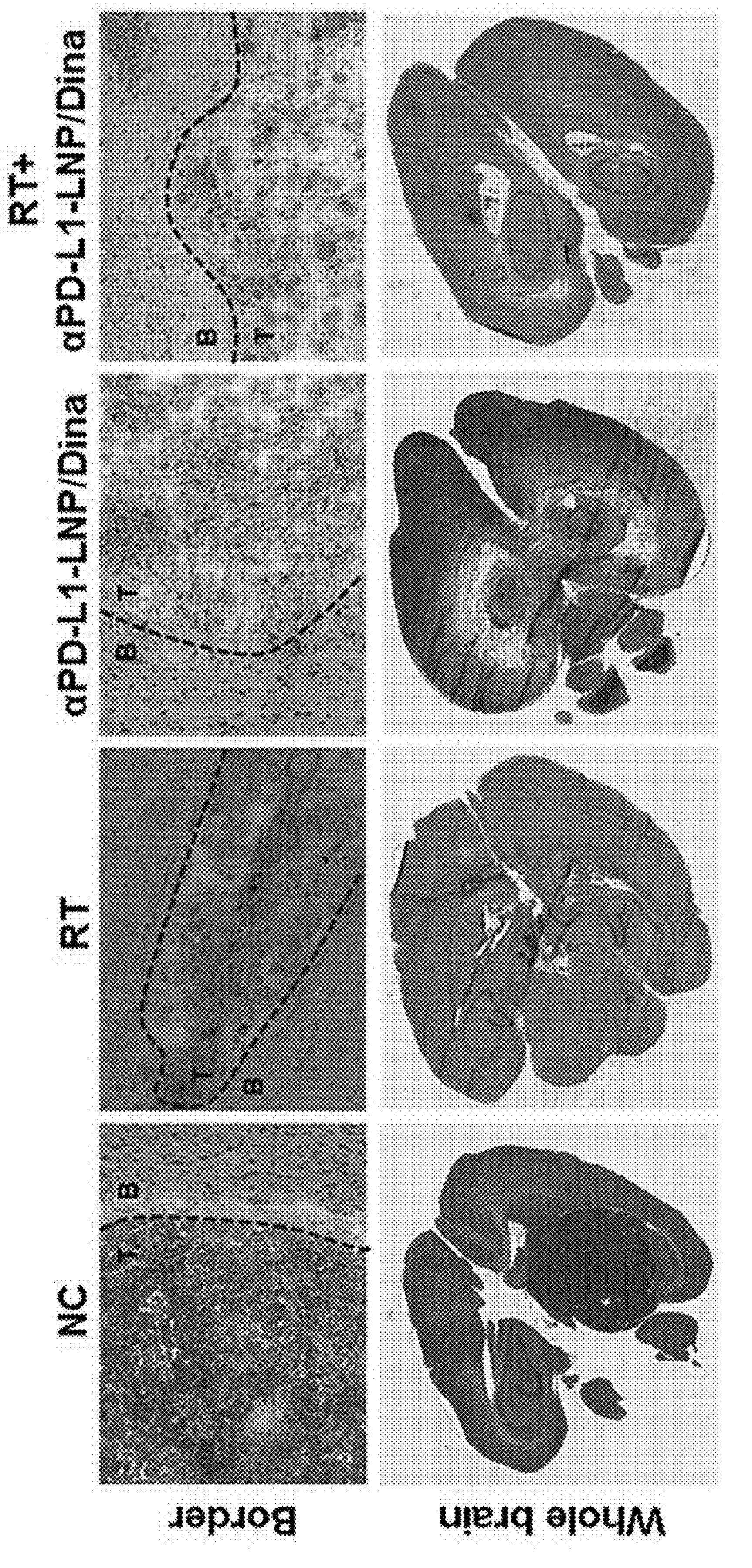
FIG. 25. Histopathological analysis of glioma tissue after combination therapy. GL261-bearing mice were intracranially inoculated with $2\times10^5$ GL261 glioma cells and given two administrations of saline or αPD-L1-LNP/Dina (5 mg/kg Dina). Selected groups of mice received RT (2 Gy×4) as monotherapy or combination therapy. Tissue sections were analyzed by H.E staining. Dotted line indicates the border of normal brain tissue (B) and tumor site (T).

Therapeutic LNPs synergize with radiation therapy to eliminate TAMCs and promote antitumor response in glioma-bearing mice. To test the potential of using TAMC targeting therapeutic LNPs as a combination therapeutic strategy with RT, different treatment regimens were assessed in C57BL/6 mice bearing GL261 glioma model (FIG. 6A). Compared to RT monotherapy, combination with drug-free αPD-L1-LNPs provided limited improvement in animal survival; however, encapsulation of Dina into αPD-L1-LNPs significantly enhanced the therapeutic efficacy of RT (FIG. 24). We then generated a more aggressive glioma model in C57BL/6 mice by increasing the number of inoculated GL261 glioma cells by 4-fold. As shown by FIG. 6B, a short lifespan was observed in control group of mice with a median survival of only 17 days. Monotherapy, either four daily 2 Gy fractions of irradiation or two injections of αPD-L1-LNP/Dina, moderately improved animal survival to 22.5 days. However, combination therapy extended the median survival of GL261 bearing mice to 32 days, a two-fold increase in comparison to control group. The treatment induced apoptosis/necrosis of glioma cells and decreased tumor size were also indicated by histopathological analysis of glioma tissue (FIG. 25).

Figure 26:
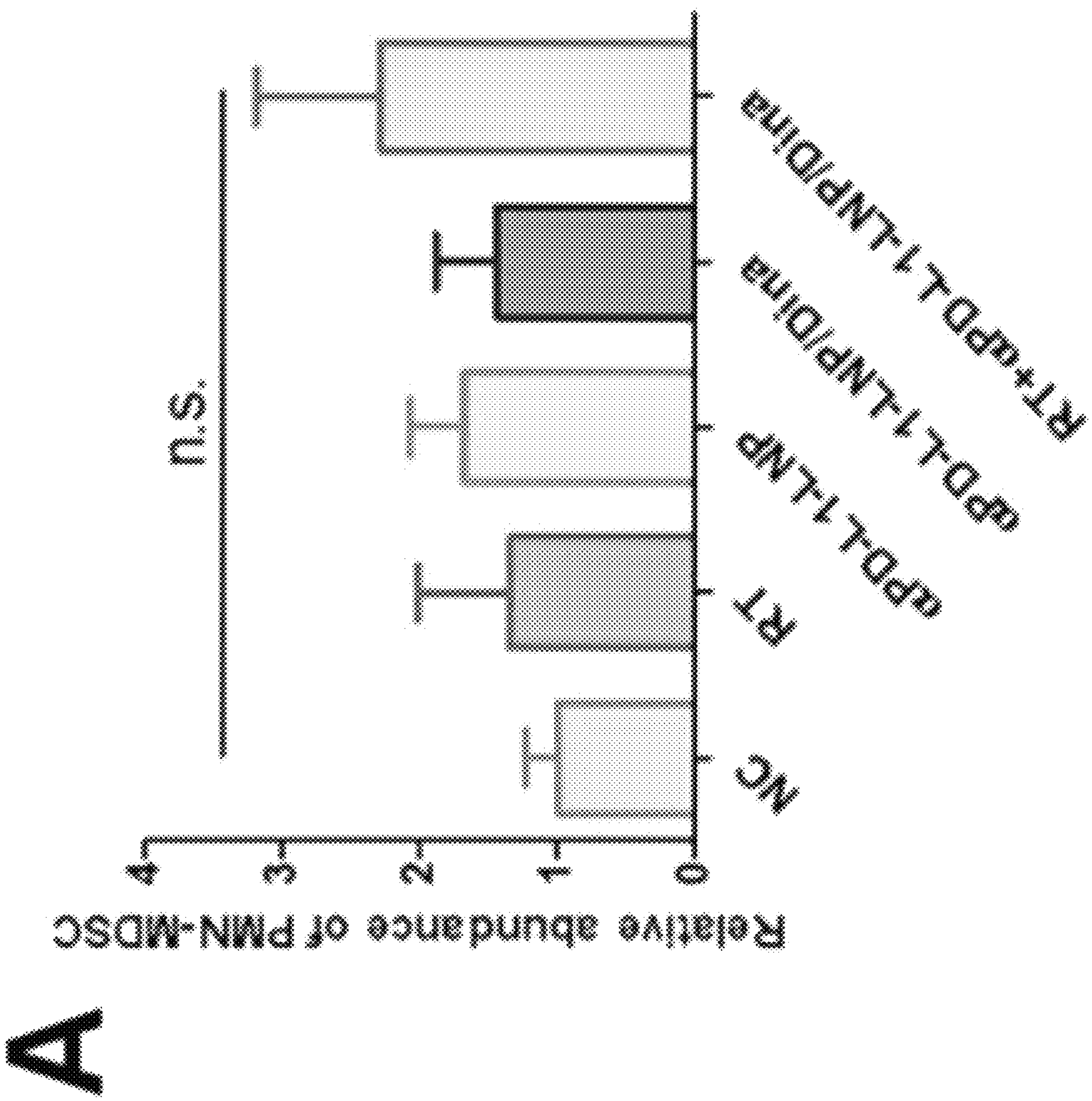
FIG. 26. Flow cytometric analysis of tumor-infiltrating immune cells in mouse brains bearing GL261 glioma. The abundance of PMN-MDSCs was analyzed by cell counts and flow cytometry, as normalized to control mice (A). Subsets of MDSCs were analyzed by ratio changes (B). The abundance of $CD4^+$ $Foxp3^+$ Treg was reported relative to control mice (C), and analyzed by $CD4^+$ $Foxp3^-$ effector CD4 T cell/$CD4^+$ $Foxp3^+$ Treg ratio (D). Data are represented as mean±SEM; n=3-4; *, p<0.05; , p<0.01; *, p<0.001; n.s., not significant; determined by one-way ANOVA with Tukey's multiple comparisons test.
Figure 26:
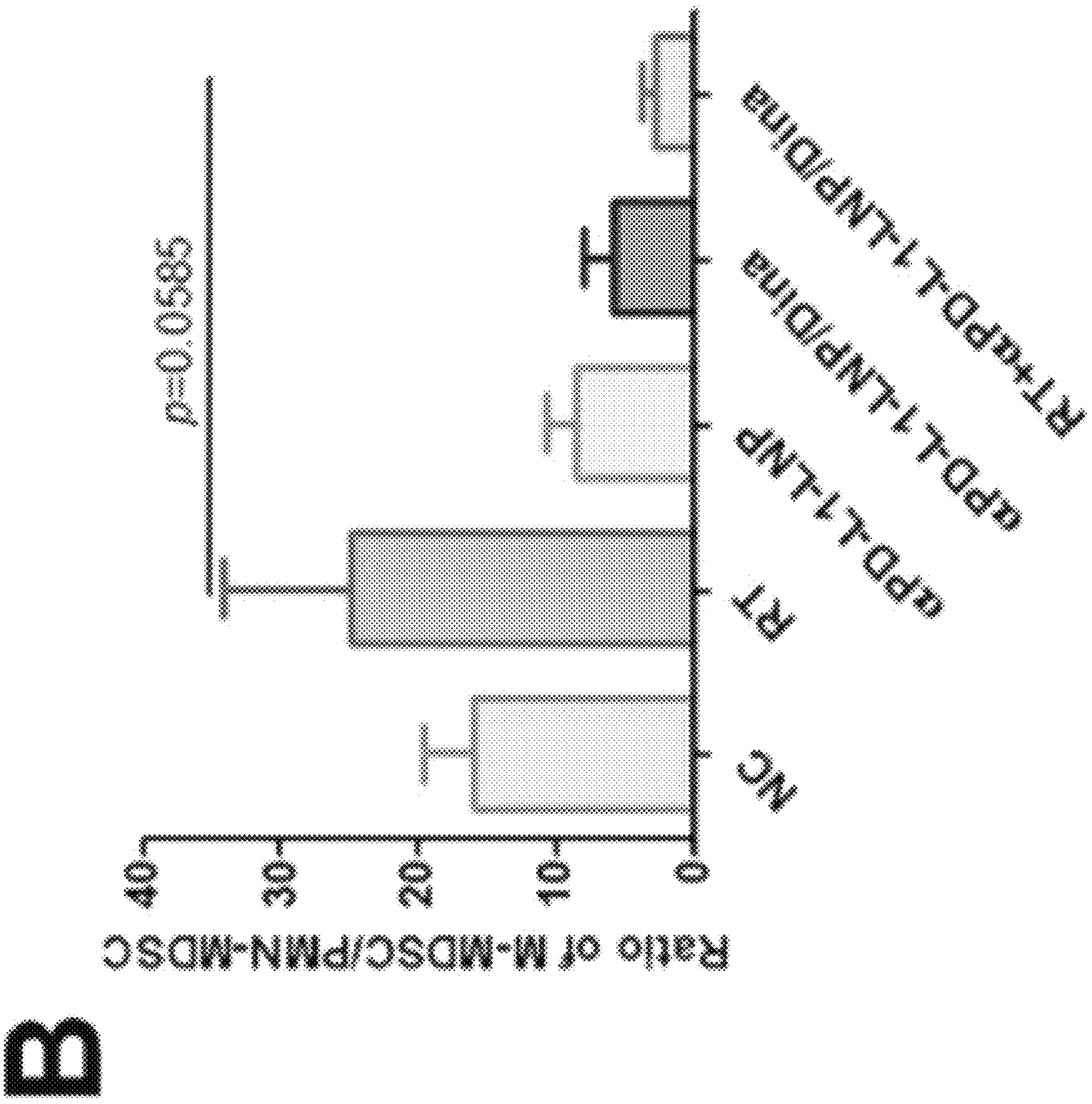
Figure 26:
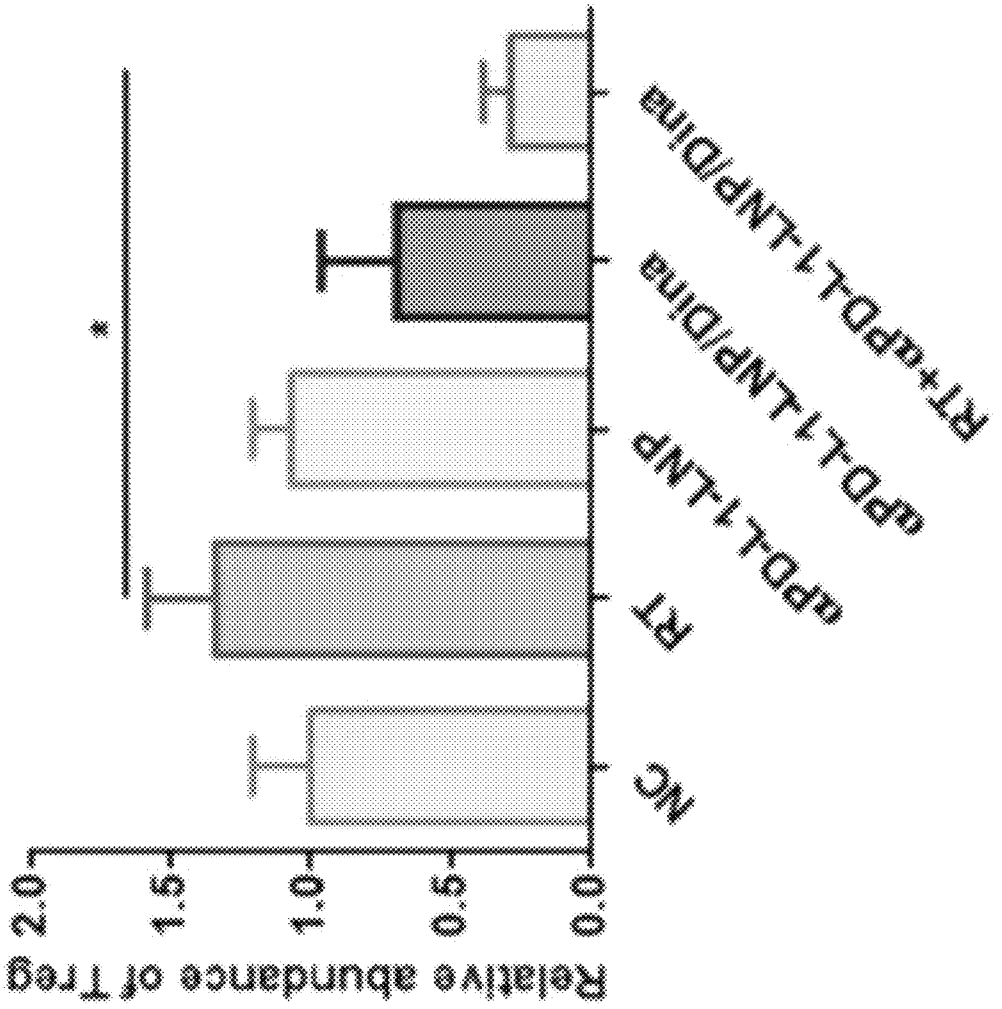
Figure 26:
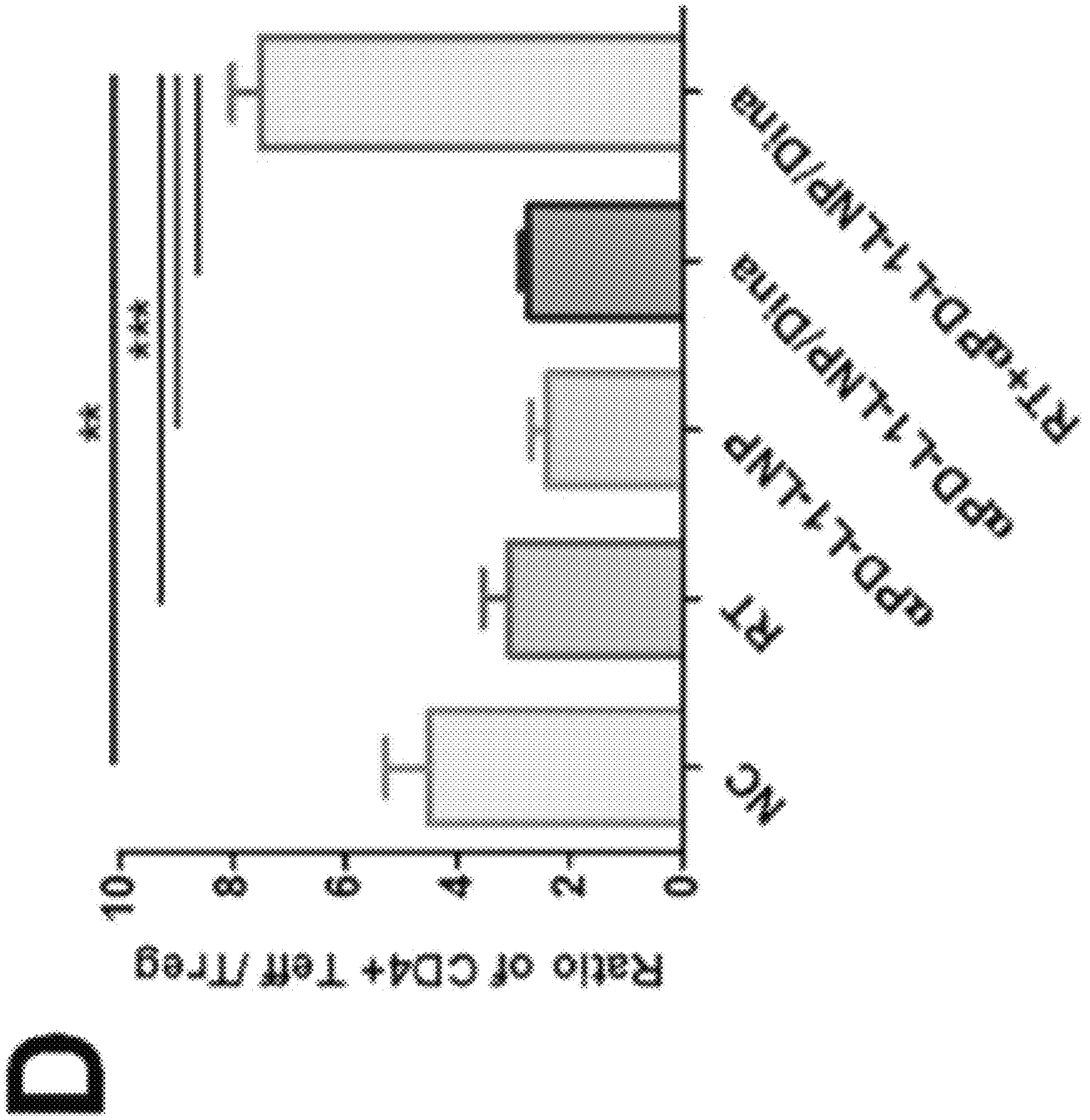

The ability of treatments to shape immunosuppressive TME was also assessed in GL261 glioma-bearing mice. RT largely caused infiltration of TAMCs into glioma, which were dramatically eliminated by treatment with αPD-L1-LNP/Dina (FIG. 6C), particularly M-MDSCs and TAMs (FIGS. 6D and E), whereas the treatment had no significant effect on PMN-MDSCs (SI Appendix, FIG. 26). Such elimination was heavily relied on PD-L1 targeted therapeutic delivery. PD-L1 expressing TAMCs were almost depleted after two injections of αPD-L1-LNP/Dina (FIG. 6F), and remaining TAMC subset demonstrated low level of PD-L1 expression (FIG. 6G). As a result of elimination of TAMCs, abundance of Treg was also profoundly reduced, which is consistent with in vitro and ex vivo data, without dramatically affecting $CD4^+$ T effectors (FIG. 26).

To foster a rapid clinical translation of these nanoparticle formulation, we also administrated the therapeutic LNPs through a non-invasive intranasal delivery approach (FIG. 6H). Similar to the results of intracranial delivery, a regimen combing intranasally administrated αPD-L1-LNP/Dina daily for eight days with four doses of irradiation led to an improved animal survival in GL261 glioma model over monotherapies (FIG. 6I). Besides, the described nano-immuno-radiation combination therapy regimen (FIG. 6A) was also evaluated in mice bearing a different syngeneic glioma model termed CT2A (FIG. 6J). CT2A is well known as an aggressive murine glioma model with brain tumor stem cell (BTSC)-like properties (40). Indeed, monotherapies did not seem to work well and only showed marginal therapeutic effects. However, excitingly, the combination therapy contributed to a largely extended animal survival compared to control group (34 days vs. 20 days), and 30% of glioma-bearing animals were observed to have long time survival.

αPD-L1-LNPs show high targeting efficiency towards human TAMCs from GBM patients. To evaluate the potential of our TAMC targeting strategy for clinical translation, targeting efficiency of αPD-L1-LNPs was tested in human TAMCs, which were harvested from from GBM patients with diverse demographic, treatment, and molecular characteristics (Table 1). Consistent with the results from murine glioma models, a more prevalent population of $CD11b^+$ $CD33^+$ $CD14^+$ M-MDSCs over $CD11b^+$ $CD33^+$ $CD15^+$ PMN-MDSCs was observed in human GBM samples (FIG. 7B), which is a unique characteristic of GBM in comparison to most types of cancers. The clinical tumor/blood samples were collected Consistent with the results from murine glioma models, a more prevalent population of $CD11b^+$ $CD33^+$ $CD14^+$ M-MDSCs over $CD11b^+$ $CD33^+$ $CD15^+$ PMN-MDSCs was observed in human GBM samples (FIG. 7B), which is a unique characteristic of GBM in comparison to most types of cancers.

Figure 7:
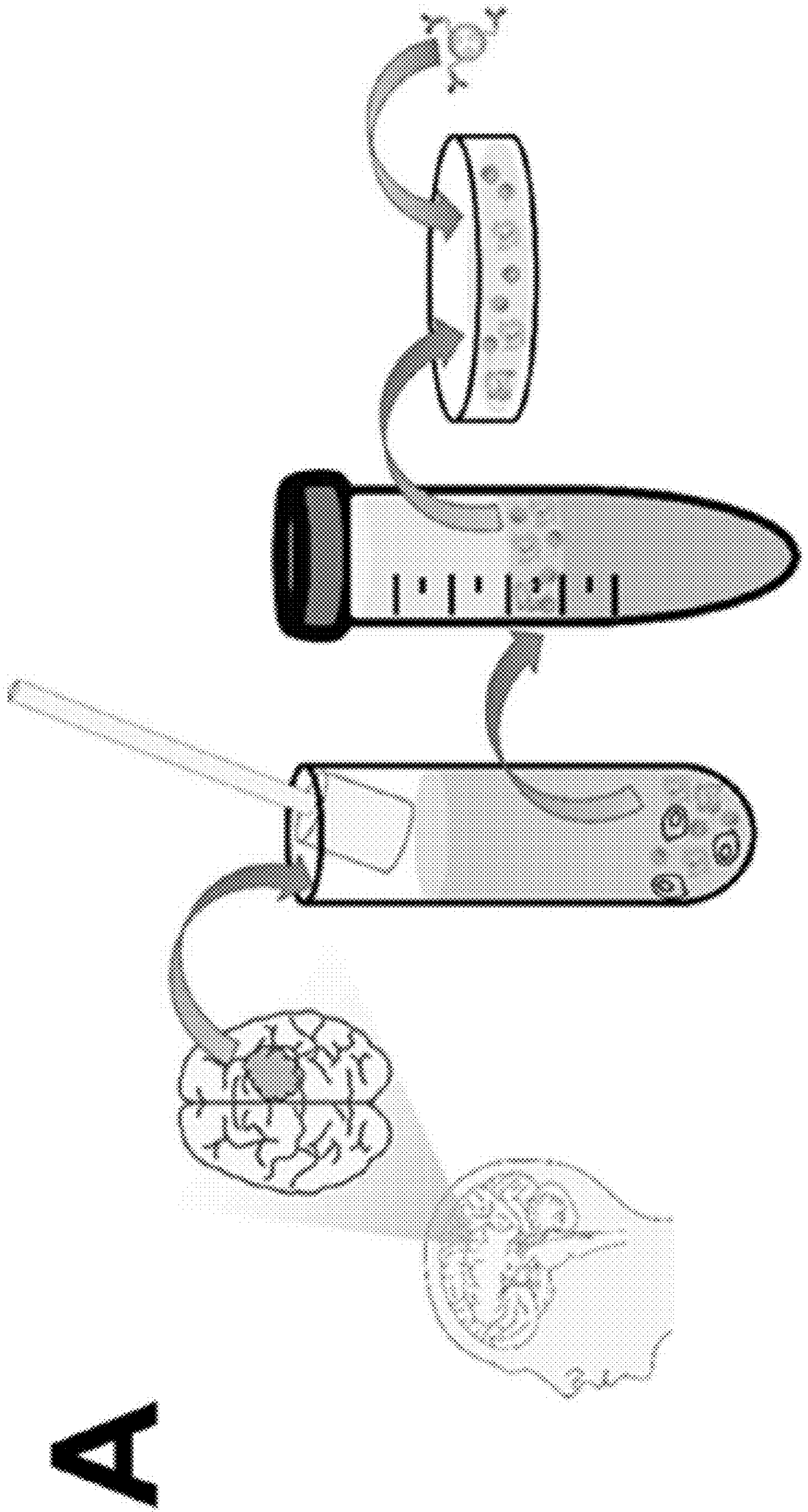
FIG. 7. αPD-L1-LNPs actively target human TAMCs from GBM patients. (A) Schematic of immune cell isolation from tumor samples of GBM patients. (B) Gating strategy and percentage of MDSC subsets in the tumor sample. (C-E) Flow cytometric analysis of PD-L1 expression (C) and cellular uptake of Rhod-PE labeled LNPs (D-E) in tumor-infiltrating myeloid cells in GBM case NU02056. The results were analyzed by NP positive population (D) and MFI (E). (F-G) Flow cytometric analysis of PD-L1 expression and cellular uptake in glioma-associated myeloid cells (F) and PBMCs (G) in GBM case NU02033.
Figure 7:
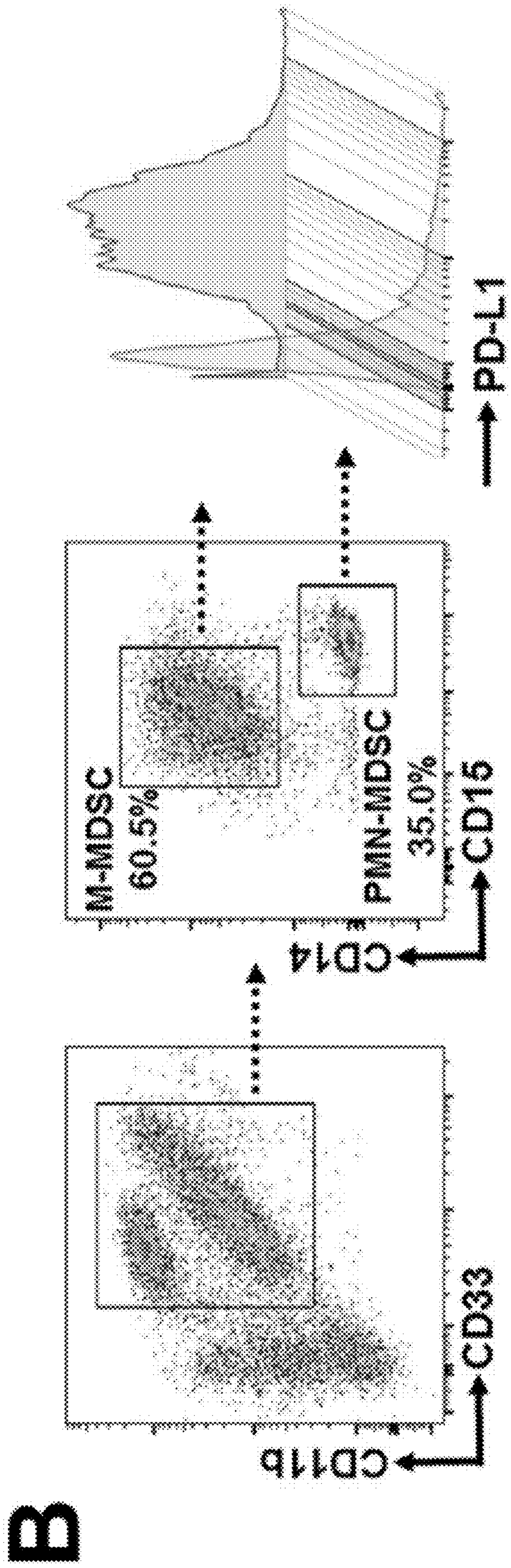
Figure 7:
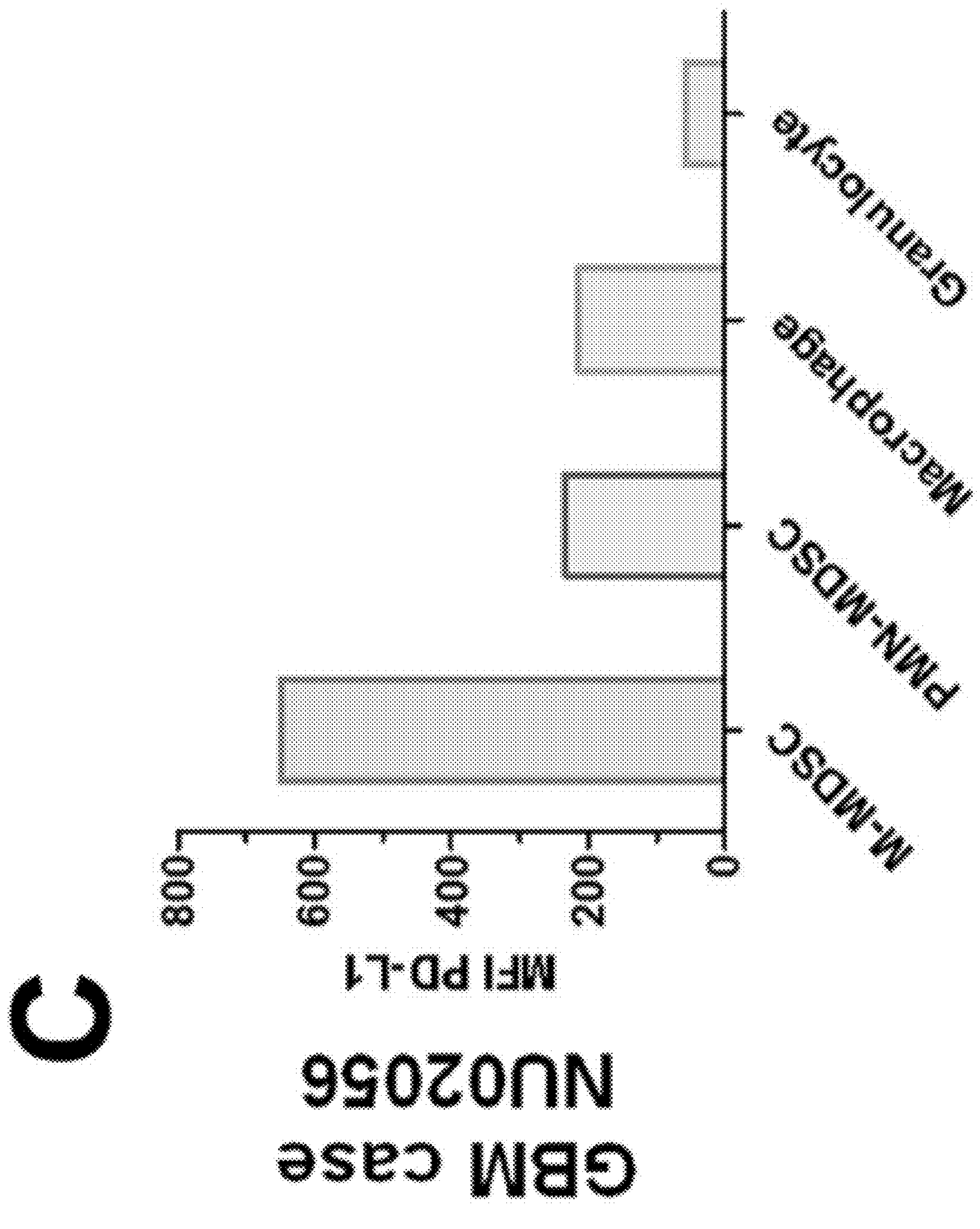
Figure 7:
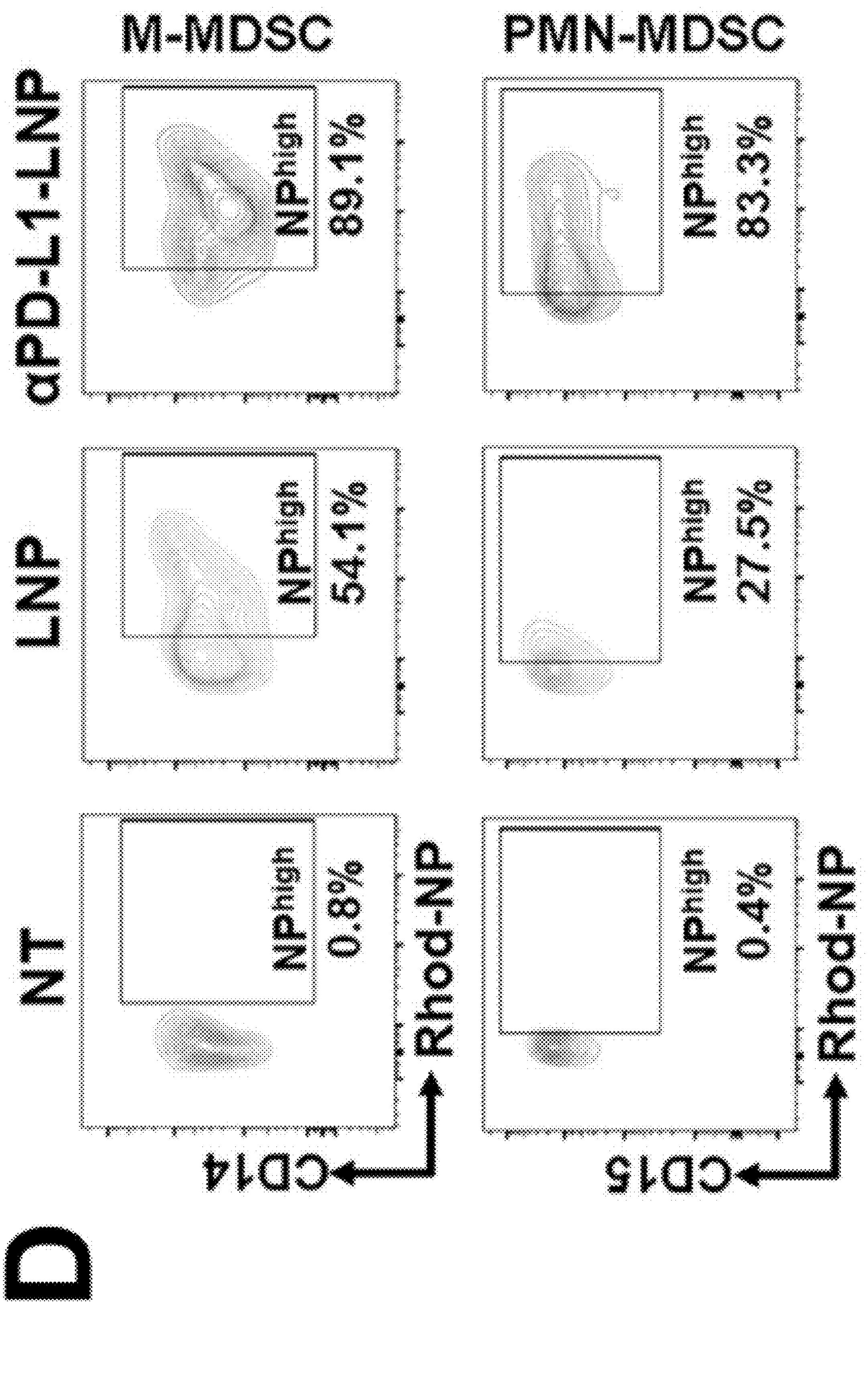
Figure 7:
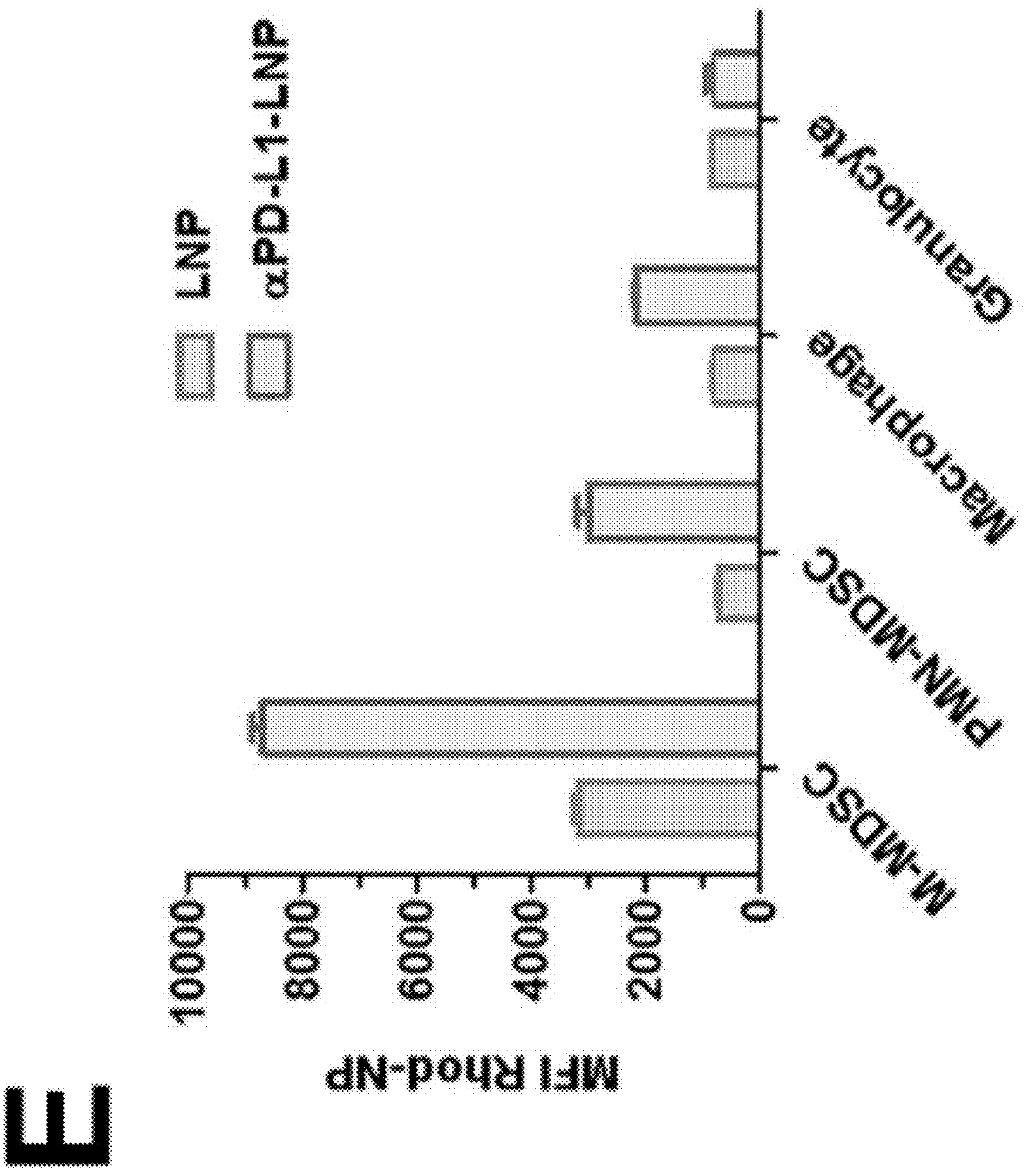
Figure 7:
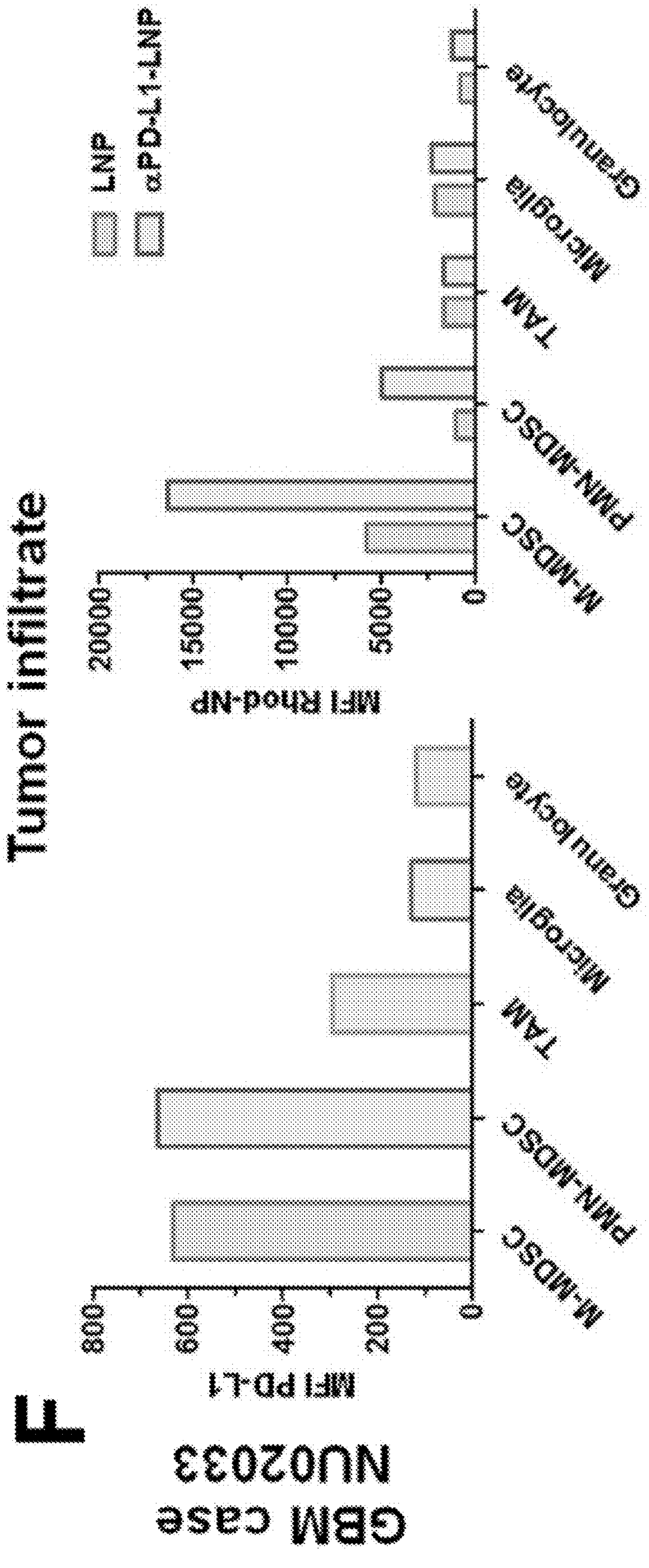
Figure 7:
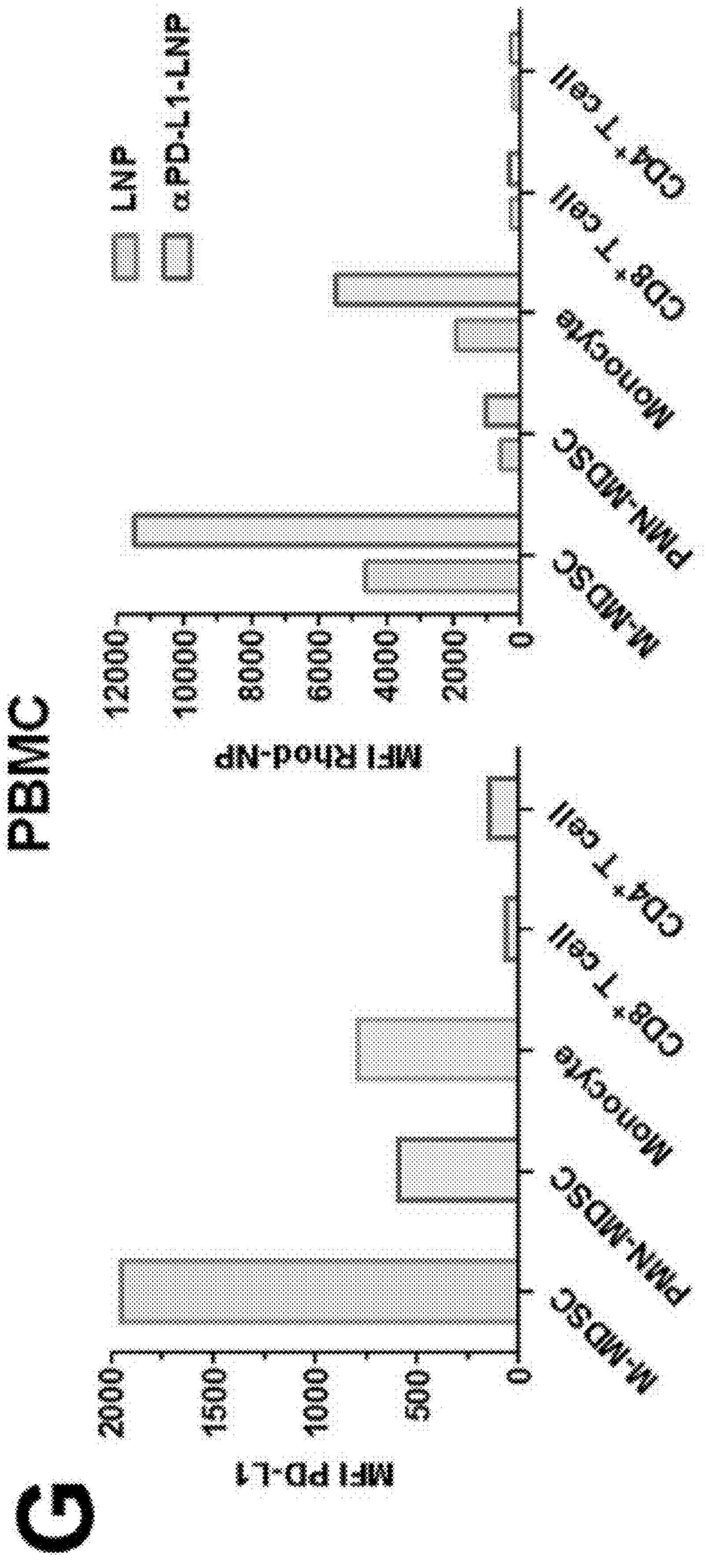
Figure 27:
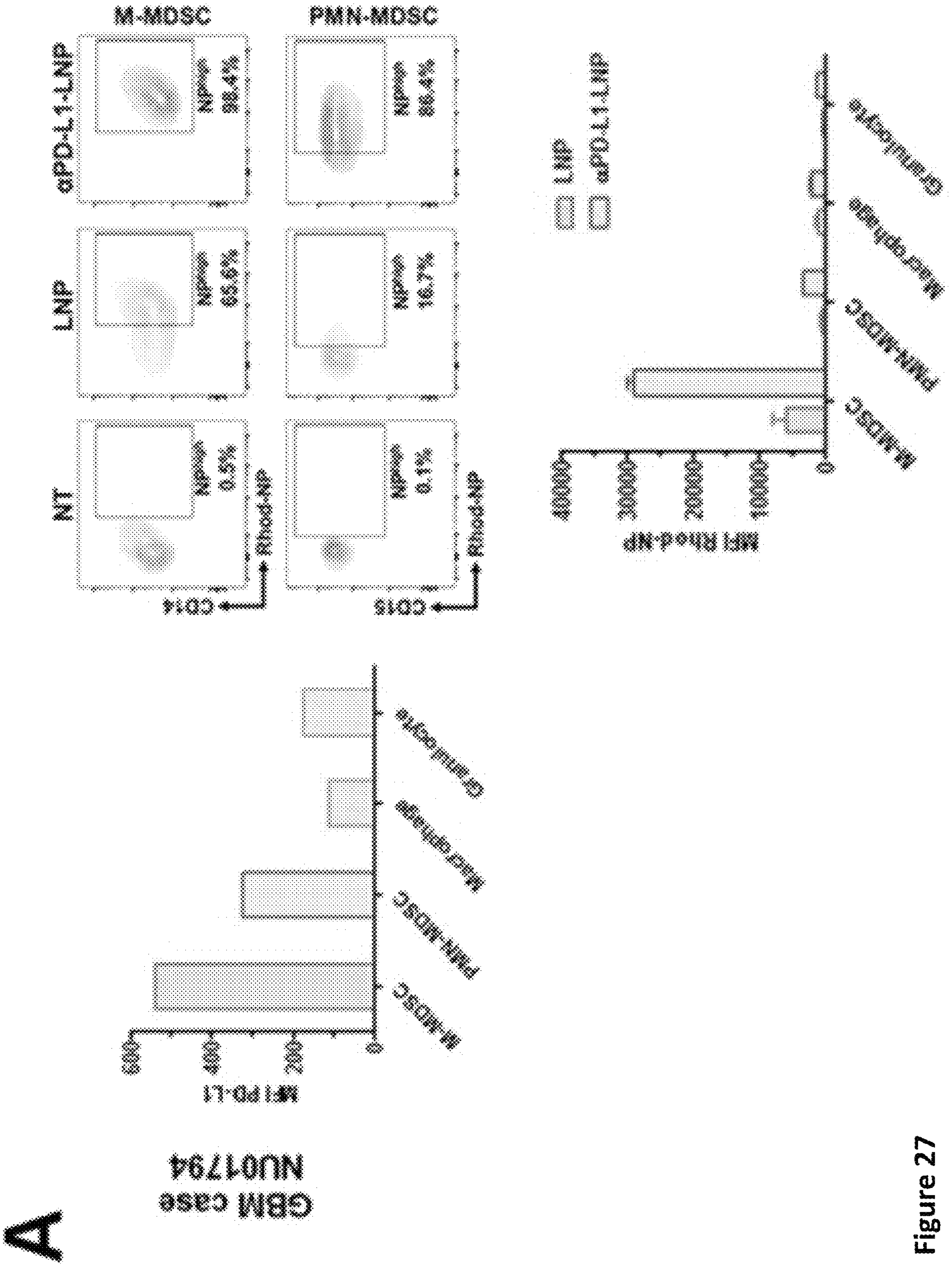
FIG. 27. Flow cytometric analysis of PD-L1 expression and cellular uptake in glioma-associated myeloid cells and PBMCs in GBM case NU01794 (A) and GBM case NU01761 (B).
Figure 27:
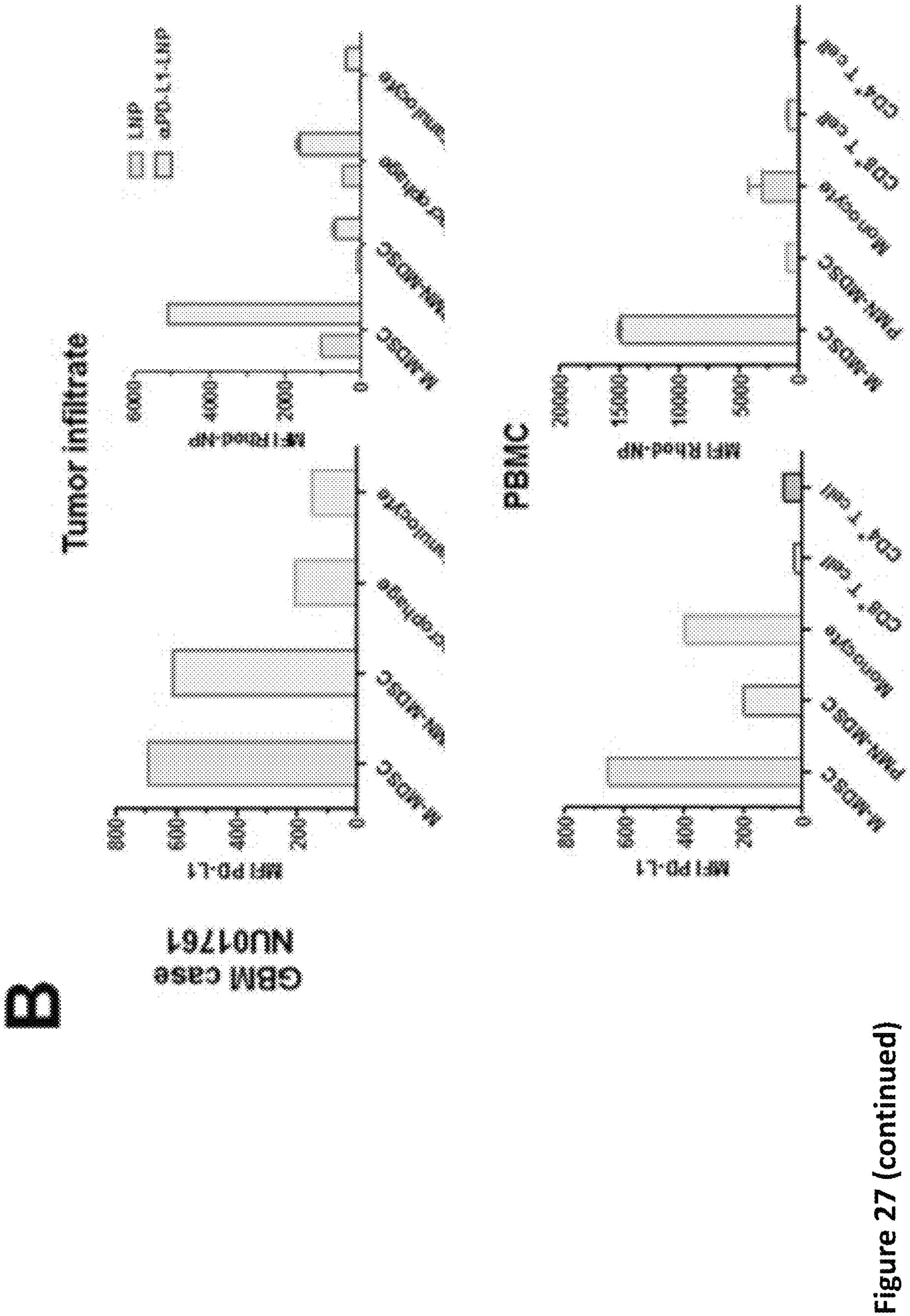

Owing to the highly expressed PD-L1 (FIG. 7C), a predominate population (~90%) of M-MDSCs, from GBM case NU02056, was effectively targeted by LNPs surface-functionalized with anti-human PD-L1 mAb, which was dramatically higher than control LNPs (FIG. 7D). Quantification by MFI further identified M-MDSCs as the primary target of αPD-L1-LNP (FIG. 7E). Comparable target specificity was observed in tumor-infiltrating myeloid cells in GBM case NU02033 (FIG. 7F). Besides, αPD-L1 also highly efficiently targeted LNPs to circulating M-MDSCs in peripheral blood of the same patient, which expressed highest PD-L1 over other subsets of peripheral blood mononuclear cells (PBMCs) (FIG. 7G). Similar characteristics with regards to PD-L1 expression and target specificity were observed in glioma-infiltrating myeloid cells as well as PBMCs in GBM case NU01794 and NU01761 (SI Appendix, FIG. 27). Collectively, these data confirm that our nanoparticles are effective in targeting human TAMCs from GBM patients, in which M-MDSCs highly expressing PD-L1 are likely the major target.

Discussion

TAMCs have been recently highlighted as a pivotal contributor to the generation of immunosuppression in the TME, tolerance to antitumor therapies, and tumor relapse and metastasis (29, 41). Thereby, they have become an attractive therapeutic target with a great potential to ameliorate tumor-associated immunosuppressive microenvironment and to unleash the full potential of antitumor therapeutic modalities. The fact that TAMCs are largely recruited into GBM to reach up to 50% of the tumor mass further emphasizes the importance and necessity of developing new approaches to therapeutically target and eliminate TAMCs for the treatment of glioma.

Progress in nanomedicine-based therapy has clearly indicated the essential role of ligand-receptor interaction-mediated therapeutic delivery to desired subset of cells. Cell-specific targeting could be readily achieved through surface-functionalization of nanoparticles with targeting ligands, including small molecules, peptides, and monoclonal antibodies, that could recognize and bind with high affinity to receptors highly expressed on cells of interest (42, 43). The research finding that PD-L1 is highly expressed on glioma-associated TAMCs lends support to the possibility that PD-L1 could be a potential novel target for therapeutic delivery towards TAMCs, which can be used to therapeutically modulate the immunosuppression in glioma TME as a nano-immunotherapy approach.

One of the major concerns about the use of PD-L1 as a target molecule for therapeutic delivery might be that there is so far no solid evidence to demonstrate binding of ligands to PD-L1 could actively trigger transmembrane transport pathways such as endocytosis in PD-L1 expressing cells, especially tumor cells. However, interaction of αPD-L1 decorated LNPs and PD-L1 on the surface of TAMCs may greatly enhance and accelerate the engulfment of nanoparticles by such cells with strong phagocytic and scavenging capabilities, as suggested by initial clues from pilot studies (44). Indeed, our PD-L1 targeted LNPs demonstrated high effectiveness and specificity in targeting TAMCs throughout comprehensive in vitro, ex vivo, and in vivo assessments. Among TAMCs, the most efficient targeting was achieved in M-MDSCs, which is consistent with the highest expression level of PD-L1 on these cells.

As a major component of TAMCs, MDSCs are characterized into two subsets: M-MDSCs and PMN-MDSCs. In most tumor models, PMN-MDSCs represent a predominant population of MDSCs, however, as a unique characteristic of GBM, M-MDSCs subset is more prevalent at tumor site (22). More importantly, recent evidence has indicated that M-MDSCs are more potent in promoting immunosuppression over PMN-MDSCs (35). Therefore, M-MDSCs have a great potential as therapeutic target with the aim to correct immune defect in glioma, and the capability of our αPD-L1-LNPs to actively target M-MDSCs indeed imparted therapeutic benefit to glioma-bearing mice. Besides M-MDSCs, αPD-L1-LNPs were also highly effective in targeting TAMs, another major component of TAMCs with highly expressed PD-L1.

A unique advantage of our therapeutic approach is the ability to recognize and deliver therapeutics to $PD\text{-}L1^+$ TAMCs. Upregulated expression of PD-L1 has been regarded as one of the major negative regulatory mechanisms deployed by TAMCs to blunt anti-tumor activity of T cells and NK cells (26, 27). Although great advances have been achieved in current anti-PD-L1 immunotherapy using checkpoint blocking antibodies, the fact that it only blocks the expressed inhibitory ligand on target cells may largely limit the overall therapeutic outcome of the treatment. To address this challenge, we created a dual-action nano-delivery system allowing a simultaneous delivery of the therapeutic antibody and drug payloads to PD-L1 expressing TAMCs. The surface engineered anti-PD-L1 antibody not only efficiently targeted LNPs to $PD\text{-}L1^+$ TAMCs, but also functionally neutralized PD-L1 on TAMCs as a therapeutic antibody. More importantly, binding of αPD-L1-LNPs, rather than unconjugated free antibodies, may largely impair endocytic recycling of PD-L1 on TAMCs by rerouting the ligand to lysosomal degradation, which is a unique mechanism of our nanoparticle system. Also, we demonstrated that the payload drug, Dina, potently inhibited IFNγ-stimulated de novo synthesis of PD-L1 in TAMCs, which further enabled a synergistic and profound inhibition of PD-L1 in TAMCs through two distinct mechanisms. The treatment of αPD-L1-LNP/Dina significantly induced cytotoxicity in TAMCs when the dose was further increased, and led to a robust depletion of TAMCs and survival benefit of glioma-bearing mice.

Another advantage of our TAMC targeted nano-immunotherapy strategy is the capability to synergize with radiation therapy. RT has been widely used in the treatment of various cancers, and particularly, as a standard of care for GBM. However, RT could dramatically induce infiltration of TAMCs into tumor site, which strongly suppresses RT-elicited immune response and is believed a crucial resistance mechanism to RT (9, 10). Interestingly, while RT induced dramatic cytotoxicity to PMN-MDSCs, radio-resistant M-MDSCs upregulated PD-L1, which actually allows for enhanced delivery of our nanoparticle treatment. Supporting this notion, administration of therapeutic nanoparticles to glioma-bearing mice post-RT caused dramatic elimination of TAMCs, particularly M-MDSCs and TAMs, leading to an extended survival of animals in two different glioma models compared to RT monotherapy. These data strongly suggest that our therapeutic nanoparticle therapy could be used as a combination therapy strategy to synergize with radiotherapy for GBM therapy.

Finally, our therapeutic nanoparticles demonstrated a great potential with respect to the rapid translation into clinical practice, relying on the high efficiency in performance and simplicity in manufacturing. LNPs, to date, are the most clinically successful nano-formulation with well demonstrated safety and efficiency (45, 46). Thus, a rapid transition from the benchtop research findings to bedside application could be expected. And excitingly, the high targeting efficiency of αPD-L1-LNPs to human TAMCs isolated from tumor and blood samples of GBM patients further validated the clinical relevance of the proposed system. Moreover, our therapeutic nanoparticle is a versatile platform that could be readily tailored by switching the payload therapeutics or surface-functionalized targeting ligands with the aim to target variable subsets of cells of interest in different disease models. And a successful attempt to administrate our therapeutic nanoparticles through intranasal delivery method further extended the potential application of our therapeutic approach in different routes of drug administration.

In summary, we have developed a viable nano-immunotherapy approach that could actively target both murine and human glioma-associated TAMCs, and lead to robust TAMC depletion and attenuation of their immunosuppressive functions. This nanomedicine platform establishes a new therapeutic strategy with great potential to improve the clinical response in the treatment of GBM, and holds great promise for a rapid translation into clinical application.

Materials and Methods

LNPs were synthesized through a thin-film hydration method followed by surface-functionalization with αPD-L1. In vitro TAMCs were generated from bone marrow progenitor cells of C57BL/6 mice. Ex vivo studies were performed using immune infiltrates isolated by percoll gradient from the intracranial GL261 glioma tumors in mice. Experimental animals were mixed-gender and randomly assigned. All animal-related experiments were performed in full compliance with animal protocols approved by the Northwestern University Institutional Animal Care and Use Committee (IACUC). All human tumor and peripheral blood samples were collected by the Nervous System Tumor Bank of the Northwestern University (NSTB) under the IRB protocol No STU00202003.

Reagents. 1,2-dioleoyl-sn-glycero-3-phosphocholine (DOPC), 1',3'-bis[1,2-dioleoyl-sn-glycero-3-phospho]-glycerol (18:1 cardiolipin), 1,2-distearoyl-sn-glycero-3-phosphoethanolamine-N-[methoxy(polyethylene glycol)-2000] (DSPE-$PEG_{2000}$), 1,2-distearoyl-sn-glycero-3-phosphoethanolamine-N-[maleimide(polyethylene glycol)-2000] (DSPE-$PEG_{2000}$-maleimide), L-α-Phosphatidylethanolamine-N-(lissamine rhodamine B sulfonyl) (Rhod-PE) were purchased from Avanti Polar Lipids. Cholesterol and 2-iminothiolane hydrochloride were obtained from Sigma Aldrich. Dinaciclib (SCH 727965, Dina) was purchased from Chemietek. InVivoMAb anti-mouse PD-L1 (B7-H1, clone 10F.9G2) antibody, rat IgG2b isotype control (clone LTF-2), and anti-human PD-L1 (B7-H1, clone 29E.2A3) antibody were purchased from BioXCell.

Cell culture. GL261 murine glioma cell line was purchased from NCI. CT2A murine glioma cell line was originally obtained from Dr. John H. Sampson at Duke University. The cell lines were maintained in Dulbecco's Modified Eagle's Medium (DMEM, Fisher) supplemented with 10% fetal bovine serum (FBS, Hyclone) and 1% penicillin/streptomycin (Invitrogen) at 37° C. in a humidified environment with 5% $CO_2$.

Animals. C57BL/6 (WT) and C57BL/6-Foxp3-GFP mice were obtained from Jackson Laboratories, and bred and housed in Northwestern University animal facility. Experimental animals were mixed-gender and randomly assigned to into treatment groups. All animal-related experiments were performed in full compliance with animal protocols approved by the Northwestern University Institutional Animal Care and Use Committee (IACUC).

Synthesis and characterization of lipid nanoparticles (LNPs). LNPs were synthesized through a thin-film hydration method. Briefly, DOPC, cholesterol, 18:1 cardiolipin, DSPE-$PEG_{2000}$, and DSPE-$PEG_{2000}$-maleimide were mixed at a weight ratio of 54.6:12.8:15.6:10:7 in chloroform in a glass vial. Dina was added to the lipids solution at a weight ratio of total lipids to Dina at 10:1. Organic solvent was removed through a gentle stream of nitrogen, followed by drying in vacuum for 4 h. The obtained thin-film of lipids/Dina mixture was then hydrated in DPBS (Sigma) for 1 h and suspended by vortex to obtain an opaque solution of large sized multilamellar vesicles, which was further homogenized using a probe sonicator (Active Motif) to obtain a clear solution. Control LNPs without further surface engineering of antibody (LNP/Dina) were prepared similarly with a lipid formulation composed of DOPC, cholesterol, 18:1 cardiolipin, and DSPE-$PEG_{2000}$ at a ratio of 54.6:12.8:15.6:17 (w/w). Fluorescence labeled LNPs were synthesized by the lipid formulation same as aforementioned with addition of 0.75% Rhod PE.

Surface-engineering of LNPs was performed by covalent conjugation of anti-mouse or anti-human PD-L1 antibody (αPD-L1). Briefly, αPD-L1 was reacted with 2-iminothiolane at a molar ratio of 1:10 in DPBS (pH 8.0, 4 mM EDTA) at room temperature for 1 h. The antibody was purified and concentrated using Amicon Ultra-15 (MWCO: 10 kDa, Millipore), followed by incubation with LNPs containing DSPE-$PEG_{2000}$-maleimide in DPBS (pH 7.0) at a ratio of 66 μg αPD-L1 per mg lipids for overnight at 4° C. The obtained αPD-L1-LNP/Dina was then purified and concentrated by centrifugation. The amounts of conjugated αPD-L1 were then measured by a protein assay (BCA protein Assay Reagent, Pierce). Control LNPs surface conjugated with isotype control antibody (IgG2b) were prepared similarly. The particle size distribution of synthesized LNPs was measured by dynamic light scattering (DLS) using a Zetasizer Nano ZSP (Malvern Panalytical), and presented as diameter in nm and polydispersity index (PDI). The surface charge was determined by zeta-potential using a Zetasizer Nano ZSP (Malvern Panalytical). The morphology of nanoparticles was characterized by cryo-TEM.

In vitro generation of glioma associated TAMCs. Bone marrow progenitor cells were collected from tibias and femurs of C57BL/6 mice by using a 10 ml syringe and 25 gauge needle into complete RPMI [RPMI-1640 (Corning) containing 10% FBS, 1% penicillin and streptomycin, 1% HEPES (Sigma), 1% nonessential amino acids (Gibco), 1% sodium pyruvate (Coring), and 0.1% 2-mercaptoethanol (Gibco)]. After centrifugation, red blood cells were lysed by ACK lysing buffer (Sigma) at room temperature for 5 minutes. Cells were then washed with complete RPMI, counted, and seeded into 24 well plate with a density of $2.5\times10^5$ cells per well in 50% complete RPMI and 50% conditioned media (collected from GL261 glioma cell culture 72 h post original seeding with $2\times10^6$ GL261 cells), with the addition of GM-CSF (PeproTech) at 40 ng/ul. After 3 days of culture at 37° C. in 5% $CO_2$ humidified atmosphere, media was replaced by fresh media (same as aforementioned). Cells were maintained for additional 3 days, and collected for phenotyping and in vitro study.

Isolation and activation of T cells. Splenocytes were harvested from C57BL/6-Foxp3-GFP mice, followed by pre-enrichment of T-cells using the MagniSort Mouse T cell Enrichment Kit (Invitrogen) according to the manufacturer's protocol. $CD8^+$ T cells were further enriched using biotin anti-mouse CD4 antibody for depletion (Biolegend). T cells were maintained in complete RPMI and activated with Dynabeads Mouse T-Activator CD3/CD28 T-cell expander beads (Gibco) per manufacturer's instructions, with the addition of IL-2 (PeproTech) at 50 U/ml.

In vitro TAMC targeting and intracellular trafficking. In vitro generated TAMCs ($5\times10^4$ cells/well) were seeded in 96-well plate and incubated with fluorescence labeled LNPs (0.1 mg lipids/ml) at 4° C. or 37° C. At predetermined time intervals, the cells were gently washed with ice-cold PBS thrice, stained with viability dye, and analyzed by flow cytometry. To assess the effect of irradiation on cellular uptake, selected groups of cells were exposed to irradiation using a RS 2000 Irradiator (Rad Source) 72 h prior to experiments. The co-culture assay was performed similarly with addition of pre-activated T cells or GL261 glioma cells into TAMC at a 1.1 ratio.

Intracellular trafficking was conducted in glass bottom confocal dishes (World Precision) with a TAMC density of $8\times10^5$ cells/dish. At predetermined time intervals, the cells were gently washed with ice-cold PBS thrice, and stained with Alexa Fluor 488-Wheat Germ Agglutinin (WGA, Fisher) at 5 μg/ml for 10 min, or LysoTracker Green DND-26 (Fisher) at 100 nM for 10 min, followed by nuclear staining using NucBlue Live Cell Stain (Fisher) for 15 min. After washed, the cells were observed under a Leica DMi8 microscope with a 20× objective. Data was processed using imageJ. In all experiments, cells were incubated with Ultra-LEAF purified anti-mouse CD16/32 antibody (BioLegend) for 10 min at 4° C. prior to incubation with LNPs to avoid non-specific binding.

PD-L1 clustering, internalization, and recycling. PD-L1 internalization and recycling was determined using a published procedure (1) with modification. In vitro generated TAMCs ($5\times10^5$ cells/well) were seeded in 24-well plate. After 24 h of culture, cells were incubated with unconjugated αPD-L1 or αPD-L1-LNP at 4° C. for 1 h. After washing twice by cold DPBS, cells were further incubated at 37° C. for 1 h to allow PD-L1 internalization and recycling. In certain groups, 300 μM of primaquine (Sigma) was added to inhibit endocytic recycling of PD-L1. Cell surface bound αPD-L1 was labeled with Alexa Fluor 488 goat-anti-rat secondary antibody (Fisher) for 30 min on ice. Remaining PD-L1 on cell surface was stained by APC anti-PD-L1 antibody (Fisher), after stripping cells twice by acidic buffer (0.5% acetic acid in 0.5 M NaCl, pH 2.6) for 2 min on ice to remove surface bound antibody. Cell surface bound αPD-L1 or remaining PD-L1 was analyzed by flow cytometry.

Clustering of PD-L1 on plasma membrane was conducted in glass bottom confocal dishes (World Precision) with a TAMC density of $8\times10^5$ cells/dish. Cells were treated with unconjugated αPD-L1 or αPD-L1-LNP on ice for 1 h, followed by incubation at 37° C. for 15 min. After washed, the cells were stained with PE anti-PD-L1 antibody (BioLegend) and observed under a Leica DMi8 microscope with a 40× objective. Data was processed using imageJ.

In vitro viability, gene expression, and PD-L1 expression of TAMCs post treatments. In vitro generated TAMCs ($8\times10^5$ cells/well) were seeded in 24-well plate. After 24 h of culture, cells were incubated with αPD-L1-LNP/Dina, αPD-L1-LNP, or free Dina. At predetermined time intervals, the cells were collected and washed, followed by the annexin V assay (BioLegend). RNA isolation was processed using the RNEasy Plus Mini Kit (Qiagen), and total RNA was quantified by Nanodrop (Thermo Scientific). cDNA was synthesized using the iScript cDNA synthesis kit (Bio-Rad), and analyzed by qPCR analysis (Bio-Rad). Selected groups of cells were exposed to irradiation and collected 72 h post treatments for cell circle analysis using BrdU Flow Kit (Fisher) following the manufacturer's protocol.

To detect the PD-L1 expression on TAMCs post treatments, in vitro generated TAMCs ($8\times10^5$ cells/well) were seeded in 24-well plate. After 24 h of culture, cells were subject to different treatments (Dina, αPD-L1/LNP, or αPD-L1-LNP/Dina) at a Dina concentration of 25 nM. Selected groups of cells were exposed to IFNγ (PeproTech) stimulation at 10 ng/ml for 24 h. Cells were collected and washed, followed by qPCR analysis or antibody staining for flow cytometry. The effect of irradiation on PD-L1 expression on TAMCs was similarly assessed 72 h post irradiation.

In vitro $CD8^+$ T cell suppression assay. TAMCs were treated with αPD-L1-LNP/Dina at a Dina concentration of 25 nM 24 h prior to experiments, followed by wash and co-culture with CellTrace Violet (CTV, Fisher) labeled $CD8^+$ T cells at designated ratios with the addition of Dynabeads (1:3 bead/T-cell ratio) and IL-2 at 50 U/ml. After 72 h of incubation, T cells were harvested, labeled with APC-efluor780 viability dye (Ebioscience), followed by staining with flow cytometry antibodies for flow cytometric analysis.

Orthotopic glioma mouse model. Six to eight weeks old mixed gender C57BL/6 (WT) or C57BL/6-Foxp3-GFP mice were anesthetized using ketamine (25 mg/ml)/xylazine (2.5 mg/ml). A skin incision (~10 mm) was made over the middle frontal to parietal bone. Glioma cells in 2.5 μl of sterile saline were injected into the mouse brain at a depth of 3 mm through a transcranial burr hole located at coordinates 2 mm caudal relative to bregma and 2 mm right of the cranial midline suture. Standard post-surgery care was given following the IACUC-approved protocol.

Isolation of mouse glioma infiltrating immune cells. The mice were euthanized by $CO_2$ and perfused with 5 ml of DPBS intracardially. Brain/tumor single cell suspension was obtained in Hank's balanced salt solution (HBSS, Gibco)

using a tissue homogenizer (Potter-Elvehjem PTFE pestle), followed by removal of myelin and debris by 30/70 Percoll gradient separation (GE Healthcare). Glioma infiltrating immune cells were collected into complete RPMI for phenotyping or ex vivo study.

Human GBM and blood samples. All human tumor and peripheral blood samples were collected by the Nervous System Tumor Bank of the Northwestern University (NSTB) under the IRB protocol No STU00202003. Brain tumor samples were diced and digested in 4 ml of HBSS (Gibco) with the addition of 80 μg DNaseI (Sigma), 40 μg TLCK (Sigma), and 8 mg of collagenase D (Sigma) per 2 g of tumor sample, followed by incubation at 37° C. for 30 min with pipetting the samples every 10 min. Single cell suspension was obtained in HBSS using a tissue homogenizer and filtered using a 70 μm cell strainer (Fischer). Myelin and debris were removed by 30/70 Percoll gradient separation (GE Healthcare) for 30 min at 1000×g at room temperature. Peripheral blood mononuclear cells (PBMC) were isolated by Ficoll gradient (GE Healthcare) from peripheral blood samples of GBM patients. All isolated cells were immediately put into complete RPMI media.

TAMC targeting and elimination in ex vivo mice and human glioma models. Cell suspension collected from mouse or human samples was plated into 96 well U bottom plate. Cells were pre-blocked with Ultra-LEAF purified anti-mouse CD16/32 antibody or Human TruStain FcX (BioLegend) for 10 min at 4° C., followed by incubation with fluorescence labeled LNPs (0.15 mg lipids/ml) for 1 h at 37° C. in 5% $CO_2$ humidified atmosphere. After gently washed with ice-cold PBS thrice, the cells were collected for staining with viability dye and antibodies. The cellular uptake was analyzed by flow cytometry. The ex vivo TAMC elimination assay was performed using cell suspension collected from mouse glioma samples. Cells were plated into 96 well U bottom plate in 50% complete RPMI and 50% conditioned media collected from GL261 glioma cell culture as aforementioned. Cells were subject to the treatment of αPD-L1/LNP/Dina or free Dina at a Dina concentration of 0, 25, and 50 nM for 72 h, and analyzed by flow cytometry.

Cannula implantation and intracranial injection through cannula. Mice were anesthetized with ketamine/xylazine as above described. A 26-gauge sterile guide cannula for mice (Plastics One) was installed into the mouse brain at a depth of 2 mm through the burr hole generated in skull as aforementioned. The stable positioning of the implanted cannula was secured by applying surgical glue around the burr hole. The protrusion of the cannula was further protected by a 33-gauge protection dummy cannula (Plastics One). Standard post-surgery care was given according to the IACUC-approved protocol. During injection, a 33-gauge sterile neuros syringe (Hamilton), equipped with a sleeve designed to extend 1 mm beyond the tip of the guide cannula, was used to inject diluted cells or therapeutics in sterile 0.9% saline through the installed guide cannula. After injection, the cannula was covered with a 33-gauge dummy cannula for mice.

In vivo distribution and therapeutic study of LNPs. C57BL/6 mice of 4-6 weeks old were intracranially implanted with GL261 murine glioma cells ($5\times10^4$ cells per mouse). Mice were randomly grouped, and treated with saline, αPD-L1-LNP, IgG-LNP/Dina, or αPD-L1-LNP/Dina (2.5 mg Dina per kg) on the seventh and fourteenth day post tumor implantation by intracranial administration through cannula system. The therapeutic efficacy of free Dina was evaluated similarly with injection of Dina dissolved in 20% 2-hydroxypropyl-β-cyclodextran (Cayman) at 2.5 mg or 5 mg Dina per kg. Animal survival was recorded following endpoint protocols outlined in the approved animal protocols.

In vivo distribution study was conducted two weeks post tumor implantation. Mice were intracranially injected with fluorescence labeled αPD-L1-LNP. 24 h post injection, mice were euthanized by $CO_2$ and perfused with 5 ml of DPBS. Mouse brains were harvested for immunofluorescence staining.

In vivo therapeutic study of therapeutic LNPs combined with radiation therapy. C57BL/6 mice of 4-6 weeks old were intracranially implanted with GL261 murine glioma cells ($5\times10^4$ cells per mouse). Mice were randomly grouped, and treated with saline, αPD-L1-LNP, or αPD-L1-LNP/Dina (2.5 mg Dina per kg) on the seventh and fourteenth day post tumor implantation by intracranial administration through cannula system. All mice were also exposed to a 2 Gy daily dose of irradiation, using a Gammacell 40 Exactor (Best Theratronics), for four consecutive days starting on the seventh day after tumor cell implantation. Specifically, mice were anesthetized, the body of animals with an exception of the head was shielded with lead shields. All mice were followed to record their survival following endpoint protocols outlined in the approved animal protocols.

The therapeutic efficacy was further evaluated in a more aggressive glioma model in C57BL/6 mice with intracranial implantation of $2\times10^5$ GL261 glioma cells per mouse. Mice were treated with saline, αPD-L1-LNP, or αPD-L1-LNP/Dina (5 mg Dina per kg) as above described, and two groups of mice treated with saline, or αPD-L1-LNP/Dina were also exposed to a 2 Gy daily dose of irradiation for four consecutive days. The glioma infiltrating immune cells were collected on the sixteenth day and analyzed by flow cytometry. The brain tissues were also collected for histo-physiological analysis.

Survival of mice bearing CT2A model was similarly performed by intracranial implantation with CT2A murine glioma cells ($5\times10^4$ cells per mouse). The therapeutic efficacy of αPD-L1-LNP/Dina through intranasal administration was similarly evaluated in GL261 model ($5\times10^4$ cells per mouse) by intranasally giving sterile saline or αPD-L1-LNP/Dina (5 mg Dina per kg) for eight consecutive days starting on the seventh day after tumor cell implantation. In brief, the anesthetized mice were given 10 μl of sterile saline or αPD-L1-LNP/Dina given as 2 μl fractions in each nostril at 5 min intervals.

Flow cytometry analysis. For in vitro studies the following flow cytometry panel was used in addition to CTV and viability dye: anti-CD45 PE-Cy7, anti-CD11b BV711, anti-Ly6C Alexa Fluor 700, anti-Ly6G PerCP-Cy5.5, anti-CD4 APC, anti-CD8 BV605, anti-PD-L1 PE all at a 1:200 dilution purchased from Biolegend. For in vivo and ex vivo studies, the following flow cytometry panel was used in conjunction with viability dye: anti-CD45 PE-Cy7, anti-CD11b BV711, anti-CD11c APC, anti-Ly6C Alexa Fluor 700, anti-Ly6G PerCP-Cy5.5, anti-CD4 Pacific Blue, anti-CD8 BV605, anti-PD-L1 PE all at a 1:200 dilution and were purchased from Biolegend. Endogenous Foxp3 expression was detected via GFP fluorescence. For human patient sample analysis, the following flow cytometry panel was used in conjunction with viability dye: anti-CD11b BV711, anti-CD33 PE-Cy7, anti-CD14 BV605, anti-CD15 FITC, anti-PY2R12 BV421, anti-CD3 BV711, anti-CD4 PE-Cy7, anti-CD8 BV421, anti-PD-L1 APC all at a 1:40 dilution and were purchased from Biolegend. Cells were pre-blocked with Ultra-LEAF purified anti-mouse CD16/32 antibody or Human TruStain FcX (BioLegend) for 10 min at 4° C.

before antibody staining. All acquisition was performed using a BD FACSymphony flow cytometer. Data analysis was performed via FlowJo software.

Tissue staining. The mice were euthanized by $CO_2$ and perfused with 5 ml of DPBS. Brain tissues were collected, flash frozen in OCT (Fisher), and sectioned into 8 μm slices using a Leica CM1860 cryostat (Leica, Wetzlar, Germany). Sections were fixed in 4% paraformaldehyde in PBS (Fisher). Immunofluorescence staining was conducted by incubation overnight at 4° C. with Alexa Fluor-488 anti-CD11b (Ebioscience) 1:100 in TBS (Boston Bioproducts) containing 0.5% triton-X 100 and 1% BSA (Sigma). The following day, slides were washed and mounted using Fluoroshield with DAPI (Sigma). Images were taken with a Leica DMi8 microscope with a 20× objective. Hematoxylin and eosin (H&E) staining was performed using Mayer's hematoxylin solution (Sigma) and Eosin Y solution (Sigma), and images were taken with a BioTek Cytation 5 Cell Imaging Multi-Mode Reader. Data was processed using imageJ.

Statistical analysis. All statistical analyses were performed with Prism Graph-Pad 7 Software. Student's t test was used to compare the two groups. Multiple groups were analyzed with one-way ANOVA, followed by Tukey's post hoc test. Longitudinal data from multiple groups were analyzed with two-way ANOVA followed by Tukey's post hoc test. All numerical data were reported as mean±SEM. Kaplan-Meier plots were generated to determine relative survival of glioma bearing animals under different courses of treatment, and p values for curve comparisons were calculated using the Log-rank method followed by Bonferroni correction. *p<0.05; p<0.01; *p<0.001; n.s. not significant.

Tables

TABLE 1

Characteristics of GBM patient samples.

| Sample ID | Gender | Race | Ethnicity | Treatment prior to sample collection TMZ | RT | IDH1 status | MGMT methylation |
|---|---|---|---|---|---|---|---|
| NU01761 | Male | White | Non-hispanic | No | No | WT | Positive |
| NU01794 | Male | Asian | Non-hispanic | Yes | Yes | WT | N/A |
| NU02033 | Female | White | Hispanic | Yes | Yes | Mutated | Positive |
| NU02056 | Female | White | Non-hispanic | Yes | Yes | WT | Positive |

TMZ, temozolomide; RT, radiation therapy; WT, wild type; IDH, isocitrate dehydrogenase; MGMT, $O^6$-methylguanine DNA methyltransferase.

REFERENCES

1. I. Melero et al., Evolving synergistic combinations of targeted immunotherapies to combat cancer. Nat Rev Cancer 15, 457-472 (2015).
2. I. Mellman, G. Coukos, G. Dranoff, Cancer immunotherapy comes of age. Nature 480, 480-489 (2011).
3. D. M. Pardoll, The blockade of immune checkpoints in cancer immunotherapy. Nat Rev Cancer 12, 252-264 (2012).
4. H. J. Jackson, S. Rafiq, R. J. Brentjens, Driving CAR T-cells forward. Nat Rev Clin Oncol 13, 370-383 (2016).
5. C. H. June, R. S. O'Connor, O. U. Kawalekar, S. Ghassemi, M. C. Milone, CAR T cell immunotherapy for human cancer. Science 359, 1361-1365 (2018).
6. M. L. Davila et al., Efficacy and Toxicity Management of 19-28z CAR T Cell Therapy in B Cell Acute Lymphoblastic Leukemia. Sci Transl Med 6 (2014).
7. W. P. Zou, Immunosuppressive networks in the tumour environment and their therapeutic relevance. Nat Rev Cancer 5, 263-274 (2005).
8. P. Sharma, S. Hu-Lieskovan, J. A. Wargo, A. Ribas, Primary, Adaptive, and Acquired Resistance to Cancer Immunotherapy. Cell 168, 707-723 (2017).
9. H. Liang et al., Host STING-dependent MDSC mobilization drives extrinsic radiation resistance. Nat Commun 8, 1736 (2017).
10. W. Leonard et al., Myeloid-derived suppressor cells reveal radioprotective properties through arginase-induced 1-arginine depletion. Radiother Oncol 119, 291-299 (2016).
11. M. Baghdadi et al., Chemotherapy-Induced IL34 Enhances Immunosuppression by Tumor-Associated Macrophages and Mediates Survival of Chemoresistant Lung Cancer Cells. Cancer Res 76, 6030-6042 (2016).
12. D. J. Brat et al., Comprehensive, Integrative Genomic Analysis of Diffuse Lower-Grade Gliomas. New Engl J Med 372, 2481-2498 (2015).
13. R. Stupp et al., Radiotherapy plus concomitant and adjuvant temozolomide for glioblastoma. N Engl J Med 352, 987-996 (2005).
14. L. M. DeAngelis, Brain tumors. N Engl J Med 344, 114-123 (2001).
15. M. Preusser, M. Lim, D. A. Hafler, D. A. Reardon, J. H. Sampson, Prospects of immune checkpoint modulators in the treatment of glioblastoma. Nat Rev Neurol 11, 504-514 (2015).
16. D. F. Quail, J. A. Joyce, The Microenvironmental Landscape of Brain Tumors. Cancer Cell 31, 326-341 (2017).
17. B. Raychaudhuri et al., Myeloid-derived suppressor cell accumulation and function in patients with newly diagnosed glioblastoma. Neuro-Oncology 13, 591-599 (2011).
18. M. Lim, Y. X. Xia, C. Bettegowda, M. Weller, Current state of immunotherapy for glioblastoma. Nature Reviews Clinical Oncology 15, 422-442 (2018).
19. A. Sica et al., Origin and Functions of Tumor-Associated Myeloid Cells (TAMCs). Cancer Microenviron 5, 133-149 (2012).
20. H. Qin et al., Targeting tumor-associated myeloid cells for cancer immunotherapy. Oncoimmunology 4, e983961 (2015).
21. D. I. Gabrilovich, S. Nagaraj, Myeloid-derived suppressor cells as regulators of the immune system. Nat Rev Immunol 9, 162-174 (2009).
22. A. L. Chang et al., CCL2 Produced by the Glioma Microenvironment Is Essential for the Recruitment of Regulatory T Cells and Myeloid-Derived Suppressor Cells. Cancer Res 76, 5671-5682 (2016).

23. T. J. Alban et al., Global immune fingerprinting in glioblastoma patient peripheral blood reveals immune-suppression signatures associated with prognosis. JCI Insight 3 (2018).
24. G. Hutter et al., Microglia are effector cells of CD47-SIRPalpha antiphagocytic axis disruption against glioblastoma. Proc Natl Acad Sci USA 116, 997-1006 (2019).
25. J. P. Antonios et al., Immunosuppressive tumor-infiltrating myeloid cells mediate adaptive immune resistance via a PD-1/PD-L1 mechanism in glioblastoma. Neuro Oncol 19, 796-807 (2017).
26. O. Bloch et al., Gliomas Promote Immunosuppression through Induction of B7-H1 Expression in Tumor-Associated Macrophages. Clin Cancer Res 19, 3165-3175 (2013).
27. V. Fleming et al., Targeting Myeloid-Derived Suppressor Cells to Bypass Tumor-Induced Immunosuppression. Front Immunol 9, 398 (2018).
28. J. L. Benci et al., Tumor Interferon Signaling Regulates a Multigenic Resistance Program to Immune Checkpoint Blockade. Cell 167, 1540-1554 e1512 (2016).
29. C. Engblom, C. Pfirschke, M. J. Pittet, The role of myeloid cells in cancer therapies. Nat Rev Cancer 16, 447-462 (2016).
30. M. L. Burr et al., CMTM6 maintains the expression of PD-L1 and regulates anti-tumour immunity. Nature 549, 101-105 (2017).
31. R. D. Dorand et al., Cdk5 disruption attenuates tumor PD-L1 expression and promotes antitumor immunity. Science 353, 399-403 (2016).
32. M. Z. Noman et al., PD-L1 is a novel direct target of HIF-1alpha, and its blockade under hypoxia enhanced MDSC-mediated T cell activation. J Exp Med 211, 781-790 (2014).
33. A. W. van Weert, H. J. Geuze, B. Groothuis, W. Stoorvogel, Primaquine interferes with membrane recycling from endosomes to the plasma membrane through a direct interaction with endosomes which does not involve neutralisation of endosomal pH nor osmotic swelling of endosomes. Eur J Cell Biol79, 394-399 (2000).
34. I. Nakase et al., Receptor clustering and activation by multivalent interaction through recognition peptides presented on exosomes. Chem Commun (Camb) 53, 317-320 (2016).
35. D. I. Gabrilovich, S. Ostrand-Rosenberg, V. Bronte, Coordinated regulation of myeloid cells by tumours. Nature Reviews Immunology 12, 253-268 (2012).
36. J. Mann, R. Ramakrishna, R. Magge, A. G. Wernicke, Advances in Radiotherapy for Glioblastoma. Front Neurol 8 (2018).
37. A. A. Lugade et al., Local radiation therapy of B16 melanoma tumors increases the generation of tumor antigen-specific effector cells that traffic to the tumor. J Immunol 174, 7516-7523 (2005).
38. A. Kalbasi, C. H. June, N. Haas, N. Vapiwala, Radiation and immunotherapy: a synergistic combination. J Clin Invest 123, 2756-2763 (2013).
39. L. Deng et al., STING-Dependent Cytosolic DNA Sensing Promotes Radiation-Induced Type I Interferon-Dependent Antitumor Immunity in Immunogenic Tumors. Immunity 41, 843-852 (2014).
40. T. Oh et al., Immunocompetent murine models for the study of glioblastoma immunotherapy. J Transl Med 12, 107 (2014).
41. R. Weber et al., Myeloid-Derived Suppressor Cells Hinder the Anti-Cancer Activity of Immune Checkpoint Inhibitors. Front Immunol 9, 1310 (2018).
42. K. J. Cho, X. Wang, S. M. Nie, Z. Chen, D. M. Shin, Therapeutic nanoparticles for drug delivery in cancer. Clin Cancer Res 14, 1310-1316 (2008).
43. G. T. Tietjen, L. G. Bracaglia, W. M. Saltzman, J. S. Pober, Focus on Fundamentals: Achieving Effective Nanoparticle Targeting. Trends Mol Med 24, 598-606 (2018).
44. Y. J. Kim, S. J. Park, H. E. Broxmeyer, Phagocytosis, a potential mechanism for myeloid-derived suppressor cell regulation of CD8+ T cell function mediated through programmed cell death-1 and programmed cell death-1 ligand interaction. J Immunol 187, 2291-2301 (2011).
45. U. Bulbake, S. Doppalapudi, N. Kommineni, W. Khan, Liposomal Formulations in Clinical Use: An Updated Review. Pharmaceutics 9 (2017).
46. T. M. Allen, P. R. Cullis, Liposomal drug delivery systems: from concept to clinical applications. Adv Drug Deliv Rev 65, 36-48 (2013).
47. M. L. Burr et al., CMTM6 maintains the expression of PD-L1 and regulates anti-tumour immunity. *Nature* 549, 101-105 (2017).

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method for treating a cancer comprising tumor-associated myeloid cells (TAMCs) in a subject in need thereof, the method comprising administering to the subject a pharmaceutical composition comprising cytotoxic lipid particles and a suitable carrier, excipient, or diluent, wherein the cytotoxic lipid particles comprise a surface-associated antibody or antigen-binding fragment thereof against PD-L1 and a cytotoxic agent, wherein the cytotoxic agent is Dinaciclib (Dina), wherein the cytotoxic lipid particles are nanoparticles comprising a phospholipid bilayer encapsulating the cytotoxic agent, and wherein the cancer is glioblastoma.

2. The method of claim 1, where in the pharmaceutical composition is administered intracranially.

3. The method of claim 1, wherein the pharmaceutical composition is administered intranasally.

4. The method of claim 1, further comprising administering to the subject radiotherapy.

5. The method of claim 1, wherein the cytotoxic lipid particles comprise a suitable concentration of the cytotoxic agent for treating a tumor at a concentration of about 1-300 μg of cytotoxic agent/mg of lipids.

6. The method of claim 1, wherein the cytotoxic lipid particles comprise liposomes.

7. The method of claim 1, wherein the surface-associated antibody or antigen-binding fragment thereof against PD-L1 is covalently attached to the cytotoxic lipid particles via functionalized phospholipids.

8. The method of claim 1, wherein the phospholipid bilayer comprises cholesterol.

9. A method of reducing the frequency of radioresistant monocytic myeloid-derived suppressor cells (M-MDSCs) in a subject receiving radiotherapy, the method comprising administering to the subject a pharmaceutical composition comprising cytotoxic lipid particles and a suitable carrier, excipient, or diluent, wherein the cytotoxic lipid particles comprise a surface-associated antibody or antigen-binding fragment thereof against PD-L1 and a cytotoxic agent, wherein the cytotoxic agent is Dinaciclib (Dina), wherein the cytotoxic lipid particles are nanoparticles comprising a phospholipid bilayer encapsulating the cytotoxic agent.

10. The method of claim 9, wherein the cytotoxic lipid particles comprise a suitable concentration of the cytotoxic agent for treating a tumor at a concentration of about 1-300 μg of cytotoxic agent/mg of lipids.

11. The method of claim 9, wherein the cytotoxic lipid particles comprise liposomes.

12. The method of claim 9, wherein the surface-associated antibody or antigen-binding fragment thereof against PD-L1 is covalently attached to the cytotoxic lipid particles via functionalized phospholipids.

13. The method of claim 9, wherein the phospholipid bilayer comprises cholesterol.

14. A method of reducing PD-L1 endocytic recycling in tumor-associated myeloid cells (TAMCs) in a subject that has been diagnosed with a cancer, the method comprising administering to the subject a pharmaceutical composition comprising cytotoxic lipid particles and a suitable carrier, excipient, or diluent, wherein the cytotoxic lipid particles comprise a surface-associated antibody or antigen-binding fragment thereof against PD-L1 and a cytotoxic agent, wherein the cytotoxic agent is Dinaciclib (Dina), wherein the cytotoxic lipid particles are nanoparticles comprising a phospholipid bilayer encapsulating the cytotoxic agent.

15. The method of claim 14, wherein the cancer is glioblastoma.

16. The method of claim 14, further comprising administering to the subject radiotherapy.

17. The method of claim 14, wherein the cytotoxic lipid particles comprise a suitable concentration of the cytotoxic agent for treating a tumor at a concentration of about 1-300 μg of cytotoxic agent/mg of lipids.

18. The method of claim 14, wherein the cytotoxic lipid particles comprise liposomes.

19. The method of claim 14, wherein the surface-associated antibody or antigen-binding fragment thereof against PD-L1 is covalently attached to the cytotoxic lipid particles via functionalized phospholipids.

20. The method of claim 14, wherein the phospholipid bilayer comprises cholesterol.

* * * * *